United States Patent
Fischer et al.

(10) Patent No.: US 10,550,116 B2
(45) Date of Patent: Feb. 4, 2020

(54) FUSED BICYCLIC HETEROCYCLE DERIVATIVES AS PESTICIDES

(71) Applicant: BAYER CROPSCIENCE AKTIENGESELLSCHAFT, Monheim am Rhein (DE)

(72) Inventors: Rüdiger Fischer, Pulheim (DE); Dominik Hager, Monheim (DE); Laura Hoffmeister, Düsseldorf (DE); Nina Kausch-Busies, Bergisch Gladbach (DE); David Wilcke, Düsseldorf (DE); Matthieu Willot, Düsseldorf (DE); Ulrich Görgens, Ratingen (DE); Kerstin Ilg, Köln (DE); Marc Mosrin, Köln (DE); Daniela Portz, Vettweiß (DE); Andreas Turberg, Haan (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/770,738

(22) PCT Filed: Oct. 21, 2016

(86) PCT No.: PCT/EP2016/075365
§ 371 (c)(1),
(2) Date: Apr. 24, 2018

(87) PCT Pub. No.: WO2017/072039
PCT Pub. Date: May 4, 2017

(65) Prior Publication Data
US 2018/0305353 A1   Oct. 25, 2018

(30) Foreign Application Priority Data
Oct. 26, 2015   (EP) .................... 15191440

(51) Int. Cl.
| C07D 471/04 | (2006.01) |
| C07D 401/04 | (2006.01) |
| C07D 413/04 | (2006.01) |
| C07D 487/04 | (2006.01) |
| C07D 491/056 | (2006.01) |
| C07D 498/04 | (2006.01) |
| C07D 519/00 | (2006.01) |
| A01N 43/52 | (2006.01) |
| A01N 43/76 | (2006.01) |
| A01N 43/90 | (2006.01) |

(52) U.S. Cl.
CPC .......... C07D 471/04 (2013.01); A01N 43/52 (2013.01); A01N 43/76 (2013.01); A01N 43/90 (2013.01); C07D 401/04 (2013.01); C07D 413/04 (2013.01); C07D 487/04 (2013.01); C07D 491/056 (2013.01); C07D 498/04 (2013.01); C07D 519/00 (2013.01)

(58) Field of Classification Search
CPC .................................................. C07D 233/64
See application file for complete search history.

(56) References Cited

FOREIGN PATENT DOCUMENTS

| EP | 0338346 A2 | 10/1989 |
| WO | 2010/125985 A1 | 11/2010 |
| WO | 2011/122815 A2 | 10/2011 |
| WO | 2012/074135 A1 | 6/2012 |
| WO | 2012/086848 A1 | 6/2012 |
| WO | WO2012086848 | * 6/2012 |
| WO | 2013/018928 A1 | 2/2013 |
| WO | 2013/191113 A1 | 12/2013 |
| WO | 2014/142292 A1 | 9/2014 |

(Continued)

OTHER PUBLICATIONS

Hu, Yongzhou et al., "Phenylsulfonyl quinoxaline-like compound, its preparation process and medical application for treating neoplasm", Chemical Abstract, 2011, XP002751906.

(Continued)

*Primary Examiner* — Paul V Ward
(74) *Attorney, Agent, or Firm* — McBee Moore & Vanik IP, LLC

(57) ABSTRACT

The invention relates to novel compounds of the formula (I) or (I')

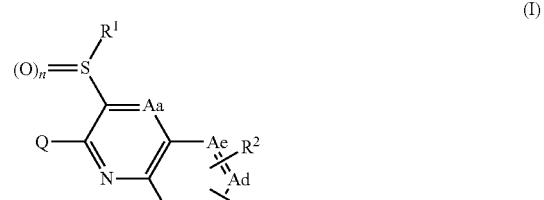

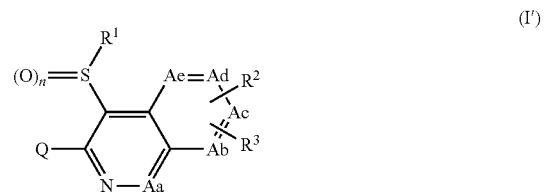

in which $R^1$, $R^2$, $R^3$, Aa, Ab, Ac, Ad, Ae, Q and n have the definitions given above,
to the use thereof as acaricides and/or insecticides for controlling animal pests and to processes and intermediates for the preparation thereof.

19 Claims, No Drawings

(56) References Cited

FOREIGN PATENT DOCUMENTS

| WO | 2014/148451 A1 | 9/2014 |
|---|---|---|
| WO | 2015/000715 A1 | 1/2015 |
| WO | 2015/002211 A1 | 1/2015 |
| WO | 2015/071180 A1 | 5/2015 |
| WO | 2015/091945 A1 | 6/2015 |
| WO | 2015/121136 A1 | 8/2015 |
| WO | 2015/133603 A1 | 9/2015 |
| WO | 2015/198817 A1 | 12/2015 |
| WO | 2015/198859 A1 | 12/2015 |
| WO | 2016/005263 A1 | 1/2016 |
| WO | 2016/020286 A1 | 2/2016 |
| WO | 2016/023954 A2 | 2/2016 |
| WO | 2016/026848 A1 | 2/2016 |
| WO | 2016/039441 A1 | 3/2016 |
| WO | 2016/039444 A1 | 3/2016 |
| WO | 2016/041819 A1 | 3/2016 |
| WO | 2016/046071 A1 | 3/2016 |
| WO | 2016/091731 A1 | 6/2016 |
| WO | 2016/107742 A1 | 7/2016 |
| WO | 2016/124557 A1 | 8/2016 |
| WO | 2016/124563 A1 | 8/2016 |
| WO | 2016/142326 A1 | 9/2016 |

OTHER PUBLICATIONS

Hu, Yongzhou et al., "Preparation of substituted quinoxaline amine compounds as antitumor agents", Chemical Abstract, 2011, XP002751907.
Chemical Abstract, 2011, XP002751908.
European Application No. 15153943.4, filed Feb. 5, 2015.
European Patent Application No. 15153948.3, filed Feb. 5, 2015.
International Search Report of International Patent Application No. PCT/EP2016/075365 dated Nov. 24, 2016.

* cited by examiner

FUSED BICYCLIC HETEROCYCLE DERIVATIVES AS PESTICIDES

CROSS-REFERENCE TO RELATED APPLICATIONS

This application is a National Stage entry of International Application No. PCT/EP2016/075365, filed 21 Oct. 2016, which claims priority to European Patent Application No. 15191440.5, filed 26 Oct. 2015.

BACKGROUND

Field

The present invention relates to novel fused bicyclic heterocycle derivatives of the formula (I) or of the formula (I'), to the use thereof as acaricides and/or insecticides for controlling animal pests, particularly arthropods and especially insects and arachnids, and to processes and intermediates for the preparation thereof.

Description of Related Art

Fused bicyclic heterocycle derivatives with insecticidal properties are already described in the literature, for example in WO 2010/125985, WO 2012/074135, WO 2012/086848, WO 2013/018928, WO 2013/191113, WO 2014/142292, WO 2014/148451, WO 2015/000715, EP 15153943.4, EP 15153948.3 and WO 2015/121136.

Fused bicyclic heterocycle derivatives with insecticidal properties have also already been described in the literature, for example in WO2016/091731, WO2016/039444, WO2015/198859, WO 2015/133603, WO 2015/198859, WO 2015/002211, WO 2015/071180, WO 2015/091945, WO 2016/005263, WO 2015/198817, WO 2016/041819, WO 2016/039441, WO 2016/026848, WO 2016/023954, WO 2016/020286 and WO 2016/046071.

However, the active ingredients already known according to the documents cited above have disadvantages on application to some degree, whether because they have only a narrow scope of application or because they do not have satisfactory insecticidal or acaricidal action.

SUMMARY

Novel fused bicyclic heterocycle derivatives have now been found, these have advantages over the compounds already known, examples of which include better biological or environmental properties, a wider range of application methods, better insecticidal or acaricidal action, and good compatibility with crop plants. The fused bicyclic heterocycle derivatives can be used in combination with further agents for improving efficacy, especially against insects that are difficult to control.

The present invention therefore provides novel compounds of the formula (I) or (I')

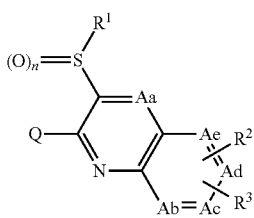

(I)

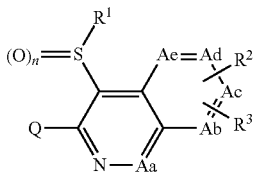

(I')

in which (configuration 1)
Aa is nitrogen or $=C(R^7)-$,
Ab is nitrogen or $=C(H)-$,
Ac is nitrogen or $=C(H)-$,
Ad is nitrogen or $=C(H)-$,
Ae is nitrogen or $=C(H)-$,
where Ab, Ac, Ad and Ae cannot all be nitrogen,
$R^1$ ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_5$)cycloalkyl, halo($C_3$-$C_8$)cycloalkyl, amino, ($C_1$-$C_6$)alkylamino, di-($C_1$-$C_6$)alkylamino, ($C_3$-$C_8$)cycloalkylamino, ($C_1$-$C_6$)alkylcarbonylamino, ($C_1$-$C_6$)alkylthio-($C_1$-$C_6$)alkyl, ($C_1$-$C_6$)haloalkylthio-($C_1$-$C_6$)-alkyl, ($C_1$-$C_6$)alkylsulphinyl-($C_1$-$C_6$)-alkyl, ($C_1$-$C_6$)haloalkylsulphinyl-($C_1$-$C_6$)alkyl, ($C_1$-$C_6$)alkylsulphonyl-($C_1$-$C_6$)alkyl, ($C_1$-$C_6$)haloalkylsulphonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulphinyl-($C_1$-$C_6$)alkyl, ($C_1$-$C_6$)alkoxy-($C_1$-$C_6$)alkylsulphonyl-($C_1$-$C_6$)-alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, ($C_1$-$C_6$)alkylsulphonylamino, aminosulphonyl-($C_1$-$C_6$)alkyl, ($C_1$-$C_6$)alkylaminosulphonyl-($C_1$-$C_6$)alkyl, di-($C_1$-$C_6$)alkylaminosulphonyl-($C_1$-$C_6$)alkyl,
or ($C_1$-$C_6$)alkyl, ($C_1$-$C_6$)alkoxy, ($C_2$-$C_6$)alkenyl, ($C_2$-$C_6$)alkynyl, ($C_3$-$C_8$)cycloalkyl, each optionally mono- or polysubstituted identically or differently by aryl, hetaryl or heterocyclyl, where aryl, hetaryl or heterocyclyl may each optionally be mono- or polysubstituted identically or differently by halogen, cyano, nitro, hydroxyl, amino, carboxyl, carbamoyl, aminosulphonyl, ($C_1$-$C_6$)alkyl, ($C_3$-$C_6$)cycloalkyl, ($C_1$-$C_6$)alkoxy, ($C_1$-$C_6$)haloalkyl, ($C_1$-$C_6$)haloalkoxy, ($C_1$-$C_6$)alkylthio, ($C_1$-$C_6$)alkylsulphinyl, ($C_1$-$C_6$)alkylsulphonyl, ($C_1$-$C_6$)alkylsulphimino, ($C_1$-$C_6$)alkylsulphimino-($C_1$-$C_6$)alkyl, ($C_1$-$C_6$)alkylsulphimino-($C_2$-$C_6$)alkylcarbonyl, ($C_1$-$C_6$)alkylsulphoximino, ($C_1$-$C_6$)alkylsulphoximino-($C_1$-$C_6$)alkyl, ($C_1$-$C_6$)alkylsulphoximino-($C_2$-$C_6$)alkylcarbonyl, ($C_1$-$C_6$)alkoxycarbonyl, ($C_1$-$C_6$)alkylcarbonyl, ($C_3$-$C_6$)trialkylsilyl or benzyl, or
$R^1$ is aryl, hetaryl or heterocyclyl, each mono- or polysubstituted identically or differently by halogen, cyano, nitro, hydroxyl, amino, carboxyl, carbamoyl, ($C_1$-$C_6$)alkyl, ($C_3$-$C_8$)cycloalkyl, ($C_1$-$C_6$)-alkoxy, ($C_1$-$C_6$)haloalkyl, ($C_1$-$C_6$)haloalkoxy, ($C_1$-$C_6$)alkylthio, ($C_1$-$C_6$)alkylsulphinyl, ($C_1$-$C_6$)alkylsulphonyl, ($C_1$-$C_6$)alkylsulphimino, ($C_1$-$C_6$)alkylsulphimino-($C_1$-$C_6$)alkyl, ($C_1$-$C_6$)alkylsulphimino-($C_2$-$C_6$)alkylcarbonyl, ($C_1$-$C_6$)alkylsulphoximino, ($C_1$-$C_6$)alkylsulphoximino-($C_1$-$C_6$)alkyl, ($C_1$-$C_6$)alkylsulphoximino-($C_2$-$C_6$)alkylcarbonyl, ($C_1$-$C_6$)

alkoxycarbonyl, $(C_1-C_6)$alkylcarbonyl, $(C_3-C_6)$trialkylsilyl, (=O) (in the case of heterocyclyl only) and (=O)$_2$ (in the case of heterocyclyl only), R$^2$, R$^3$ are independently hydrogen, cyano, halogen, nitro, acetyl, hydroxyl, amino, SCN, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulphinyl, $(C_1-C_6)$haloalkylsulphinyl, $(C_1-C_6)$alkoxy-$(C_1-C_6)$alkylsulphinyl, $(C_1-C_6)$alkylsulphinyl-$(C_1-C_6)$alkyl, $(C_1-C_6)$alkylsulphonyl, $(C_1-C_6)$haloalkylsulphonyl, $(C_1-C_6)$alkoxy-$(C_1-C_6)$alkylsulphonyl, $(C_1-C_6)$alkylsulphonyl-$(C_1-C_6)$alkyl, $(C_1-C_6)$alkylsulphonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di-$(C_1-C_6)$alkylaminocarbonyl, di-$(C_1-C_6)$alkylaminothiocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulphonylamino, $(C_1-C_6)$alkylamino, di-$(C_1-C_6)$alkylamino, aminosulphonyl, $(C_1-C_6)$alkylaminosulphonyl, di-$(C_1-C_6)$alkylaminosulphonyl, $(C_1-C_6)$alkylsulphoximino, aminothiocarbonyl, $(C_1-C_6)$alkylaminothiocarbonyl, di-$(C_1-C_6)$alkylaminothiocarbonyl, $(C_3-C_8)$cycloalkylamino or NHCO—$(C_1-C_6)$alkyl $((C_1-C_6)$alkylcarbonylamino), R$^7$ is hydrogen, cyano, halogen, acetyl, hydroxyl, amino, $(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_2-C_6)$alkenyl, $(C_2-C_6)$haloalkenyl, $(C_2-C_6)$alkynyl, $(C_2-C_6)$haloalkynyl, $(C_1-C_6)$alkoxy, $(C_1-C_6)$haloalkoxy, $(C_1-C_6)$alkylthio, $(C_1-C_6)$haloalkylthio, $(C_1-C_6)$alkylsulphinyl, $(C_1-C_6)$haloalkylsulphinyl, $(C_1-C_6)$alkylsulphonyl or $(C_1-C_6)$haloalkylsulphonyl, Q is a partly saturated or saturated heterocyclic or heteroaromatic 8-, 9-, 10-, 11- or 12-membered fused bicyclic or tricyclic ring system, where at least one carbonyl group may optionally be present and/or where the ring system is optionally mono- or polysubstituted identically or differently, and where the substituents may independently be selected from hydrogen, cyano, halogen, nitro, acetyl, hydroxyl, amino, SCN, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$alkynyloxy-$(C_1-C_4)$alkyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$haloalkoxy-$(C_1-C_6)$alkyl, $(C_2-C_6)$alkenyloxy-$(C_1-C_6)$alkyl, $(C_2-C_6)$haloalkenyloxy-$(C_1-C_6)$alkyl, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulphinyl, $(C_1-C_6)$alkylsulphinyl-$(C_1-C_6)$alkyl, $(C_1-C_6)$haloalkylsulphinyl, $(C_1-C_6)$alkoxy-$(C_1-C_6)$alkylsulphinyl, $(C_1-C_6)$alkylsulphonyl, $(C_1-C_6)$haloalkylsulphonyl, $(C_1-C_6)$alkoxy-$(C_1-C_6)$alkylsulphonyl, $(C_1-C_6)$alkylsulphonyl-$(C_1-C_6)$alkyl, $(C_1-C_6)$alkylsulphonyloxy, $(C_1-C_6)$alkylcarbonyl, $(C_1-C_6)$alkylcarbonyl-$(C_1-C_6)$alkyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di-$(C_1-C_6)$alkylaminocarbonyl, di-$(C_1-C_6)$alkylaminothiocarbonyl, $(C_2-C_6)$alkenylaminocarbonyl, di-$(C_2-C_6)$-alkenylaminocarbonyl, $(C_3-C_8)$cycloalkylaminocarbonyl, $(C_1-C_6)$alkylsulphonylamino, $(C_1-C_6)$alkylamino, di-$(C_1-C_6)$alkylamino, aminosulphonyl, $(C_1-C_6)$alkylaminosulphonyl, di-$(C_1-C_6)$alkylaminosulphonyl, $(C_1-C_6)$alkylsulphoximino, aminothiocarbonyl, $(C_1-C_6)$alkylaminothiocarbonyl, di-$(C_1-C_6)$alkylaminothiocarbonyl, $(C_3-C_8)$cycloalkylamino, NHCO—$(C_1-C_6)$alkyl $((C_1-C_6)$alkylcarbonylamino), or where the substituents may independently be selected from phenyl or a 5- or 6-membered heteroaromatic ring, where phenyl or the ring may optionally be mono- or polysubstituted identically or differently by $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, NO$_2$, $C_1-C_4$-alkoxy, $C_1-C_4$-haloalkoxy, n is 0, 1 or 2, where, in the case of the structural unit A4, Q is none of the following ring systems:

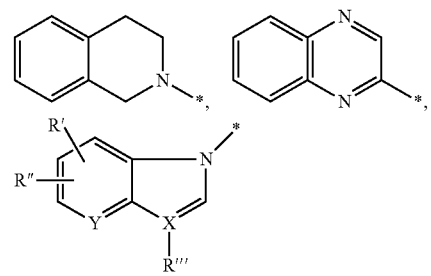

where X and Y, which may be the same or different, are carbon or nitrogen, R''' is hydrogen, aldehyde, oxime or —C(O)O—R$_a$, with the proviso that X is carbon, where R$_a$ is $C_1-C_6$-alkyl, R' and R'', which may be the same or different, are hydrogen, halogen, cyano, nitro, $C_1-C_6$-alkyl or $C_1-C_6$-alkoxy, and, in addition, when Aa is =C(H)—, in the case of the compounds of the formula (I), Q is not Q1, Q2, Q3, Q4, Q5, Q6, Q7, Q8, Q9, Q10, Q15, Q17.

DETAILED DESCRIPTION OF A PREFERRED EMBODIMENT

It has additionally been found that the compounds of the formula (I) or (I') have very good efficacy as pesticides, preferably as insecticides and/or acaricides, and additionally generally have very good plant compatibility, especially with respect to crop plants.

The compounds according to the invention are defined in general terms by the formula (I) or (I'). Preferred substituents or ranges for the radicals listed in the formulae mentioned above and below are illustrated hereinafter:

Configuration 2

Aa is preferably nitrogen or =C(R$^7$)—,
Ab is preferably nitrogen or =C(H)—,
Ac is preferably nitrogen or =C(H)—,
Ad is preferably nitrogen or =C(H)—,
Ae is preferably nitrogen or =C(H)—,
where Ab, Ac, Ad and Ae cannot all be nitrogen,
preferably resulting in the following structural units A1 to A44:

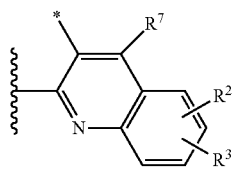
A1

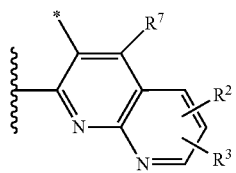
A2

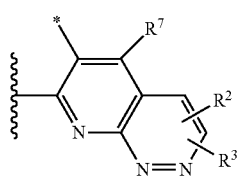
A3

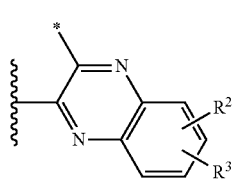
A4

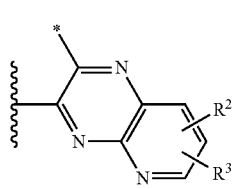
A5

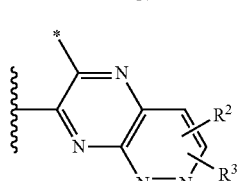
A6

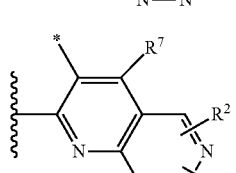
A7

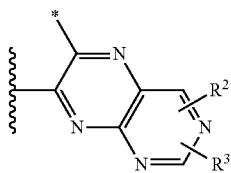
A8

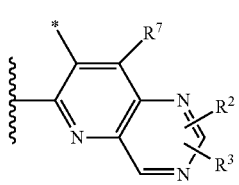
A9

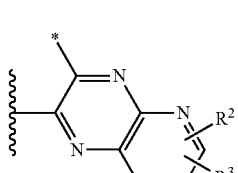
A10

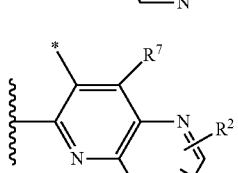
A11

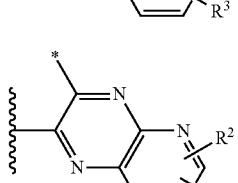
A12

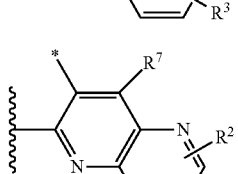
A13

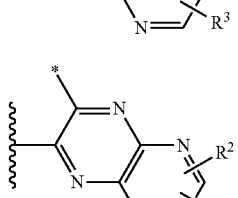
A14

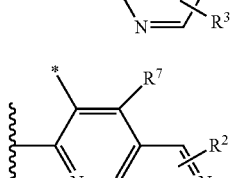
A15

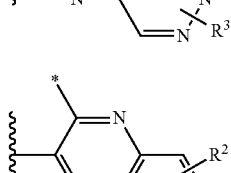
A16

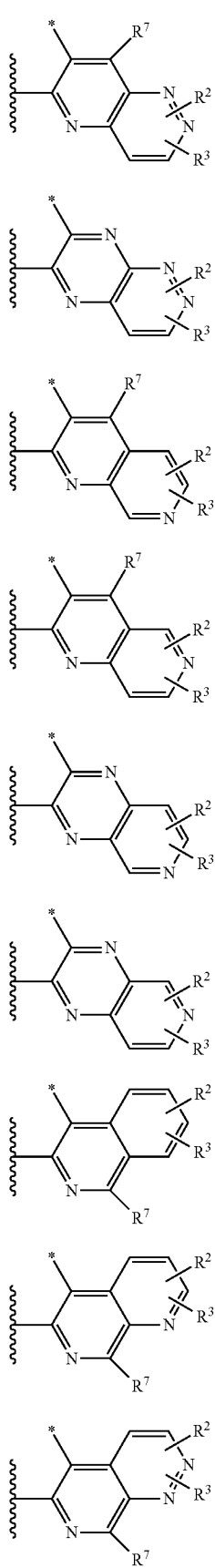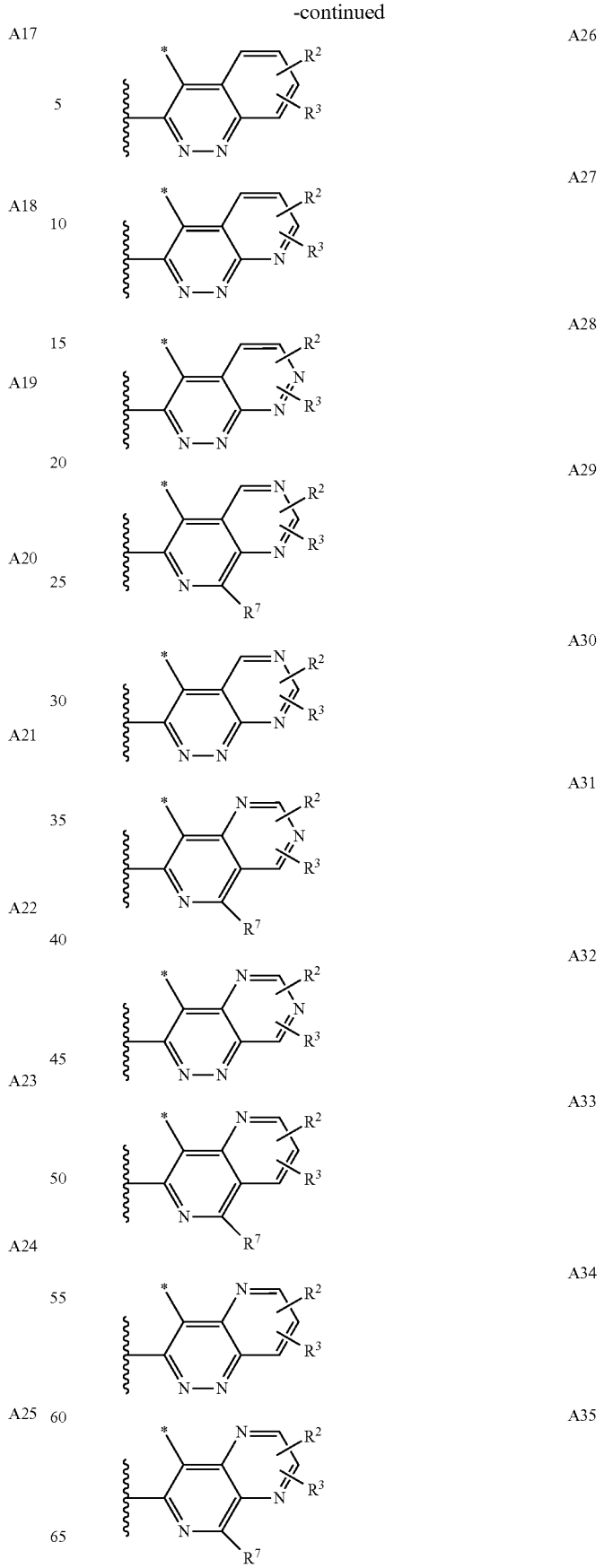

-continued

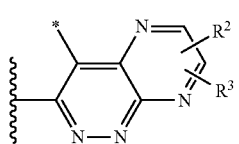
A36

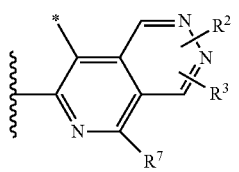
A37

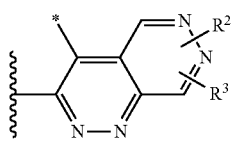
A38

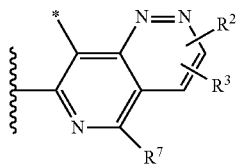
A39

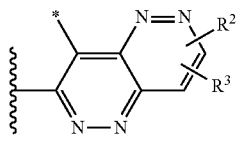
A40

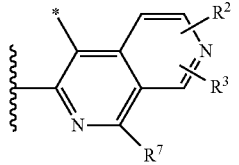
A41

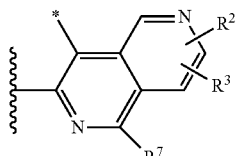
A42

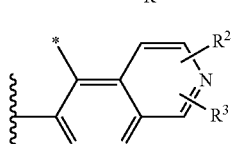
A43

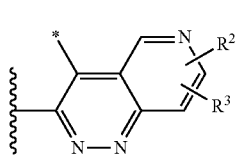
A44 where the bond to the substituent Q is identified by a wavy line and the bond to the sulphur atom by an asterisk *, $R^1$ is preferably $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl$(C_3-C_6)$cycloalkyl, $(C_1-C_4)$alkyl-$(C_3-C_6)$cycloalkyl, halo($C_3-C_6$)cycloalkyl, $(C_1-C_4)$alkylamino, di-$(C_1-C_4)$alkylamino, $(C_3-C_6)$cycloalkylamino, $(C_1-C_4)$alkylcarbonylamino, $(C_1-C_4)$alkylthio-$(C_1-C_4)$alkyl, $(C_1-C_4)$haloalkylthio-$(C_1-C_4)$alkyl, $(C_1-C_4)$alkylsulphinyl-$(C_1-C_4)$alkyl, $(C_1-C_4)$haloalkylsulphinyl-$(C_1-C_4)$alkyl, $(C_1-C_4)$alkylsulphonyl-$(C_1-C_4)$alkyl, $(C_1-C_4)$alkylcarbonyl-$(C_1-C_4)$alkyl, $(C_1-C_4)$haloalkylcarbonyl-$(C_1-C_4)$alkyl, $(C_1-C_4)$alkylsulphonylamino, or is $(C_1-C_4)$alkyl, $(C_1-C_4)$alkoxy, $(C_2-C_4)$alkenyl, $(C_2-C_4)$alkynyl, $(C_3-C_6)$cycloalkyl, each optionally mono- or disubstituted identically or differently by aryl, hetaryl and heterocyclyl, where aryl, hetaryl and heterocyclyl may each optionally be mono- or disubstituted identically or differently by halogen, cyano, carbamoyl, aminosulphonyl, $(C_1-C_4)$-alkyl, $(C_3-C_4)$cycloalkyl, $(C_1-C_4)$alkoxy, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$alkylsulphimino, or $R^1$ is preferably aryl, hetaryl or heterocyclyl, each optionally mono- or disubstituted identically or differently by halogen, cyano, carbamoyl, $(C_1-C_4)$alkyl, $(C_3-C_6)$cycloalkyl, $(C_1-C_4)$-alkoxy, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$alkylsulphimino, $(C_1-C_4)$alkylsulphoximino, $(C_1-C_4)$alkylcarbonyl, $(C_3-C_4)$trialkylsilyl, (=O) (in the case of heterocyclyl only) or $(=O)_2$ (in the case of heterocyclyl only), $R^2$, $R^3$ are preferably independently hydrogen, cyano, halogen, nitro, acetyl, hydroxyl, amino, SCN, tri($C_1-C_4$)alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo($C_3-C_6$)cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulphinyl, $(C_1-C_4)$haloalkylsulphinyl, $(C_1-C_4)$alkylsulphinyl-$(C_1-C_4)$alkyl, $(C_1-C_4)$alkylsulphonyl, $(C_1-C_4)$haloalkylsulphonyl, $(C_1-C_4)$alkylsulphonyl-$(C_1-C_4)$alkyl, $(C_1-C_4)$alkylsulphonyloxy, $(C_1-C_4)$alkylcarbonyl, $(C_1-C_4)$haloalkylcarbonyl, aminocarbonyl, aminothiocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl, di-$(C_1-C_4)$alkylaminosulphonyl, aminothiocarbonyl or NHCO—$(C_1-C_4)$alkyl ($(C_1-C_4)$alkylcarbonylamino), $R^7$ is preferably hydrogen, cyano, halogen, acetyl, hydroxyl, amino, $(C_3-C_6)$cycloalkyl, halo($C_3-C_6$)cycloalkyl, $(C_1-C_4)$alkyl, $(C_1-C_4)$haloalkyl, $(C_1-C_4)$cyanoalkyl, $(C_2-C_4)$alkenyl, $(C_2-C_4)$haloalkenyl, $(C_2-C_4)$alkynyl, $(C_2-C_4)$haloalkynyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl or $(C_1-C_4)$haloalkylsulphonyl, Q is preferably a heteroaromatic 8-, 9-, 10-, 11- or 12-membered fused bicyclic or tricyclic ring system, where the ring system is optionally mono- or polysubstituted identically or differently, and where the substituents may independently be selected from hydrogen, cyano, halogen, nitro, acetyl, hydroxyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_4$)alkyl, ($C_2$-$C_6$)haloalkynyl, ($C_1$-$C_6$)alkoxy, ($C_1$-$C_6$)haloalkoxy, ($C_1$-$C_6$)haloalkoxy-($C_1$-$C_6$)alkyl, ($C_2$-$C_6$)alkenyloxy-($C_1$-$C_6$)alkyl, ($C_2$-$C_6$)haloalkenyloxy-($C_1$-$C_6$)alkyl, ($C_1$-$C_6$)cyanoalkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkyl sulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylcarbonyl-($C_1$-$C_6$)alkyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), or where the substituents may independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n is preferably 0, 1 or 2, where, in the case of the structural unit A4, Q is none of the following ring systems:

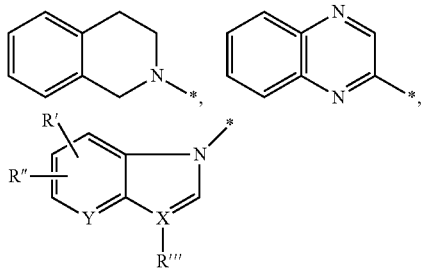

where X and Y, which may be the same or different, are carbon or nitrogen, R''' is hydrogen, aldehyde, oxime or —C(O)O—$R_a$, with the proviso that X is carbon, where $R_a$ is $C_1$-$C_6$-alkyl, R' and R'', which may be the same or different, are hydrogen, halogen, cyano, nitro, $C_1$-$C_6$-alkyl or $C_1$-$C_6$-alkoxy, and, in addition, when Aa is =C(H)—, in the case of the compounds of the formula (I), Q is not Q1, Q2, Q3, Q4, Q5, Q6, Q7, Q8, Q9, Q10, Q15, Q17.

Configuration 3-1

Aa is more preferably nitrogen or =C($R^7$)—,
Ab is more preferably nitrogen or =C(H)—,
Ac is more preferably nitrogen or =C(H)—,
Ad is more preferably nitrogen or =C(H)—,
Ae is more preferably nitrogen or =C(H)—,
where Ab, Ac, Ad and Ae cannot all be nitrogen, more preferably resulting in the following structural units:
A1, A2, A3, A4, A5, A7, A8, A9, A10, A11, A12, A13, A14, A15, A17, A19, A20, A21, A22, A23, A24, A25, A26, A27, A29, A30, A31, A32, A33, A34, A35, A36, A37, A39, A41, A42, A43, A44, $R^1$ is more preferably ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl or ($C_1$-$C_4$)alkylsulphonyl-($C_1$-$C_4$)alkyl, $R^2$, $R^3$ are more preferably independently hydrogen, cyano, halogen, nitro, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkyl sulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl or NHCO—($C_1$-$C_4$)alkyl (($C_1$-$C_4$)alkylcarbonylamino), $R^7$ is more preferably hydrogen, halogen, cyano, ($C_1$-$C_4$) alkyl or ($C_1$-$C_4$)haloalkyl, Q is more preferably a heteroaromatic 9-membered or 12-membered fused bicyclic or tricyclic ring system from the group of Q1 to Q20,

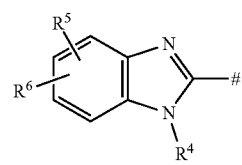

Q1

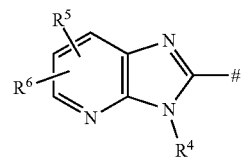

Q2

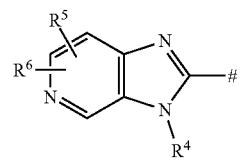

Q3

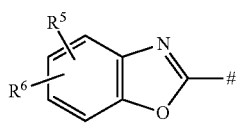 Q4

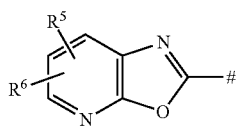 Q5

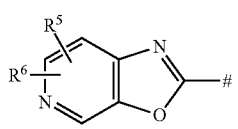 Q6

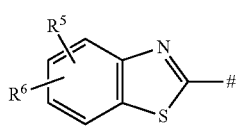 Q7

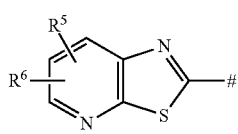 Q8

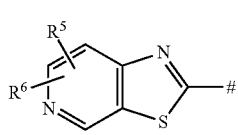 Q9

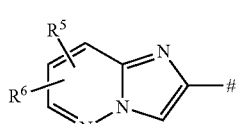 Q10

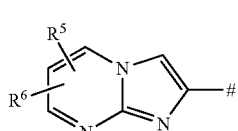 Q11

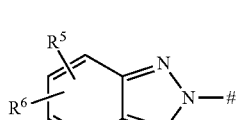 Q12

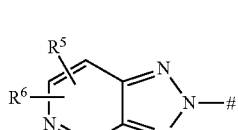 Q13

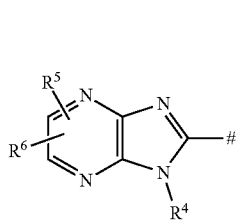 Q14

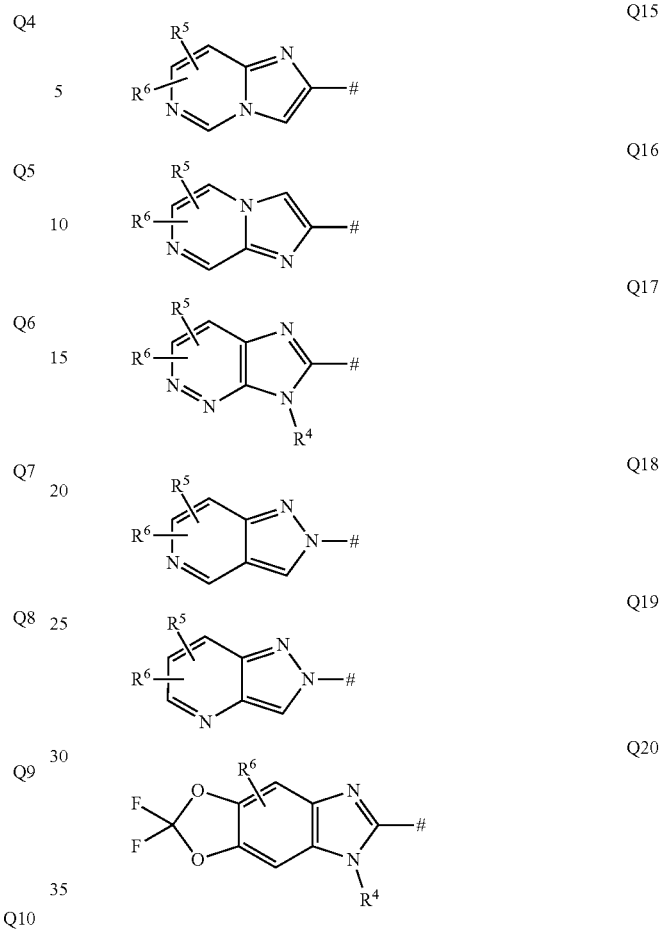

$R^4$ is more preferably $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, $R^5$, $R^6$ are more preferably independently hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkyl sulphinyl, $(C_1-C_4)$alkylsulphonyl, $(C_1-C_4)$haloalkyl sulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl or di-$(C_1-C_4)$alkylaminosulphonyl, n is more preferably 0, 1 or 2.

Configuration 3-2

Aa, Ab, Ac, Ad, Ae, $R^1$, $R^2$, $R^3$, $R^7$, Q, $R^5$, $R^6$ and n have the definitions given in configuration 3-1 and R[4] is more preferably hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, where, when Aa is =C(H)—, in the case of the compounds of the formula (I), Q is not Q1, Q2, Q3, Q4, Q5, Q6, Q7, Q8, Q9, Q10, Q15, Q17.

Configuration 4-1
Aa is even more preferably nitrogen or =C(R[7])—,
Ab is even more preferably nitrogen or =C(H)—,
Ac is even more preferably nitrogen or =C(H)—,
Ad is even more preferably nitrogen or =C(H)—,
Ae is even more preferably nitrogen or =C(H)—,
where Ab, Ac, Ad and Ae cannot all be nitrogen,
even more preferably resulting in the following structural units: A1, A2, A4, A5, A7, A9, A11, A12, A13, A19, A20, A21, A22, A23, A24, A26, A27, A29, A31, A33, A34, A35, A41, A42, A43, A44, R[1] is even more preferably $(C_1-C_4)$-alkyl, $(C_1-C_4)$haloalkyl or $(C_3-C_6)$cycloalkyl, R[2], R[3] are even more preferably independently hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$haloalkylthio, $(C_1-C_4)$haloalkylsulphinyl, $(C_1-C_4)$haloalkylsulphonyl or NHCO—$(C_1-C_4)$alkyl (($(C_1-C_4)$alkylcarbonylamino), R[7] is even more preferably hydrogen, halogen, cyano or $(C_1-C_4)$alkyl, Q is even more preferably a heteroaromatic 9-membered or 12-membered fused bicyclic or tricyclic ring system from the group of Q2, Q3, Q5, Q6, Q8, Q9, Q10, Q11, Q12, Q13, Q15, Q16, Q17, Q18, Q19 or Q20,

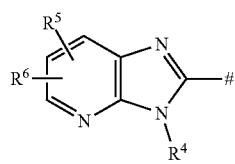
Q2

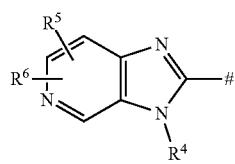
Q3

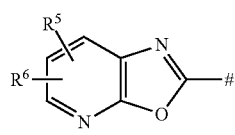
Q5

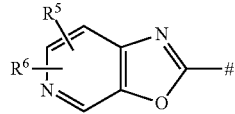
Q6

-continued

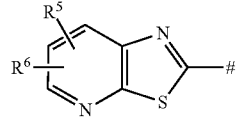
Q8

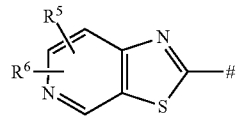
Q9

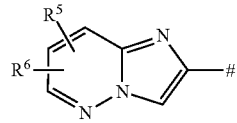
Q10

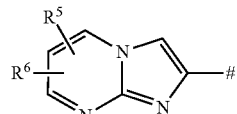
Q11

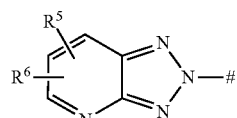
Q12

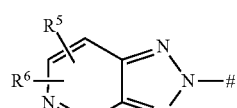
Q13

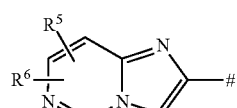
Q15

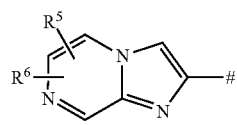
Q16

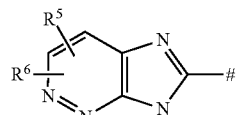
Q17

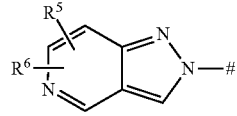
Q18

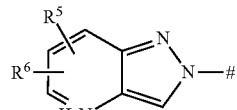
Q19

-continued

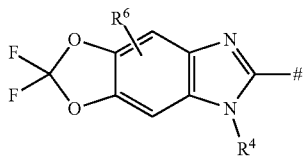
Q20

R⁴ is even more preferably (C₁-C₄)-alkyl or (C₁-C₄)-alkoxy-(C₁-C₄)-alkyl,

R⁵ is even more preferably hydrogen, cyano, halogen, (C₁-C₄)alkyl, (C₁-C₄)haloalkyl, (C₃-C₆)cycloalkyl, (C₃-C₆)cycloalkyl-(C₃-C₆)cycloalkyl, (C₁-C₄)alkyl-(C₃-C₆)cycloalkyl, (C₁-C₄)alkoxy, (C₁-C₄)haloalkoxy, (C₁-C₄)alkoxyimino, (C₁-C₄)alkylthio, (C₁-C₄)haloalkylthio, (C₁-C₄)alkylsulphinyl, (C₁-C₄)haloalkyl sulphinyl, (C₁-C₄)alkylsulphonyl, (C₁-C₄)haloalkyl sulphonyl, (C₁-C₄)alkylcarbonyl, (C₁-C₄)haloalkylcarbonyl, (C₁-C₄)alkylaminocarbonyl, di-(C₁-C₄)alkylaminocarbonyl, (C₁-C₄)alkylsulphonylamino, (C₁-C₄)alkylaminosulphonyl or di-(C₁-C₄)alkylaminosulphonyl, R⁶ is even more preferably hydrogen, n is even more preferably 0, 1 or 2.

Configuration 4-2

Aa, Ab, Ac, Ad, Ae, R¹, R⁵, R⁶ and n have the definitions given in configuration 4-1 and R², R³ are independently even more preferably hydrogen, cyano, halogen, (C₁-C₄)alkyl, (C₁-C₄)alkoxy, (C₁-C₄)haloalkyl, (C₁-C₄)haloalkoxy, (C₁-C₄)alkylthio, (C₁-C₄)alkylsulphinyl, (C₁-C₄)alkylsulphonyl, (C₁-C₄)haloalkylthio, (C₁-C₄)haloalkyl sulphinyl, (C₁-C₄)haloalkylsulphonyl or NHCO—(C₁-C₄)alkyl ((C₁-C₄)alkylcarbonylamino), R⁷ is even more preferably hydrogen, halogen, cyano, (C₁-C₄)alkyl or (C₁-C₄)haloalkyl, Q is even more preferably a heteroaromatic 9-membered or 12-membered fused bicyclic or tricyclic ring system from the group of Q1, Q2, Q3, Q5, Q6, Q8, Q9, Q10, Q11, Q12, Q13, Q15, Q16, Q17, Q18, Q19 or Q20, R⁴ is even more preferably hydrogen, (C₁-C₄)alkyl or (C₁-C₄)-alkoxy-(C₁-C₄)alkyl, where, when Aa is =C(H)—, in the case of the compounds of the formula (I), Q is not Q1, Q2, Q3, Q5, Q6, Q8, Q9, Q10, Q15, Q17.

Configuration 5-1

Aa is specifically nitrogen or =C(R⁷)—,
Ab is specifically nitrogen or =C(H)—,
Ac is specifically nitrogen or =C(H)—,
Ad is specifically nitrogen or =C(H)—,
Ae is specifically nitrogen or =C(H)—,
where Ab, Ac, Ad and Ae cannot all be nitrogen, specifically resulting in the following structural units: A1, A2, A4, A11, A13, A19, A20, A23, A24, A26, A33, A35, A41, A42, R¹ is specifically methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R², R³ are independently specifically hydrogen, fluorine, chlorine, bromine, iodine, cyano, methyl, ethyl, methoxy, trifluoromethyl, trifluoromethoxy or trifluoromethylthio, R⁷ is specifically hydrogen, fluorine, chlorine, bromine, cyano, methyl, ethyl or trifluoromethyl, Q is specifically a hetero aromatic 9-membered fused bicyclic ring system from the group of Q2, Q3, Q10, Q15 and Q17

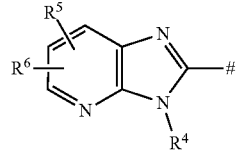
Q2

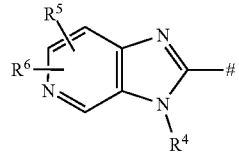
Q3

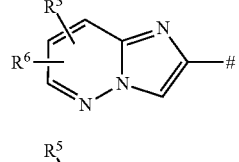
Q10

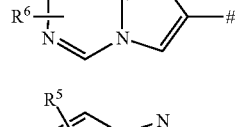
Q15

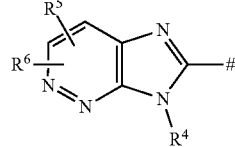
Q17

R⁴ is specifically methyl, ethyl, isopropyl, methoxymethyl or methoxyethyl,

R⁵ is specifically fluorine, chlorine, bromine, fluoromethyl, difluoromethyl, trifluoromethyl, fluoroethyl (CH₂CFH₂, CHFCH₃), difluoroethyl (CF₂CH₃, CH₂CHF₂, CHFCFH₂), trifluoroethyl (CH₂CF₃, CHFCHF₂, CF₂CFH₂), tetrafluoroethyl (CHFCF₃, CF₂CHF₂), pentafluoroethyl, trifluoromethoxy, difluorochloromethoxy, dichlorofluoromethoxy or trifluoromethylthio, R⁶ is specifically hydrogen, n is specifically 0, 1 or 2.

Configuration 5-2

Aa is specifically nitrogen or =C(R⁷)—,
Ab is specifically =C(H)—,
Ac is specifically =C(H)—,
Ad is specifically =C(H)—,
Ae is specifically nitrogen or =C(H)—, specifically resulting in the following structural units: A1, A4, A23, A26, A33, R¹ is specifically methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R², R³ are independently specifically hydrogen, fluorine, chlorine, bromine, iodine, cyano, methyl, ethyl, methoxy, trifluoromethyl, trifluoromethoxy or trifluoromethylthio, R⁷ is specifically hydrogen, fluorine, chlorine, bromine, cyano, methyl, ethyl or trifluoromethyl, Q is specifically a heteroaromatic 9-membered or 12-membered fused bicyclic ring system from the group of Q1, Q2, Q3, Q16, Q17 or Q20, $R^4$ is specifically hydrogen, methyl, ethyl, isopropyl, methoxymethyl or methoxyethyl, $R^5$ is specifically fluorine, chlorine, bromine, fluoromethyl, difluoromethyl, trifluoromethyl, fluoroethyl ($CH_2CFH_2$, $CHFCH_3$), difluoroethyl ($CF_2CH_3$, $CH_2CHF_2$, $CHFCFH_2$), trifluoroethyl, ($CH_2CF_3$, $CHFCHF_2$, $CF_2CFH_2$), tetrafluoroethyl ($CHFCF_3$, $CF_2CHF_2$), pentafluoroethyl, trifluoromethoxy, difluorochloromethoxy, dichlorofluoromethoxy, trifluoromethylthio, trifluoromethylsulphinyl or trifluoromethylsulphanyl, $R^6$ is specifically hydrogen, n is specifically 0, 1 or 2, where, when Aa is =C(H)—, in the case of the compounds of the formula (I), Q is not Q1, Q2, Q3, Q17.

Configuration 6-1

Aa is especially nitrogen or =C($R^7$)—,
Ab is especially =C(H)—,
Ac is especially =C(H)—,
Ad is especially =C(H)—,
Ae is especially =C(H)—,
especially resulting in the following structural units: A1 or A4,
$R^1$ is especially ethyl,
$R^2$, $R^3$ are especially hydrogen,
$R^7$ is especially hydrogen,
Q is especially a heteroaromatic 9-membered fused bicyclic ring system from the group of Q3

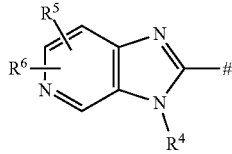

Q3

$R^4$ is especially methyl,
$R^5$ is especially trifluoromethyl,
$R^6$ is especially hydrogen,
n is especially 0 or 2.

Configuration 6-2

Aa is especially nitrogen or =C($R^7$)—,
Ab is especially =C(H)—,
Ac is especially =C(H)—,
Ad is especially =C(H)—,
Ae is especially nitrogen or =C(H)—,
especially resulting in the following structural units: A1, A4, A23, A26, A33
$R^1$ is especially methyl or ethyl,
$R^2$ is especially hydrogen, chlorine, methoxy or trifluoromethyl,
$R^3$ is especially hydrogen,
$R^7$ is especially hydrogen,
Q is especially a heteroaromatic 9-membered or 12-membered fused bicyclic ring system from the group of Q1, Q2, Q3, Q16, Q17, Q20,
$R^4$ is especially hydrogen or methyl,
$R^5$ is especially trifluoromethyl or pentafluoroethyl,
$R^6$ is especially hydrogen,
n is especially 0, 1 or 2,
where, when Aa is =C(H)—, in the case of the compounds of the formula (I), Q is not Q1, Q2, Q3, Q17.

Configuration 6-3

Aa is especially nitrogen or =C($R^7$)—,
Ab is especially =C(H)—,
Ac is especially =C(H)—,
Ad is especially =C(H)—,
Ae is especially nitrogen or =C(H)—,
preferably resulting especially in the following structural units: A23, A26, A33,
$R^1$ is especially methyl or ethyl,
$R^2$ is especially hydrogen or trifluoromethyl,
$R^3$ is especially hydrogen,
$R^7$ is especially hydrogen,
Q is especially a ring system from the group of Q1, Q2, Q3, Q17,
$R^4$ is especially methyl,
$R^5$ is especially trifluoromethyl or pentafluoroethyl,
$R^6$ is especially hydrogen,
n is especially 0, 1 or 2,
where, when Aa is =C(H)—, in the case of the compounds of the formula (I), Q is not Q1, Q2, Q3, Q17.

With inclusion of structural units A1 to A44, this results in the following principal structures of the formula (I) or formula (I'):

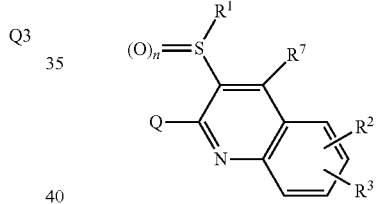

I(A1)

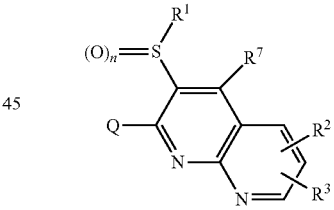

I(A2)

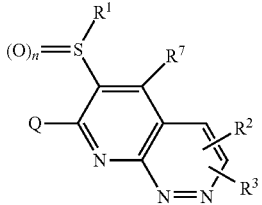

I(A3)

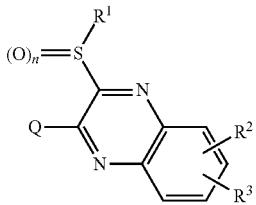

I(A4)

I(A5)
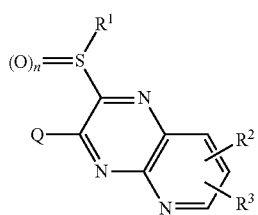
I(A6)
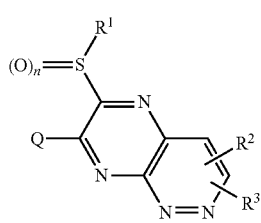
I(A7)
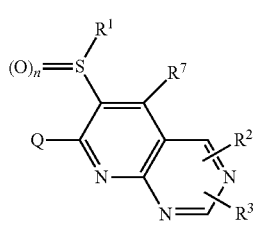
I(A8)
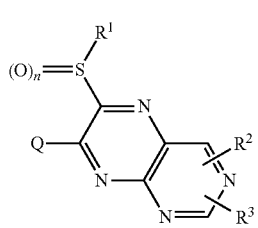
I(A9)
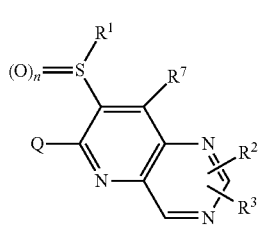
I(A10)
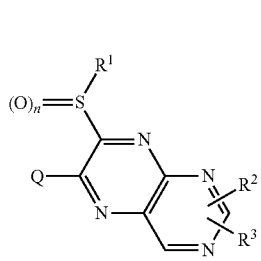
I(A11)
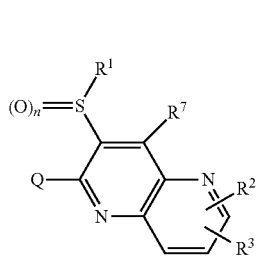
I(A12)
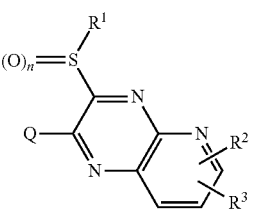
I(A13)
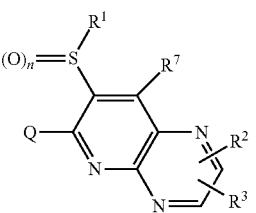
I(A14)
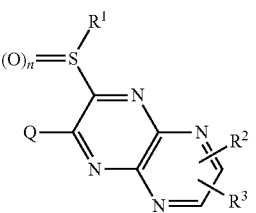
I(A15)
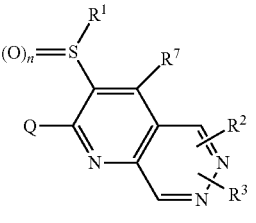
I(A16)
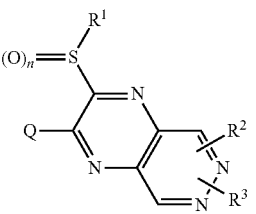
I(A17)
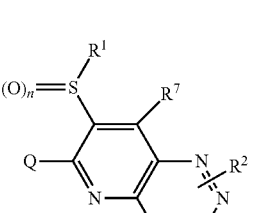
I(A18)
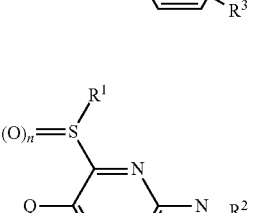

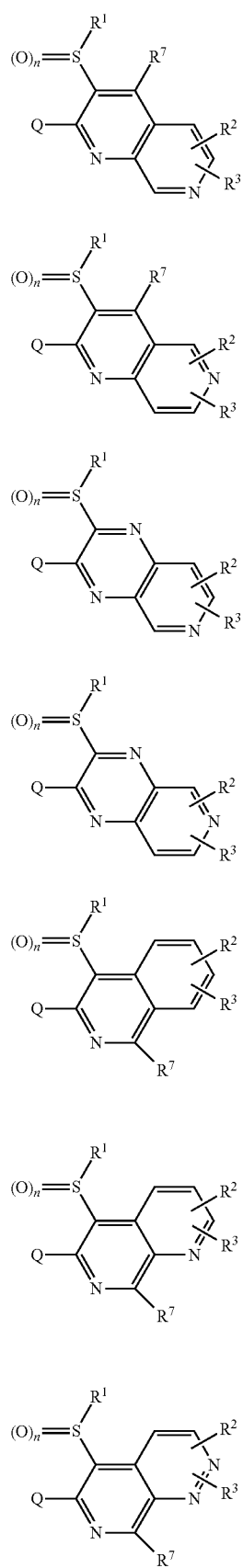
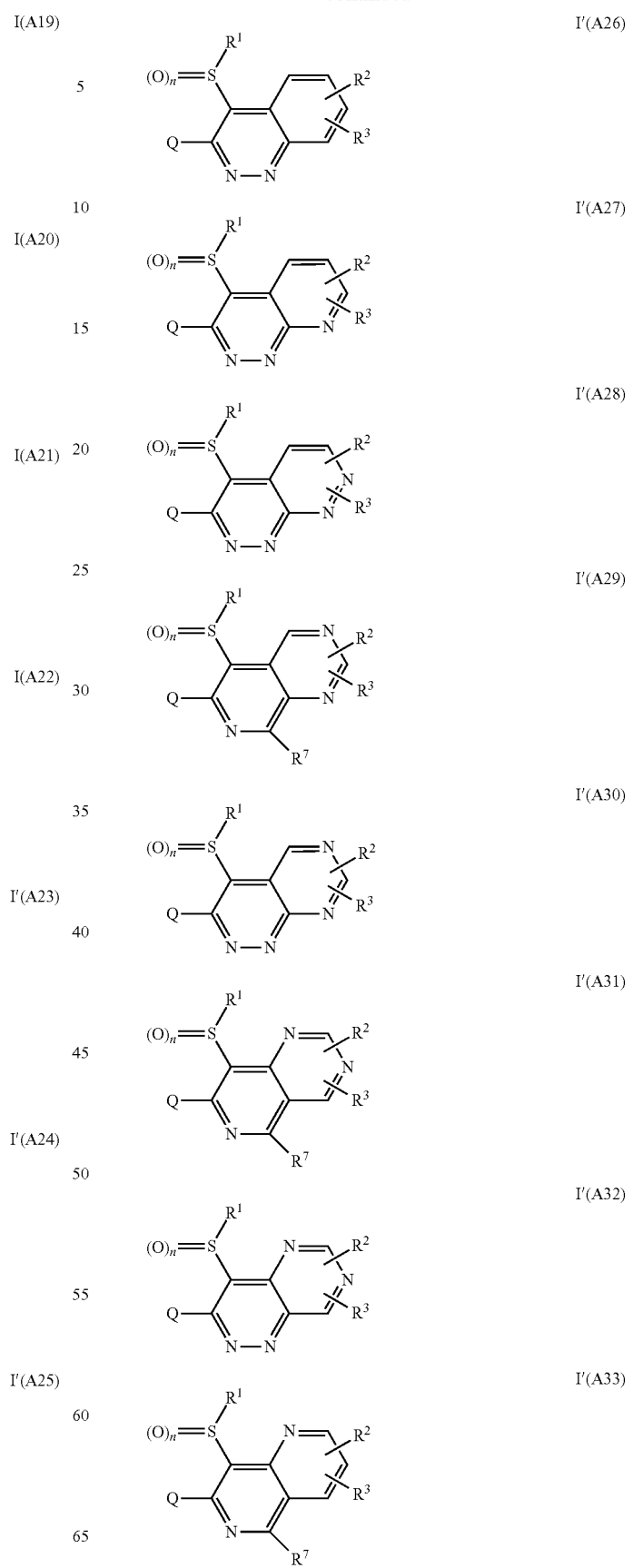

I'(A34) 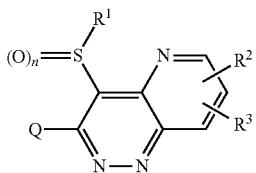

I'(A35) 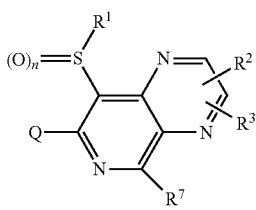

I'(A36) 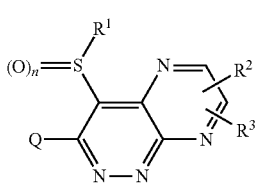

I'(A37) 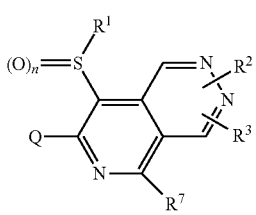

I'(A38) 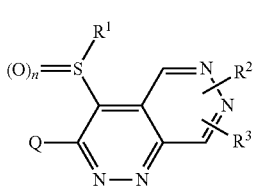

I'(A39) 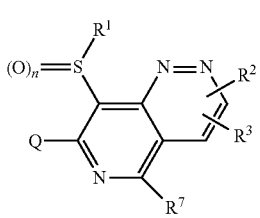

I'(A40) 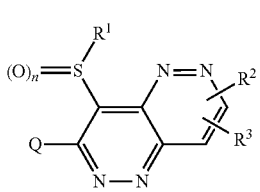

I'(A41) 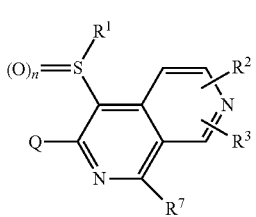

I'(A42) 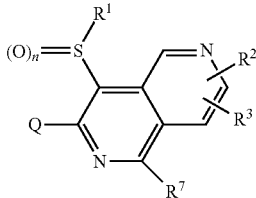

I'(A43) 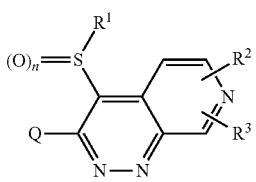

I'(A44) 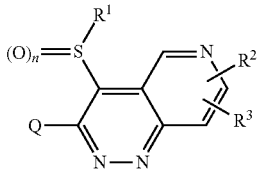

where $R^1$, $R^2$, $R^3$, $R^2$, Q and n have the definitions given above.

In a preferred embodiment, the invention relates to compounds of the formula (I) where $R^1$, $R^2$, $R^3$, $R^2$, Q, Aa, Ab, Ac, Ad, Ae and n have the definitions given in configuration (1) or configuration (2).

In a preferred embodiment, the invention relates to compounds of the formula (I) where $R^1$, $R^2$, $R^3$, $R^4$, $R^5$, $R^6$, $R^7$, Q, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where $R^1$, $R^2$, $R^3$, $R^7$, Q, Aa, Ab, Ac, Ad, Ae and n have the definitions given in configuration (1) or configuration (2).

In a preferred embodiment, the invention relates to compounds of the formula (I') where $R^1$, $R^2$, $R^3$, $R^4$, $R^5$, $R^6$, $R^7$, Q, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q1 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q2 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q3 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q4 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q5 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q6 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q7 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q8 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q9 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q10 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q11 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q12 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q13 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q14 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q15 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q16 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q17 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q18 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q19 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) where Q is Q20 and $R^1$, $R^2$, $R^3$, $R^4$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q1 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q2 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q3 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q4 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q5 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q6 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q7 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q8 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q9 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q10 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q11 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q12 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q13 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q14 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q15 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q16 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q17 and $R^1$, $R^2$, $R^3$, $R^4$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q18 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q19 and $R^1$, $R^2$, $R^3$, $R^5$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where Q is Q20 and $R^1$, $R^2$, $R^3$, $R^4$, $R^6$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) with the structural unit A1 and where Q is Q16 or Q20 and $R^1$, $R^2$, $R^3$, $R^4$, $R^5$, $R^6$, $R^7$ and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) with the structural unit A4 and where Q, $R^1$, $R^2$, $R^3$, $R^4$, $R^5$, $R^6$ and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) with the structural unit A23 and where Q, $R^1$, $R^2$, $R^3$, $R^4$, $R^5$, $R^6$, $R^7$ and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) with the structural unit A26 and where Q, $R^1$, $R^2$, $R^3$, $R^4$, $R^5$, $R^6$ and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I) with the structural unit A33 and where Q, $R^1$, $R^2$, $R^3$, $R^4$, $R^5$, $R^6$, $R^7$ and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In a preferred embodiment, the invention relates to compounds of the formula (I') where
Aa is nitrogen or =C($R^7$)—,
Ab is =C(H)—,
Ac is =C(H)—,
Ad is =C(H)—,
Ae is nitrogen or =C(H)—,
preferably resulting in the following structural units: A23, A26, A33,
$R^1$ is methyl or ethyl,
$R^2$ is hydrogen or trifluoromethyl,
$R^3$ is hydrogen,
$R^7$ is hydrogen,
Q is a ring system from the group of Q1, Q2, Q3, Q17,
$R^4$ is methyl,
$R^5$ is trifluoromethyl or pentafluoroethyl,
$R^6$ is hydrogen,
n is 0, 1 or 2.

In a preferred embodiment, the invention relates to compounds of formula (I) or (I') where Q is the following ring systems:

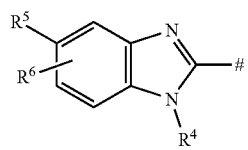
Q1a

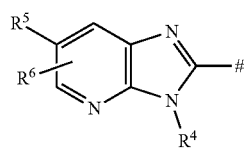
Q2a

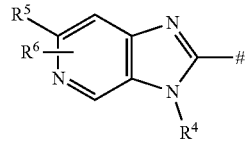
Q3a

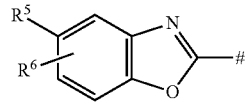
Q4a

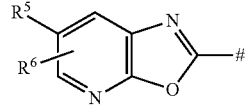
Q5a

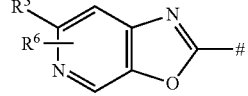
Q6a

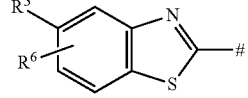
Q7a

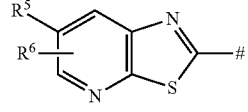
Q8a

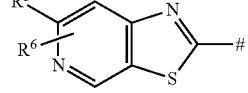
Q9a

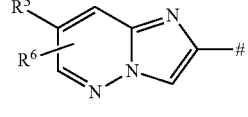
Q10a

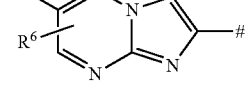
Q11a

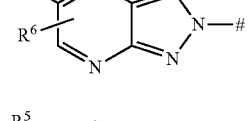
Q12a

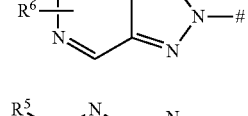
Q13a

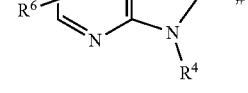
Q14a

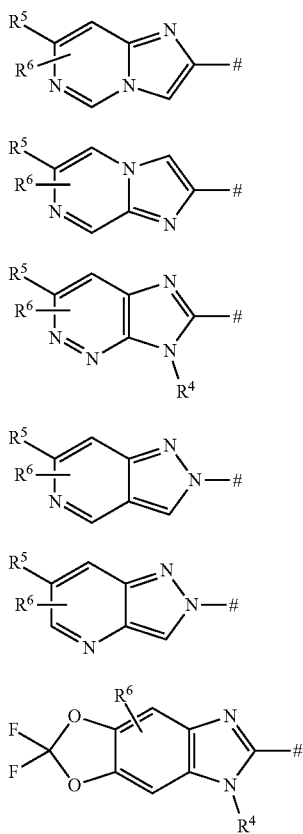

where $R^6$ is hydrogen and $R^1$, $R^2$, $R^3$, $R^4$, $R^5$, $R^7$, Aa, Ab, Ac, Ad, Ae and n have the definitions given in configuration (3-1) or configuration (3-2) or configuration (4-1) or configuration (4-2) or configuration (5-1) or configuration (5-2) or configuration (6-1) or configuration (6-2) or configuration (6-3).

In the preferred definitions, unless stated otherwise, halogen is selected from the group of fluorine, chlorine, bromine and iodine, preferably in turn from the group of fluorine, chlorine and bromine, In the particularly preferred definitions, unless stated otherwise, halogen is selected from the group of fluorine, chlorine, bromine and iodine, preferably in turn from the group of fluorine, chlorine and bromine, In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. In this case, halogen is fluorine, chlorine, bromine or iodine, especially fluorine, chlorine or bromine.

Unless stated otherwise, optionally substituted radicals may be mono- or polysubstituted, where the substituents in the case of polysubstitutions may be the same or different.

The radical definitions or elucidations given above in general terms or within areas of preference apply to the end products and correspondingly to the starting materials and intermediates. These radical definitions can be combined with one another as desired, i.e. including combinations between the respective ranges of preference.

Preference is given in accordance with the invention to using compounds of the formula (I) or (I') in which a combination of the definitions listed above as being preferred is present.

Particular preference is given in accordance with the invention to using compounds of the formula (I) or (I') in which a combination of the definitions listed above as being more preferred is present.

Very particular preference is given in accordance with the invention to using compounds of the formula (I) or (I') in which a combination of the definitions listed above as being even more preferred is present.

Specific preference is given in accordance with the invention to using compounds of the formula (I) or (I') in which a combination of the definitions listed above as being specifically preferred is present.

Especial preference is given in accordance with the invention to using compounds of the formula (I) or (I') in which a combination of the definitions listed above as being especially preferred is present.

Depending on the nature of the substituents, the compounds of the formula (I) or (I') may be in the form of geometric and/or optically active isomers or corresponding isomer mixtures in different compositions.

These stereoisomers are, for example, enantiomers, diastereomers, atropisomers or geometric isomers. The invention therefore encompasses pure stereoisomers and any desired mixtures of these isomers.

The compounds of the formula (I) or (I') according to the invention can be obtained by the processes shown in the following schemes:

Process A-1

The compounds of the formula (I) in which Q is Q1 to Q9 or Q20 can be prepared by known methods, for example analogously to the processes described in WO2009/131237, WO2010/125985, WO2011/043404, WO2011/040629, WO2012/086848, WO2013/018928, WO2015/000715, WO2015/198859, WO2016/039444, WO2016/039441, WO2016/116338 and WO2015/121136.

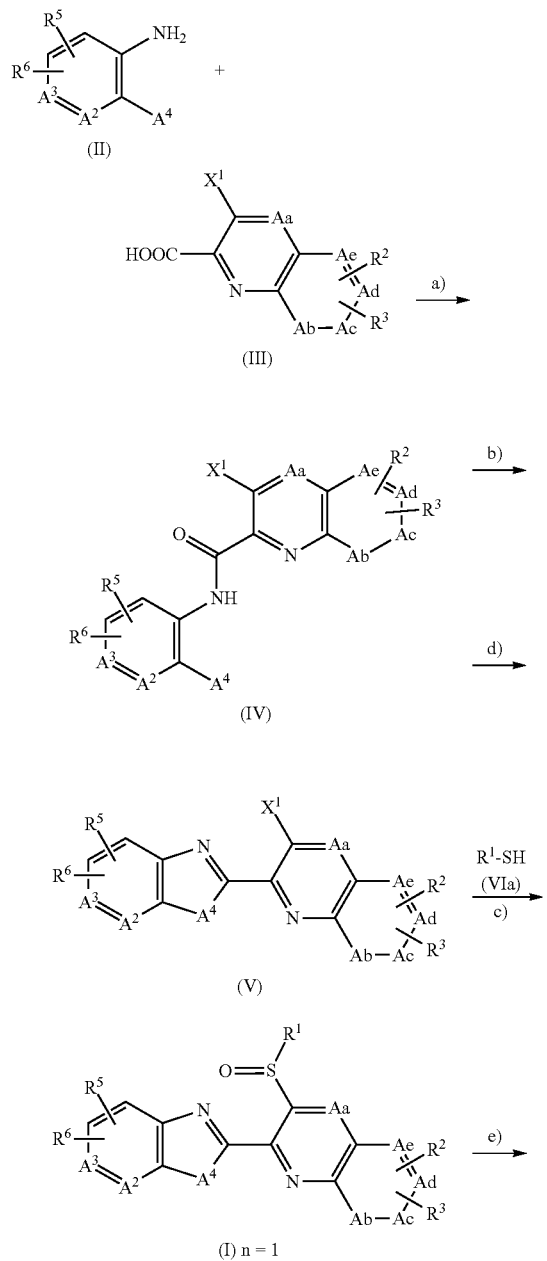

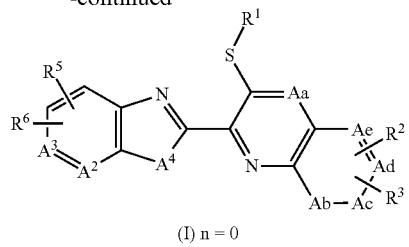

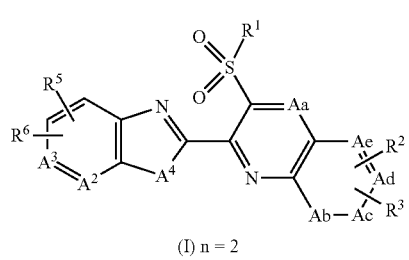

The radicals $R^1$, $R^2$, $R^3$, $R^4$, $R^5$, $R^6$, Aa, Ab, Ac, Ad, Ae and n have the definitions described above, $A^2$ and $A^3$ are CH or N (where $A^2$ and $A^3$ may not both be N), $A^4$ is O—H, S—H or N(H)$R^4$, $A^4$ may also be chlorine, and $X^1$ is halogen.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent or a base.

Compounds of the formula (II) are either commercially available or can be prepared by known methods, for example analogously to the processes described in US2003/69257, WO2006/65703, WO2009/131237, WO2010/125985, WO2011/043404, WO2011/040629, WO2012/086848, WO2013/018928 or WO2015/000715.

Carboxylic acids of the formula (III) are either commercially available or can be prepared by known methods. Possible preparation routes are described in process F.

The reaction of the compounds of the formula (II) with carboxylic acids of the formula (III) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen-containing compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be effected under reduced pressure, at standard pressure or under elevated pressure and at temperatures of 0° C. to 180° C.; with preference, the reaction is carried out at standard pressure and temperatures of 20 to 140° C.

Step b)

The compounds of the formula (V) can be prepared by condensing the compounds of the formula (IV), for example analogously to the processes described in WO2009/131237, WO2010/125985, WO2011/043404, WO2011/040629, WO2012/086848, WO2013/018928, WO2015/000715 and WO2015/121136.

The conversion to compounds of the formula (V) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be conducted in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

Step c)

The compounds of the formula (I) where n represents 0 can be prepared by reacting the compounds of the formula (V) with the compounds of the formula (VIa) in the presence of a base.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (I) where n is 0 can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

Alternatively, it is possible to directly use the salts of the mercaptan derivatives, for example sodium ethanethiolate, sodium methanethiolate or sodium isopropanethiolate, without addition of further base. The reaction can be conducted under reduced pressure, at standard pressure or under elevated pressure, and at temperatures of 0° C. to 200° C.

In the reaction described, $X^1$ is preferably a fluorine or chlorine atom.

If $R^2$ or $R^3$ is likewise halogen (for example chlorine or fluorine), for example with use of methyl mercaptan, ethyl mercaptan or isopropyl mercaptan, it is also possible for multiple exchange with the alkyl mercaptan to take place as well as the single substitution of $X^1$.

Step d)

The compounds of the formula (I) where n is 1 can be prepared by oxidizing the compounds of the formula (I) where n is 0. The oxidation is generally conducted in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be conducted under reduced pressure, at standard pressure or under elevated pressure, and at temperatures of −20° C. to 120° C.

Step e)

The compounds of the formula (I) where n is 2 can be prepared by oxidizing the compounds of the formula (I) where n is 1. The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

Step f)

The compounds of the formula (I) where n is 2 can also be prepared in a one-step process by oxidizing the compounds of the formula (I) where n is 0. The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of −20° C. to 120° C.

The compounds of the formula (I') in which Q is Q1 to Q9 or Q20 can likewise be prepared analogously to process A-1, proceeding from the corresponding carboxylic acids of the formulae (III'$^{-A}$) or (III'$^{-B}$), the possible preparation routes for which are described in processes G and H.

If $R^2$ or $R^3$ is likewise alkylsulphanyl, it is possible with use of a suitable oxidizing agent, for example hydrogen peroxide and meta-chloroperbenzoic acid, as well as the oxidation of the sulphur atom alongside $R^1$ to the sulphone, for oxidation of the alkylsulphanyl substituent to alkylsulphonyl to take place in addition.

Process A-2

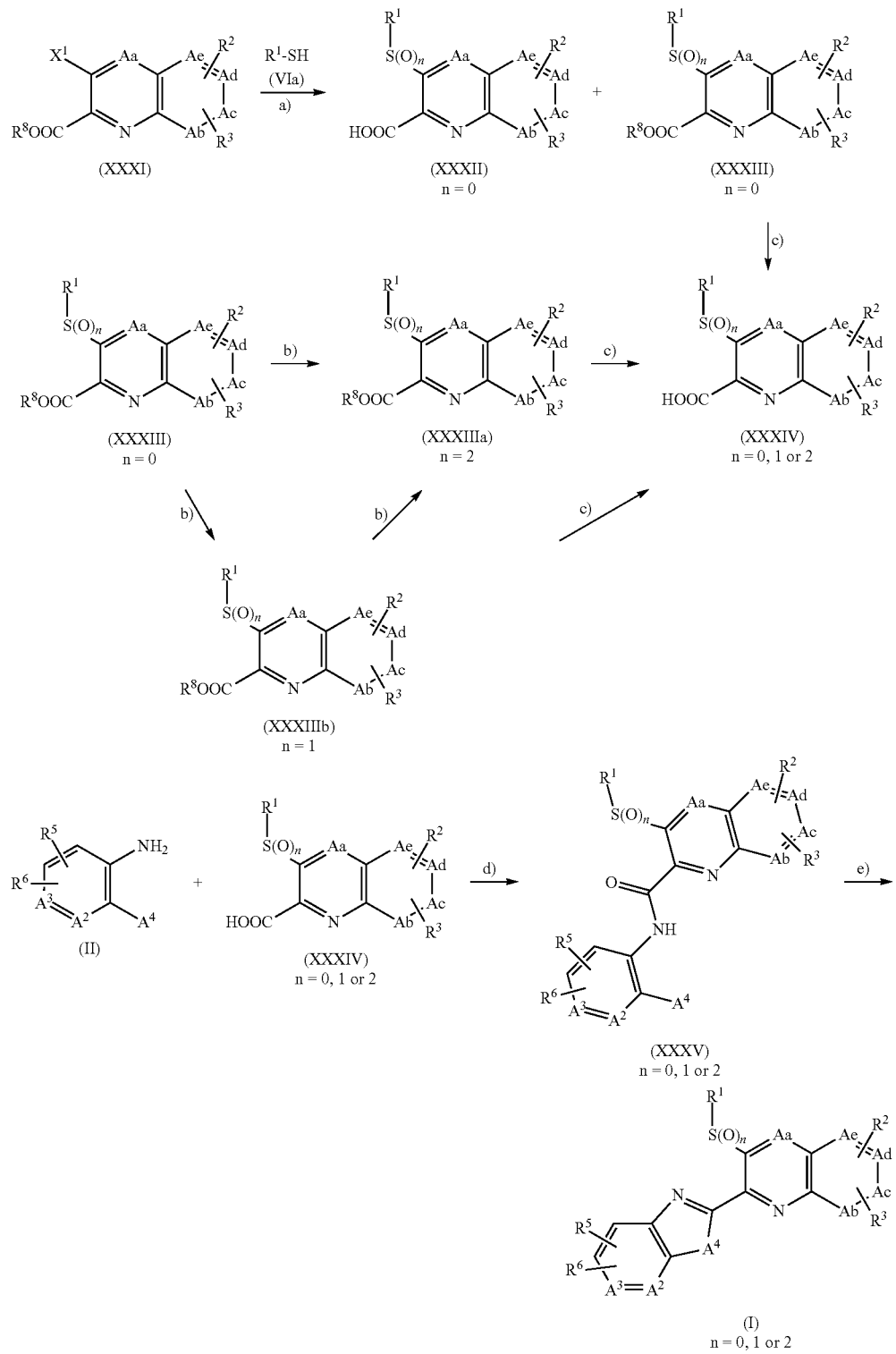

The radicals Aa, Ab, Ac, Ad, Ae, $R^1$, $R^2$, $R^3$, $R^5$, $R^6$ and n have the definitions described above, $A^2$ and $A^3$ are CH or N, $X^1$ is halogen, $A^4$ is O—H, S—H or N(H)$R^4$, $A^4$ may also be chlorine, and $R^8$ is ($C_1$-$C_4$)alkyl.

Step a)

The compounds of the formulae (XXXII) and (XXXIII) can be prepared by reacting the compounds of the formula (XXXI) with the compounds of the formula (VIa) in the presence of a base.

The compounds of the formula (XXXI) are either commercially available or can be prepared by known methods, for example from 2-aminopyridine derivatives analogously to the processes described in WO2011/41713 or in analogy to processes F-1 and F-2.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formulae (XXXII) and (XXXIII) can be effected neat or in a solvent; preferably, the reaction is conducted in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

Alternatively, it is possible to directly use the salts of the mercaptan derivatives, for example sodium ethanethiolate, sodium methanethiolate or sodium isopropanethiolate, without addition of further base.

The reaction can be conducted under reduced pressure, at standard pressure or under elevated pressure, and at temperatures of 0° C. to 200° C.

Step b)

The compounds of the formula (XXXIIIb) can be prepared by oxidizing the compounds of the formula (XXXIII). The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be conducted under reduced pressure, at standard pressure or under elevated pressure, and at temperatures of –20° C. to 120° C.

The compounds of the formula (XXXIIIa) can be prepared analogously by oxidizing the compounds of the formula (XXXIII).

The compounds of the formula (XXXIIIa) can be prepared analogously by oxidizing the compounds of the formula (XXXIIIb).

Step c)

The compounds of the formula (XXXIV) where n is 2 can be prepared by hydrolysing the compounds of the formula (XXXIIIa) in the presence of a base. The hydrolysis is generally conducted in a solvent. Preference is given to alcohols such as methanol or ethanol; water; ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide; or mixtures of the solvents mentioned.

Examples of suitable bases are inorganic bases from the group consisting of acetates, phosphates and carbonates of alkali metals or alkaline earth metals. Preference is given here to caesium carbonate, sodium carbonate and potassium carbonate.

The reaction can be conducted under reduced pressure, at standard pressure or under elevated pressure, and at temperatures of –20° C. to 200° C.

The compounds of the formula (XXXIV) where n is 0 can analogously be prepared by hydrolysing the compounds of the formula (XXXIII).

The compounds of the formula (XXXIV) where n is 1 can analogously be prepared by hydrolysing the compounds of the formula (XXXIIIb).

The further conversion of compounds of the formula (XXXIV) to compounds of the formula (I) is carried out analogously to process A-1.

Step d)

The compounds of the formula (XXXV) can be prepared by the reaction of compounds of the formula (II) with carboxylic acids of the formula (XXXIV) in the presence of a condensing agent or a base.

The compounds of the formula (II) are either commercially available or can be prepared by known methods, for example analogously to the processes described in US2003/069257, US2012/0319050, WO2011/107998 or WO2010/91310.

The reaction of the compounds of the formula (II) with carboxylic acids of the formula (XXXIV) where n is 0, 1 or 2 can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen-containing compounds, for example pyridine.

Suitable condensing agents are, for example, carbodiimides such as 1-(3-dimethylaminopropyl)-3-ethylcarbodiimide hydrochloride (EDCI), 1,3-dicyclohexylcarbodiimide, thionyl chloride or oxalyl chloride.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate. Further suitable bases are alkali metal hydrides, for example sodium hydride.

The reaction can be effected under reduced pressure, at standard pressure or under elevated pressure and at temperatures of 0° C. to 180° C.; with preference, the reaction is carried out at standard pressure and temperatures of 20 to 140° C.

Step e)

The compounds of the formula (I) where n is 0, 1 or 2 can be prepared by condensing the compounds of the formula (XXXV) in the presence of a base.

The conversion to compounds of the formula (I) where n is 0, 1 or 2 can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be conducted under reduced pressure, at standard pressure or under elevated pressure, and at temperatures of 0° C. to 200° C.

The compounds of the formula (I') in which Q is Q1 to Q9 or Q20 can likewise be prepared analogously to process A-2.

Process B

The compounds of the formula (I) in which Q represents Q10, Q11, Q15 or Q16 can be prepared by known methods, for example analogously to the processes described in US2009/203705, US2012/258951, WO2013/3298, WO2016/071214 or J. Med. Chem. 31, (1988) 1590-1595.

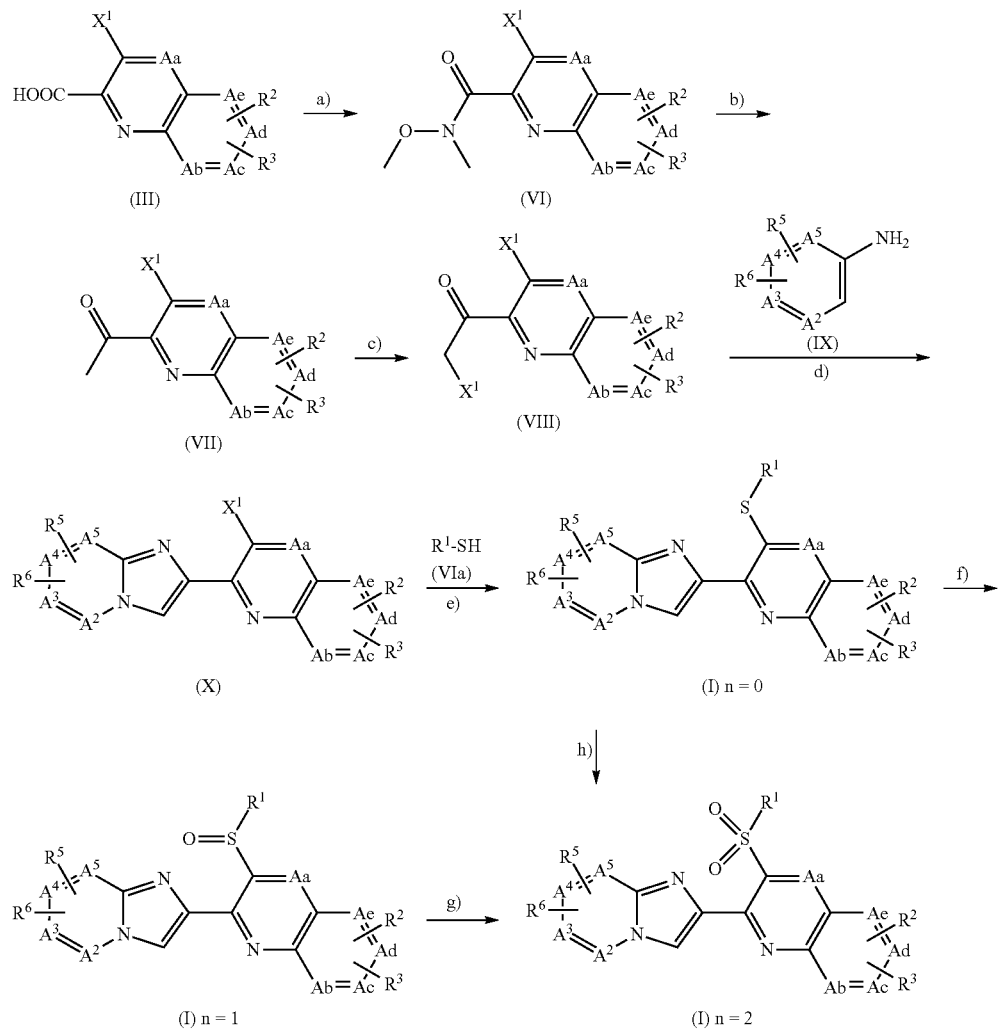

The radicals $R^1$, $R^2$, $R^3$, $R^5$, $R^6$, Aa, Ab, Ac, Ad, Ae and n have the definitions described above. $A^2$, $A^3$, $A^4$ and $A^5$ are CH or N (where $A^2$, $A^3$, $A^4$ and $A^5$ are not all N) and $X^1$ is halogen.

Step a)

Carboxylic acids of the formula (III) are converted in analogy to the process described in WO2011/75643 or EP2671582 in the presence of O,N-dimethylhydroxylamine hydrochloride to Weinreb amides of the formula (VI).

Carboxylic acids of the formula (III) are either commercially available or can be prepared by known methods. Possible preparation routes are described in process F.

Step b, c)

Compounds of the formula (VI) can then be converted by known methods, for example in analogy to the process described in WO2011/75643, with a Grignard reagent, for example methylmagnesium bromide, to ketones of the formula (VII). Compounds of the formula (VIII) are obtainable by subsequent halogenation analogously, for example, to the known method described in US2012/302573.

Step d)

The compounds of the formula (X) can be prepared by cyclizing the compounds of the formula (VIII) with amines of the formula (IX). The cyclization is effected, for example, in ethanol, acetonitrile or N,N-dimethylformamide by known methods in analogy, for example, to the processes described in WO2005/66177, WO2012/88411, WO2013/3298, US2009/203705, US2012/258951, WO2012/168733, WO2014/187762 or J. Med. Chem. 31 (1988) 1590-1595.

The compounds of the formula (IX) are commercially available.

Step e)

The compounds of the formula (I) where n is 0 can be prepared by reacting the compounds of the formula (X) with the compounds of the formula (VIa) in the presence of a base. Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

Alternatively, it is possible to directly use the salts of the mercaptan derivatives, for example sodium ethanethiolate, sodium methanethiolate or sodium isopropanethiolate, without addition of further base.

Step f, g)

The compounds of the formula (I) where n is 1 can be prepared by oxidizing the compounds of the formula (I) where n is 0. The oxidation is effected by known methods using a suitable oxidizing agent, for example hydrogen peroxide, meta-chloroperbenzoic acid or sodium periodate.

The compounds of the formula (I) where n is 2 can be prepared by oxidizing the compounds of the formula (I) where n is 1.

The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Step h)

The compounds of the formula (I) where n is 2 can also be prepared in a one-step process by oxidizing the compounds of the formula (I) where n is 0. The oxidation is generally conducted in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

The compounds of the formula (I') in which Q is Q10, Q11, Q15 and Q16 can likewise be prepared analogously to process B.

Process C

The compounds of the formula (I) in which Q represents Q17 can be prepared by known methods, for example analogously to the processes described in WO2014/142292.

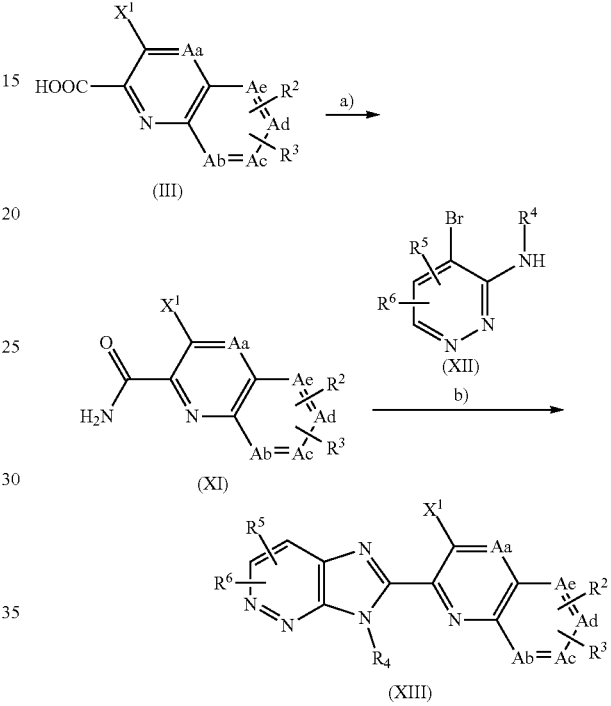

The radicals $R^2$, $R^3$, $R^4$, $R^5$, $R^6$, Aa, Ab, Ac, Ad and Ae have the definitions described above. $X^1$ is halogen.

Step a)

The compounds of the formula (XI) can be prepared in analogy to the process described in U.S. Pat. No. 5,374,646 or Bioorganic and Medicinal Chemistry Letters 2003, 13, 1093-1096 by reacting compounds of the formula (III) with an ammonia source in the presence of a condensing agent.

Carboxylic acids of the formula (III) are either commercially available or can be prepared by known methods. Possible preparation routes are described in process F.

The reaction of the compounds of the formula (III) with the ammonia source is preferably conducted in a solvent selected from customary solvents which are inert under the prevailing reaction conditions. Preference is given to ethers, for example dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (XIII) can be prepared in analogy to the process described in WO2014/142292 by reacting compounds of the formula (XI) with compounds of the formula (XII) in the presence of a palladium catalyst in basic media.

Compounds of the formula (XII) can be prepared, for example, analogously to the processes described in WO2014/142292. A palladium catalyst used may, for example, be [1,1'-bis-(diphenylphosphino)ferrocene]dichloropalladium(II). Frequently, the bases used are inorganic bases such as potassium tert-butoxide.

The reaction is effected in a solvent. Frequently, toluene is used.

The reaction can be conducted under reduced pressure, at standard pressure or under elevated pressure. Preferably, the reaction is carried out at atmospheric pressure and temperatures from 20 to 110° C.

The further conversion of compounds of the formula (XIII) to compounds of the formula (I) is carried out analogously to process A.

The compounds of the formula (I') in which Q is Q17 can likewise be prepared analogously to process C.

Process D

The compounds of the formula (I) in which Q is Q14 can be prepared by known methods, for example analogously to the processes described in WO2011/073149.

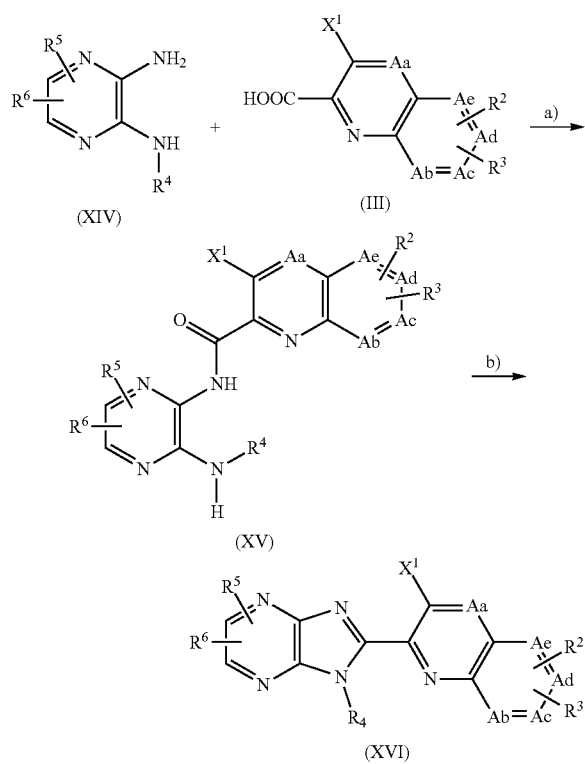

The radicals $R^2$, $R^3$, $R^4$, $R^5$, $R^6$, Aa, Ab, Ac, Ad and Ae have the definitions described above. X' is halogen.

Step a)

The compounds of the formula (XV) can be prepared in analogy to the process described in WO2011/073149 or U.S. Pat. No. 5,576,335 by the reaction of compounds of the formula (XIV) with a carboxylic acid of the formula (III) in the presence of a condensing agent or a base.

Compounds of the formula (XIV) are either commercially available or can be prepared by known methods, for example analogously to the processes described in WO2008/51493 or in Bioorganic and Medicinal Chemistry 2014, 22, 13, 3515-3526.

Carboxylic acids of the formula (III) are either commercially available or can be prepared by known methods. Possible preparation routes are described in process F.

The reaction of the compounds of the formula (XIV) with carboxylic acids of the formula (III) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen-containing compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be effected under reduced pressure, at standard pressure or under elevated pressure and at temperatures of 0° C. to 180° C.; with preference, the reaction is carried out at standard pressure and temperatures of 20 to 140° C.

Step b)

The compounds of the formula (XVI) can be prepared by condensing the compounds of the formula (XV), for example analogously to the processes described in WO2009/131237, WO2010/125985, WO2011/043404, WO2011/040629, WO2012/086848, WO2013/018928 or WO2015/000715.

The conversion to compounds of the formula (XVI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be conducted in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be conducted under reduced pressure, at standard pressure or under elevated pressure, and at temperatures of 0° C. to 200° C.

The further conversion of compounds of the formula (XVI) to compounds of the formula (I) is carried out analogously to process A.

The compounds of the formula (I') in which Q is Q14 can likewise be prepared analogously to process D.

Process E

The compounds of the formula (I) in which Q represents Q12, Q13, Q18 or Q19 can be prepared by known methods, for example analogously to the processes described in WO2010/091310, WO 2012/66061 or WO2013/099041.

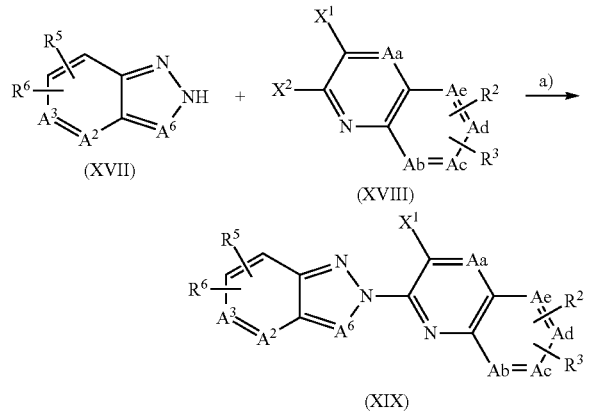

The radicals $R^2$, $R^3$, $R^5$, $R^6$, Aa, Ab, Ac, Ad and Ae have the definitions described above. $A^2$, $A^3$ and $A^6$ are CH or N (where $A^2$ and $A^3$ cannot both be N). $X^1$ and $X^2$ are halogen.

Step a)

The compounds of the formula (XIX) can be prepared by reacting compounds of the formula (XVII) with compounds of the formula (XVIII) under basic conditions, for example analogously to the processes described in WO2010/091310, WO 2012/66061, WO2013/099041 or Tetrahedron 1993, 49, 10997-11008.

Compounds of the formula (XVII) are either commercially available or can be prepared by known methods, for example analogously to the processes described in WO2005/100353, WO 2012/66061 or in European Journal of Medicinal Chemistry 2010, 45, 2214-2222.

Compounds of the formula (XVIII) are either commercially available or can be prepared by known methods, for example analogously to the processes described in WO2013/43518, EP2168965 or in Journal of Medicinal Chemistry 2003, 46, 1449-1455.

The bases used are usually inorganic bases such as sodium hydride, potassium carbonate or caesium carbonate.

The conversion to compounds of the formula (XIX) is usually effected in a solvent, preferably in a nitrile, for example acetonitrile or propionitrile, or in an aprotic polar solvent, for example N,N-dimethylformamide or N-methylpyrrolidone.

The reaction can be conducted under reduced pressure, at standard pressure or under elevated pressure, and at temperatures of 0° C. to 200° C.

Alternatively, the reaction of compounds of the formula (XVII) with compounds of the formula (XVIII) to give compounds of the formula (XIX) can also be effected by palladium-catalysed N-arylation, e.g. analogously to the processes described in Angewandte Chemie Int. Ed. 2011, 50, 8944-8947.

The further conversion of compounds of the formula (XIX) to compounds of the formula (I) is effected analogously to process A.

The compounds of the formula (I') in which Q is Q12, Q13, Q18 and Q19 can likewise be prepared analogously to process E.

Process F-1

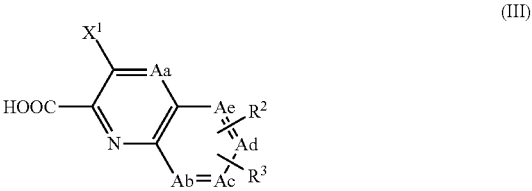

Carboxylic acids of the formula (III) are either commercially available or can be prepared by known methods, for example from aminoaryl, diaminoaryl, aminohetaryl or diaminohetaryl derivatives in analogy to the methods described in Journal of the American Chemical Society, 137 (2015), 6168-6171; Journal of the American Chemical Society, 137 (2015), 2996-3003; Synlett, 3 (2006), 379-382; Organic Letters, 14, (2012), 836-839; Indian Journal of Chemistry, Section B: Organic Chemistry Including Medicinal Chemistry, 22B (1983), 178-179; Journal of Organic Chemistry, 55 (1990), 2838-2842; Tetrahedron Letters, 41 (2000), 8053-8057; US2013/0225552; Organic Reactions (Hoboken, N.J., United States), 28, 1982; WO2011/150156; JP2009/173589; Synthetic Communications 41 (2011), 1843-1851; Journal of the Chemical Society, (1954), 1879-1882; Heterocycles, 60 (2003), 953-957; Organic & Biomolecular Chemistry, 5 (2007), 61-64; Chemical Communications, 2 (2002), 180-181; Tetrahedron Letters, 48 (2007), 5371-5374; Chemistry—A European Journal, 20 (2014), 5569-5572; CN103420927, Medicinal Chemistry Research, 22 (2013), 1660-1673; Medicinal Chemistry Letters, 6 (2015), 282-286 and WO2015/071178.

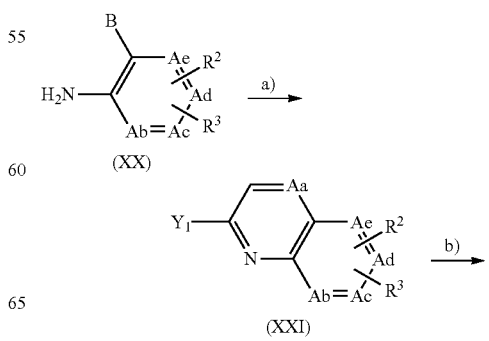

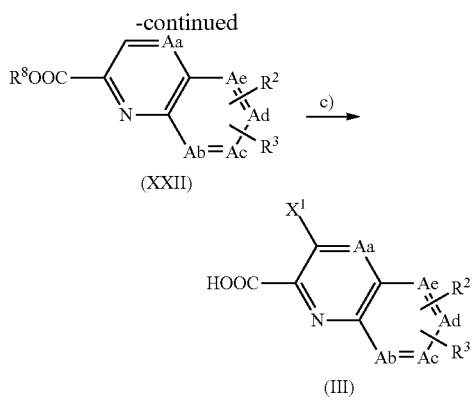

(XXII)

(III)

The radicals $R^2$, $R^3$, Aa, Ab, Ac, Ad and Ae have the definitions described above. B is hydrogen, halogen, $NH_2$ or CHO. $X^1$ is halogen and $Y^1$ is halogen, methyl, $C(O)OR^8$ or cyano. $R^8$ is hydrogen or $C_1$-$C_6$-alkyl.

Step a)

The compounds of the formula (XXI) in which Aa is N can be prepared in analogy to the processes described in Tetrahedron Letters, 48 (2007), 5371-5374; Chemistry—A European Journal, 20 (2014), 5569-5572; CN103420927; Medicinal Chemistry Research, 22 (2013), 1660-1673; Medicinal Chemistry Letters, 6 (2015), 282-286, by the reaction of compounds of the formula (XX) in which B is $NH_2$ with a carbonyl compound under basic, acidic or thermal conditions.

The compounds of the formula (XXI) in which Aa is $CR^7$ can be prepared in analogy to the processes described in Journal of the American Chemical Society, 137 (2015), 6168-6171; Journal of the American Chemical Society, 137 (2015), 2996-3003; Synlett, 3 (2006), 379-382; Organic Letters, 14, (2012), 836-839; Tetrahedron Letters, 41 (2000), 8053-8057; US2013/0225552; Organic Reactions (Hoboken, N.J., United States), 28, 1982; WO2011/150156; Synthetic Communications 41 (2011), 1843-1851; Journal of the Chemical Society, (1954), 1879-1882; Organic & Biomolecular Chemistry, 5 (2007), 61-64, by a condensation and subsequent cyclization of compounds of the formula (XX) in which B is hydrogen, halogen or CHO with a suitable carbonyl compound or a carboxylic acid derivative under basic, acidic or thermal conditions. The further functionalization in the 4 position for introduction of radicals of the $R^7$ type hydrogen) can be achieved, for example as described in WO2013/066736 via a halogenation; as described in Practical Methods for Biocatalysis and Biotransformations 2, (2012), 153-157 via a hydroxylation; as described in Organometallics, 9 (1990), 1778-1784 via an alkylation; as described in Journal of Heterocyclic Chemistry, 22 (1985), 353-355 via an amination, or as described in WO2010/020981 via a nitration.

The compounds of the formula (XX) are either commercially available or can be prepared by known methods, for example in analogy to the methods described in Chemical Reviews, 12 (1933), 43-179; Chemical Reviews, 57 (1957), 525-581; Journal of Organic Chemistry, 15 (1950), 1224-1232; Recueil Travaux Chimiques des Pays-Bas et de la Belgique, 69 (1950), 468-673; Journal of Chemical Technology and Biotechnology, 37 (1987), 195-202; WO2012/117000; Chemistry—A European Journal, 18 (2012), 16358-16368; Journal of Organic Chemistry, 48 (1983), 1064-1069; Organic Synthesis, 44 (1964), 34-39; Journal of Heterocyclic Chemistry, 23 (1986), 669-672; Bioorganic & Medicinal Chemistry Letters, 18 (2008), 5023-5026; Journal of Organic Chemistry, 48 (1983), 3401-3408; Journal of Heterocyclic Chemistry, 48 (2011), 1383-1387; WO2003/051366; Helvetica Chimica Acta, 18 (1935), 1229-1239; Synthesis, 1 (1978), 23-24; Organic Synthesis, 19 (1939), 70-72; Canadian Journal of Chemistry, 38 (1960), 2363-2366; Journal of Organic Chemistry, 42 (1977), 3491-3496.

Step b)

Compounds of the formula (XXII) can be prepared by known methods, for example via a hydrolysis of compounds of the formula (XXI) (if $Y^1$=$C(O)OR^8$ or cyano) under acidic, basic or thermal conditions.

Compounds of the formula (XXII) can be prepared in analogy to the processes described in Synlett, 3 (2006), 379-382; Indian Journal of Chemistry, Section B: Organic Chemistry Including Medicinal Chemistry, 22B (1983), 178-179; Journal of Organic Chemistry, 55 (1990), 2838-2842; Heterocycles, 60 (2003), 953-957; Chemical Communications, 2 (2002), 180-181 and WO2015/071178, via a benzylic oxidation from compounds of the formula (XXI) (if $Y^1$=methyl).

Compounds of the formula (XXII) can be prepared in analogy to the processes described in Journal of the American Chemical Society, 135 (2013), 2891-2894; Synlett, 11 (2006), 1663-1666; Helvetica Chimica Acta, 55 (1972), 2295-2300; WO2013/149997 and European Journal of Organic Chemistry, 29 (2014), 6418-6430 via a carbonylation ($R^8$=alkyl) or a carboxylation ($R^8$=hydrogen) from compounds of the formula (XXI) (if $Y^1$=halogen).

Step c)

Compounds of the formula (III) can be prepared by known methods from compounds of the formula (XXII) via a halogenation. This can be effected, for example, via a directed ortho-lithiation, followed by capture of the carbanion with a suitable electrophilic halogenating reagent or alternatively via a carboxylic acid derivative-directed halogenation in analogy to the processes described in Bioorganic & Medicinal Chemistry Letters, 24 (2014), 4236-4238; Tetrahedron, 58 (2002), 6723-6728 and WO2003/010146.

If $R^8$ is $C_1$-$C_6$-alkyl, the corresponding carboxylic esters of the formula (XXII), after the halogenation, can be hydrolysed under acidic or basic conditions in a polar protic solvent, such as ethanol or methanol, or a polar aprotic solvent, such as tetrahydrofuran, using, for example, dilute hydrochloric acid or alkali metal hydroxides, to the carboxylic acids of the formula (III).

Process F-2

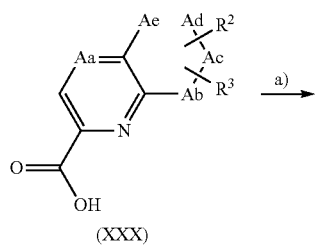

(XXX)

-continued

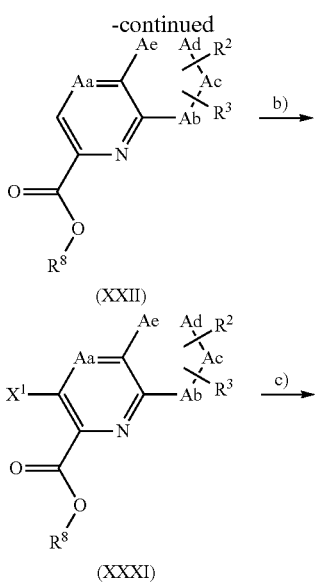

Step c)

The compounds of the formula (III) are either commercially available or can be synthesized in analogy to the processes described in Synthesis 1987, 6, 586-587, Tetrahedron Letters 2006, 47, 565-567 or ChemMedChem 2010, 5, 65-78 via a hydrolysis from the compounds of the formula (XXXI).

Alternatively, quinoline derivatives of the formula (III) can also be prepared analogously to the processes described in Organic Reactions (Hoboken, N.J., United States), 28, 1982 and Journal of Organic Chemistry 2016, 81, 57-65 via a ring expansion of the corresponding indole derivatives.

Examples of suitable bases are, for example, lithium hydroxide or sodium hydroxide. Solvents used may be polar aprotic and protic solvents and mixtures of these, for example ethanol, tetrahydrofuran or water.

The reaction can be conducted under reduced pressure, at standard pressure or under elevated pressure, and at temperatures of −20° C. to 120° C.

Process G-1

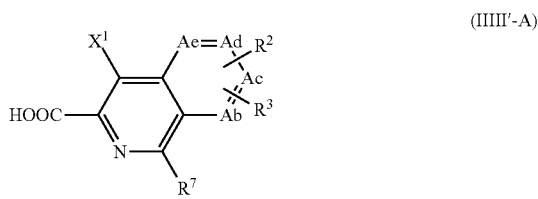

The radicals $R^2$, $R^3$, Aa, Ab, Ac, Ad and Ae have the definitions described above. $X^1$ is halogen. $R^8$ is $C_1$-$C_6$-alkyl.

Step a)

Compounds of the formula (XXII) are either commercially available or can be obtained in analogy to the processes described in ChemSusChem 2015, 8, 1916-1925, Chemical Engineering Journal 2015, 271, 269-275, Catalysis Communications 2015, 59, 122-126, Synthetic Communications 2014, 44, 2386-2392, Synthetic Communications 2014, 44, 836-846, Journal of Organic Chemistry 2013, 78, 11606-11611, Organic Letters 2011, 13, 320-323 and Journal of the American Chemical Society 1948, 70, 3135-3136 from the corresponding carboxylic acids of the formula (XXX) via an esterification or alkylation under acidic or neutral conditions.

The compounds of the formula (XXX) are commercially available or can be prepared via a hydrolysis from compounds of the formula (XXII).

The reaction can be effected under reduced pressure, at standard pressure or under elevated pressure and at temperatures of 0° C. to 180° C.; with preference, the reaction is carried out at standard pressure and temperatures of 20 to 140° C.

Step b)

Compounds of the formula (XXXI) can be prepared by known methods from compounds of the formula (XXII) via a halogenation. This can be effected, for example, via a directed ortho-lithiation, followed by capture of the carbanion with a suitable electrophilic halogenating reagent or alternatively via a carboxylic acid derivative-directed halogenation in analogy to the processes described in Bioorganic & Medicinal Chemistry Letters, 24 (2014), 4236-4238; Tetrahedron, 58 (2002), 6723-6728 and WO2003/010146.

Carboxylic acids of the formula (III'-A) are either commercially available or can be prepared by known methods, for example from benzylamines or hetarylmethanamines in analogy to the processes described in Tetrahedron, 40 (1984), 311-314, Monatshefte für Chemie, 139 (2008), 673-684, Synlett, 3 (2006), 379-382; Indian Journal of Chemistry, Section B: Organic Chemistry Including Medicinal Chemistry, 22B (1983), 178-179; Journal of Organic Chemistry, 55 (1990), 2838-2842; Heterocycles, 60 (2003), 953-957; Chemical Communications, 2 (2002), 180-181, WO2015/071178, Bioorganic & Medicinal Chemistry Letters, 24 (2014), 4236-4238; Tetrahedron, 58 (2002), 6723-6728 and WO2003/010146.

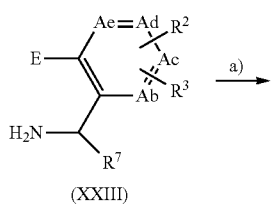

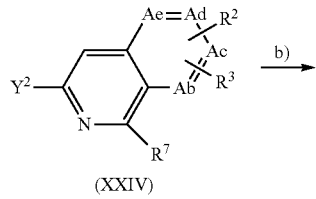

-continued

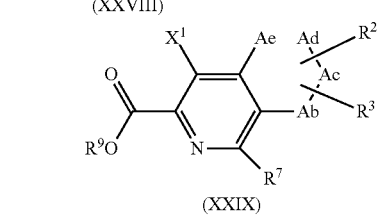

(XXV)

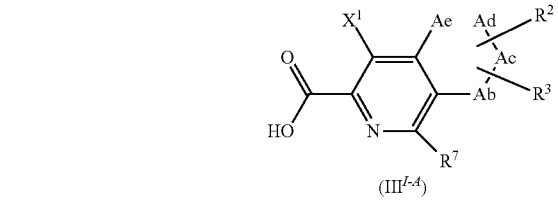

(III$^{I-A}$)

The radicals R$^2$, R$^3$, R$^7$, Aa, Ab, Ac, Ad and Ae have the definitions described above. E is hydrogen or halogen and X$^1$ is halogen. Y$^2$ is methyl, C(O)OR$^8$ or cyano. R$^8$ is hydrogen or C$_1$-C$_6$-alkyl.

Step a)

The compounds of the formula (XXIV) can be synthesized in analogy to the processes described in Tetrahedron, 40 (1984), 311-314 or Monatshefte für Chemie, 139 (2008), 673-684 via a condensation of benzylamines or hetarylmethanamines of the formula (XXIII) with the corresponding carbonyl compounds under acidic or basic conditions.

The compounds of the formula (XXIII) are either commercially available or can be prepared by known methods, for example in analogy to the methods described in WO1997/41846; US2011/0105753; Journal of Medicinal Chemistry, 46 (2003), 461-473; WO2010/024430; WO2005/111003; Journal of Heterocyclic Chemistry, 23 (1986), 989-990.

Step b)

Compounds of the formula (XXV) can be prepared by known methods, for example via a hydrolysis of compounds of the formula (XXIV) (if Y$^2$=C(O)OR$^8$ or cyano) under acidic, basic or thermal conditions.

Compounds of the formula (XXV) can be prepared in analogy to the processes described in Synlett, 3 (2006), 379-382; Indian Journal of Chemistry, Section B: Organic Chemistry Including Medicinal Chemistry, 22B (1983), 178-179; Journal of Organic Chemistry, 55 (1990), 2838-2842; Heterocycles, 60 (2003), 953-957; Chemical Communications, 2 (2002), 180-181 and WO2015/071178, via a benzylic oxidation from compounds of the formula (XXIV) (if Y$^2$=methyl).

Step c)

Compounds of the formula (III'-A) can be prepared by known methods from compounds of the formula (XXV) via a halogenation. This can be effected, for example, via a directed ortho-lithiation, followed by capture of the carbanion with a suitable electrophilic halogenating reagent or alternatively via a carboxylic acid derivative-directed halogenation in analogy to the processes described in Bioorganic & Medicinal Chemistry Letters, 24 (2014), 4236-4238; Tetrahedron, 58 (2002), 6723-6728 and WO2003/010146 (cf. Process F, step c).

Process G-2

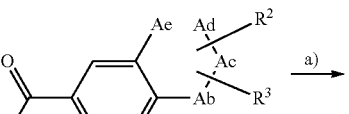

(XXVIII)

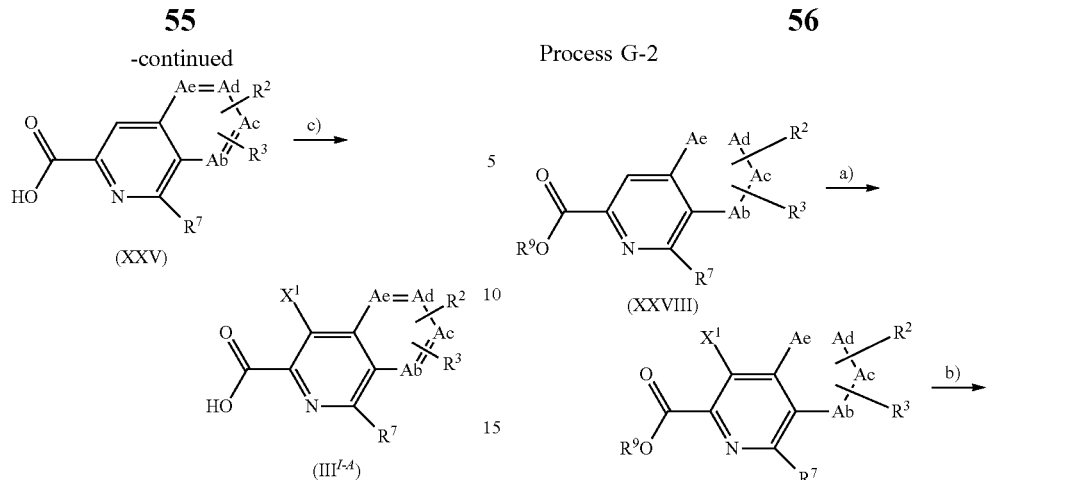

(XXIX)

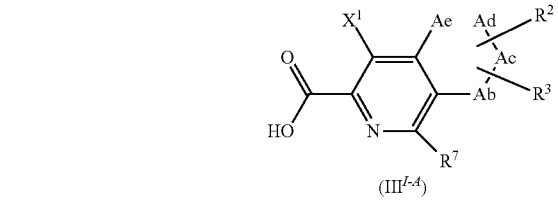

(III$^{I-A}$)

Step a)

Compounds of the formula (XXIX) can be prepared by known methods from compounds of the formula (XXVIII) via a halogenation. This can be effected, for example, via a directed ortho-lithiation, followed by capture of the carbanion with a suitable electrophilic halogenating reagent or alternatively via an electrophilic aromatic halogenation in analogy to the processes described in Bioorganic & Medicinal Chemistry Letters, 24 (2014), 4236-4238; Tetrahedron, 58 (2002), 6723-6728 and WO2003/010146 (cf. Process F-1, step c). Compounds of the formula (XXVIII) are commercially available or can be synthesized via an esterification from compounds of the formula (XXV).

Step b)

The compounds of the formula (III'') can be synthesized in analogy to the processes described in Synthesis 1987, 6, 586-587, Tetrahedron Letters 2006, 47, 565-567 or ChemMedChem 2010, 5, 65-78 via a hydrolysis from the compounds of the formula (XXIX).

Examples of suitable bases are, for example, lithium hydroxide or sodium hydroxide. Solvents used may be polar aprotic and protic solvents and mixtures of these, for example ethanol, tetrahydrofuran or water.

The reaction can be conducted under reduced pressure, at standard pressure or under elevated pressure, and at temperatures of −20° C. to 120° C.

Process H

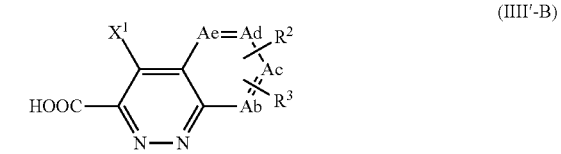

(III'-B)

Carboxylic acids of the formula (III'-B) are either commercially available or can be prepared by known methods, for example from haloarylcarboxylic acids or the corresponding haloheteroarylcarboxylic acids in analogy to the processes described in Science of Synthesis, 16 (2004), 1109-1153 and Journal of Medicinal Chemistry, 58 (2015), 480-511.

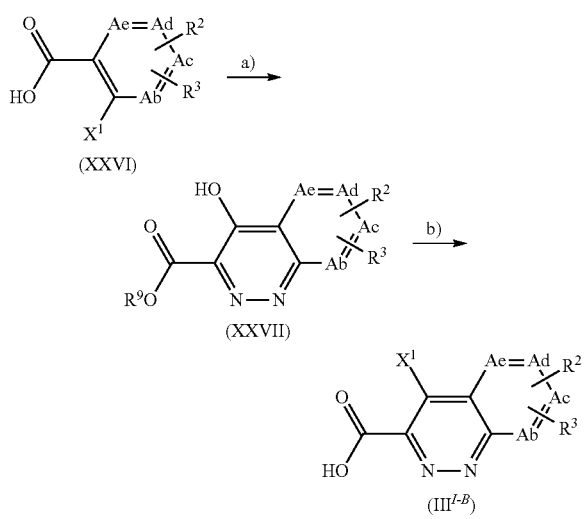

The radicals $R^2$, $R^3$, Ab, Ac, Ad and Ae have the definitions described above. $X^1$ is halogen. $R^9$ is $C_1$-$C_6$-alkyl.

Step a)

The compounds of the formula (XXVII) can be synthesized in analogy to the processes described in WO2004/039802 oder Science of Synthesis, 16 (2004), 1109-1153 via an acetylation of an alkyl 2-diazoacetate with a compound of the formula (XXVI), followed by an N-arylation which leads to the fused bicyclic system.

The compounds of the formula (XXVI) are either commercially available or can be prepared by known methods, for example in analogy to the processes described in Synthesis, 47 (2015), 1861-1868; Justus Liebigs Annalen der Chemie, (1893), 54-57; Journal of the American Chemical Society, 65 (1943), 476-477; Bioorganic & Medicinal Chemistry Letters, 24 (2014), 4236-4238; Organic Letters, 10 (2008), 2701-2704; Journal de Pharmacie de Belgique, 22 (1967), 257-263; Journal of Organic Chemistry, 60 (1995), 292-296; Bioorganic & Medicinal Chemistry Letters, 23 (2013), 1846-1852; JP2012/092060; EU1983/92117; Tetrahedron, 71 (2015), 252-258.

Step b)

Compounds of the formula (III'$^{-B}$) can be prepared by known methods, for example via chlorination with phosphorus oxychloride of compounds of the formula (XXVII), as described in Journal of Medicinal Chemistry, 58 (2015), 480-511.

Methods and Uses

The invention also relates to methods for controlling animal pests, in which compounds of the formula (I) or the formula (I') are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of the formula (I) or formula (I') as pesticides, especially crop protection agents.

In the context of the present application, the term "pesticide" in each case also always encompasses the term "crop protection agent".

The compounds of the formula (I) or the formula (I'), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are conducted on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stalls, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) or the formula (I') can preferably be used as pesticides. They are active against normally sensitive and resistant species and also against all or some stages of development. The abovementioned pests include:

pests from the phylum of the Arthropoda, especially from the class of the Arachnida, for example *Acarus* spp., e.g. *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, e.g. *Geophilus* spp., *Scutigera* spp.;

from the order or the class of the Collembola, e.g. *Onychiurus armatus; Sminthurus viridis*;

from the class of the Diplopoda, e.g. *Blaniulus guttulatus*;

from the class of the Insecta, for example from the order of the Blattodea, e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa*;

from the order of the Coleoptera for example *Acalymma vittatum, Acanthoscelides obtectus, Adoretus* spp., *Aethina tumida, Agelastica alni, Agriotes* spp., e.g. *Agriotes linneatus, Agriotes mancus, Alphitobius diaperinus, Amphimallon solstitialis, Anobium punctatum, Anoplophora* spp., *Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Lissorhoptrus oryzophilus, Listronotus* (=*Hyperodes*) spp., *Lixus* spp., *Luperodes* spp., *Luperomorpha xanthodera, Lyctus* spp., *Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides*;

from the order of the Dermaptera, for example *Anisolabis maritime, Forficula auricularia, Labidura riparia*;

from the order of the Diptera, for example *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g. *Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterborniella subcincta, Pegomya oder Pegomyia* spp., e.g. *Pegomya betae, Pegomya hyoscyami, Pegomya rubivora, Phlebotomus* spp., *Phorbia* spp., *Phormia* spp., *Piophila casei, Platyparea poecilloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda*;

from the order of the Hemiptera, for example *Acizzia acaciaebaileyanae, Acizzia dodonaeae, Acizzia uncatoides*,

*Acrida turrita, Acyrthosipon* spp., e.g. *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., e.g. *Amrasca bigutulla, Amrasca devastans, Anuraphis cardui, Aonidiella* spp., e.g. *Aonidiella aurantii, Aonidiella citrina, Aonidiella inornata, Aphanostigma pini, Aphis* spp., e.g. *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., e.g. *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., e.g. *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., e.g. *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., e.g. *Dysaphis apiifolia, Dysaphis plantaginea, Dysaphis tulipae, Dysmicoccus* spp., *Empoasca* spp., e.g. *Empoasca abrupta, Empoasca fabae, Empoasca maligna, Empoasca solana, Empoasca stevensi, Eriosoma* spp., e.g. *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., e.g. *Icerya purchasi, Idiocerus* spp., *Idioscopus* spp., *Laodelphax striatellus, Lecanium* spp., e.g. *Lecanium corni* (=*Parthenolecanium corni*), *Lepidosaphes* spp., e.g. *Lepidosaphes ulmi, Lipaphis erysimi, Lopholeucaspis japonica, Lycorma delicatula, Macrosiphum* spp., e.g. *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., e.g. *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., e.g. *Nephotettix cincticeps, Nephotettix nigropictus, Nettigonicla spectra, Nilaparvata lugens, Oncometopia* spp., *Orthezia praelonga, Oxya chinensis, Pachypsylla* spp., *Parabemisia myricae, Paratrioza* spp., e.g. *Paratrioza cockerelli, Parlatoria* spp., *Pemphigus* spp., e.g. *Pemphigus bursarius, Pemphigus populivenae, Peregrinus maidis, Perkinsiella* spp., *Phenacoccus* spp., e.g. *Phenacoccus madeirensis, Phloeomyzus passerinii, Phorodon humuli, Phylloxera* spp., e.g. *Phylloxera devastatrix, Phylloxera notabilis, Pinnaspis aspidistrae, Planococcus* spp., e.g. *Planococcus citri, Prosopidopsylla flava, Protopulvinaria pyriformis, Pseudaulacaspis pentagona, Pseudococcus* spp., e.g. *Pseudococcus calceolariae, Pseudococcus comstocki, Pseudococcus longispinus, Pseudococcus maritimus, Pseudococcus viburni, Psyllopsis* spp., *Psylla* spp., e.g. *Psylla buxi, Psylla mali, Psylla pyri, Pteromalus* spp., *Pulvinaria* spp., *Pyrilla* spp., *Quadraspidiotus* spp., e.g. *Quadraspidiotus juglansregiae, Quadraspidiotus ostreaeformis, Quadraspidiotus perniciosus, Quesada gigas, Rastrococcus* spp., *Rhopalosiphum* spp., e.g. *Rhopalosiphum maidis, Rhopalosiphum oxyacanthae, Rhopalosiphum padi, Rhopalosiphum rufiabdominale, Saissetia* spp., e.g. *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., e.g. *Toxoptera aurantii, Toxoptera citricidus, Trialeurodes vaporariorum, Trioza* spp., e.g. *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., e.g. *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., e.g. *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., e.g. *Lygocoris pabulinus, Lygus* spp., e.g. *Lygus elisus, Lygus hesperus, Lygus lineolaris, Macropes excavatus, Megacopta cribraria, Miridae, Monalonion atratum, Nezara* spp., e.g. *Nezara viridula, Nysius* spp., *Oebalus* spp., *Pentomidae, Piesma quadrata, Piezodorus* spp., e.g. *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., e.g. *Athalia rosae, Atta* spp., *Camponotus* spp., *Dolichovespula* spp., *Diprion* spp., e.g. *Diprion similis, Hoplocampa* spp., e.g. *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., e.g. *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., e.g. *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., e.g. *Reticulitermes flavipes, Reticulitermes hesperus;* from the order of the Lepidoptera, for example *Achroia grisella, Acronicta major, Adoxophyes* spp., e.g. *Adoxophyes orana, Aedia leucomelas, Agrotis* spp., e.g. *Agrotis segetum, Agrotis ipsilon, Alabama* spp., e.g. *Alabama argillacea, Amyelois transitella, Anarsia* spp., *Anticarsia* spp., e.g. *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., e.g. *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., e.g. *Cydia* nigricana, Cydia pomonella, Dalaca noctuides, Diaphania spp., Diparopsis spp., Diatraea saccharalis, Earias spp., Ecdytolopha aurantium, Elasmopalpus lignosellus, Eldana saccharina, Ephestia spp., e.g. Ephestia elutella, Ephestia kuehniella, Epinotia spp., Epiphyas postvittana, Erannis spp., Erschoviella musculana, Etiella spp., Eudocima spp., Eulia spp., Eupoecilia ambiguella, Euproctis spp., e.g. Euproctis chrysorrhoea, Euxoa spp., Feltia spp., Galleria mellonella, Gracillaria spp., Grapholitha spp., e.g. Grapholita molesta, Grapholita prunivora, Hedylepta spp., Helicoverpa spp., e.g. Helicoverpa armigera, Helicoverpa zea, Heliothis spp., e.g. Heliothis virescens Hofmannophila pseudospretella, Homoeosoma spp., Homona spp., Hyponomeuta padella, Kakivoria flavofasciata, Lampides spp., Laphygma spp., Laspeyresia molesta, Leucinodes orbonalis, Leucoptera spp., e.g. Leucoptera coffeella, Lithocolletis spp., e.g. Lithocolletis blancardella, Lithophane antennata, Lobesia spp., e.g. Lobesia botrana, Loxagrotis albicosta, Lymantria spp., e.g. Lymantria dispar, Lyonetia spp., e.g. Lyonetia clerkella, Malacosoma neustria, Maruca testulalis, Mamestra brassicae, Melanitis leda, Mocis spp., Monopis obviella, Mythimna separata, Nemapogon cloacellus, Nymphula spp., Oiketicus spp., Omphisa spp., Operophtera spp., Oria spp., Orthaga spp., Ostrinia spp., e.g. Ostrinia nubilalis, Panolis flammea, Parnara spp., Pectinophora spp., e.g. Pectinophora gossypiella, Perileucoptera spp., Phthorimaea spp., e.g. Phthorimaea operculella, Phyllocnistis citrella, Phyllonorycter spp., e.g. Phyllonorycter blancardella, Phyllonorycter crataegella, Pieris spp., e.g. Pieris rapae, Platynota stultana, Plodia interpunctella, Plusia spp., Plutella xylostella (=Plutella maculipennis), Prays spp., Prodenia spp., Protoparce spp., Pseudaletia spp., e.g. Pseudaletia unipuncta, Pseudoplusia includens, Pyrausta nubilalis, Rachiplusia nu, Schoenobius spp., e.g. Schoenobius bipunctifer, Scirpophaga spp., e.g. Scirpophaga innotata, Scotia segetum, Sesamia spp., e.g. Sesamia inferens, Sparganothis spp., Spodoptera spp., e.g. Spodoptera eradiana, Spodoptera exigua, Spodoptera frugiperda, Spodoptera praefica, Stathmopoda spp., Stenoma spp., Stomopteryx subsecivella, Synanthedon spp., Tecia solanivora, Thaumetopoea spp., Thermesia gemmatalis, Tinea cloacella, Tinea pellionella, Tineola bisselliella, Tortrix spp., Trichophaga tapetzella, Trichoplusia spp., e.g. Trichoplusia ni, Tryporyza incertulas, Tuta absoluta, Virachola spp.;

from the order of the Orthoptera or Saltatoria, for example Acheta domesticus, Dichroplus spp., Gryllotalpa spp., e.g. Gryllotalpa gryllotalpa, Hieroglyphus spp., Locusta spp., e.g. Locusta migratoria, Melanoplus spp., e.g. Melanoplus devastator, Paratlanticus ussuriensis, Schistocerca gregaria;

from the order of the Phthiraptera, for example Damalinia spp., Haematopinus spp., Linognathus spp., Pediculus spp., Phylloxera vastatrix, Phthirus pubis, Trichodectes spp.;

from the order of the Psocoptera, for example Lepinotus spp., Liposcelis spp.;

from the order of the Siphonaptera, for example Ceratophyllus spp., Ctenocephalides spp., e.g. Ctenocephalides canis, Ctenocephalides felis, Pulex irritans, Tunga penetrans, Xenopsylla cheopis;

from the order of the Thysanoptera, for example Anaphothrips obscurus, Baliothrips biformis, Chaetanaphothrips leeuweni, Drepanothrips reuteri, Enneothrips flavens, Frankliniella spp., e.g. Frankliniella fusca, Frankliniella occidentalis, Frankliniella schultzei, Frankliniella tritici, Frankliniella vaccinii, Frankliniella williamsi, Haplothrips spp., Heliothrips spp., Hercinothrips femoralis, Kakothrips spp., Rhipiphorothrips cruentatus, Scirtothrips spp., Taeniothrips cardamomi, Thrips spp., e.g. Thrips palmi, Thrips tabaci;

from the order of the Zygentoma (=Thysanura), for example Ctenolepisma spp., Lepisma saccharina, Lepismodes inquilinus, Thermobia domestica;

from the class of the Symphyla, for example Scutigerella spp., e.g. Scutigerella immaculata;

pests from the phylum of the Mollusca, for example from the class of the Bivalvia, e.g. Dreissena spp.;

and also from the class of the Gastropoda, for example Anion spp., e.g. Anion ater rufus, Biomphalaria spp., Bulinus spp., Deroceras spp., e.g. Deroceras laeve, Galba spp., Lymnaea spp., Oncomelania spp., Pomacea spp., Succinea spp.;

plant pests from the phylum of the Nematoda, i.e. plant-parasitic nematodes, in particular Aglenchus spp., e.g. Aglenchus agricola, Anguina spp., e.g. Anguina tritici, Aphelenchoides spp., e.g. Aphelenchoides arachidis, Aphelenchoides fragariae, Belonolaimus spp., e.g. Belonolaimus gracilis, Belonolaimus longicaudatus, Belonolaimus nortoni, Bursaphelenchus spp., e.g. Bursaphelenchus cocophilus, Bursaphelenchus eremus, Bursaphelenchus xylophilus, Cacopaurus spp., e.g. Cacopaurus pestis, Criconemella spp., e.g. Criconemella curvata, Criconemella onoensis, Criconemella ornata, Criconemella rusium, Criconemella xenoplax (=Mesocriconema xenoplax), Criconemoides spp., e.g. Criconemoides ferniae, Criconemoides onoense, Criconemoides ornatum, Ditylenchus spp., e.g. Ditylenchus dipsaci, Dolichodorus spp., Globodera spp., e.g. Globodera pallida, Globodera rostochiensis, Helicotylenchus spp., e.g. Helicotylenchus dihystera, Hemicriconemoides spp., Hemicycliophora spp., Heterodera spp., e.g. Heterodera avenae, Heterodera glycines, Heterodera schachtii, Hirschmaniella spp., Hoplolaimus spp., Longidorus spp., e.g. Longidorus africanus, Meloidogyne spp., e.g. Meloidogyne chitwoodi, Meloidogyne fallax, Meloidogyne hapla, Meloidogyne incognita, Meloinema spp., Nacobbus spp., Neotylenchus spp., Paralongidorus spp., Paraphelenchus spp., Paratrichodorus spp., e.g. Paratrichodorus minor, Paratylenchus spp., Pratylenchus spp., e.g. Pratylenchus penetrans, Pseudohalenchus spp., Psilenchus spp., Punctodera spp., Quinisulcius spp., Radopholus spp., e.g. Radopholus citrophilus, Radopholus similis, Rotylenchulus spp., Rotylenchus spp., Scutellonema spp., Subanguina spp., Trichodorus spp., e.g. Trichodorus obtusus, Trichodorus primitivus, Tylenchorhynchus spp., e.g. Tylenchorhynchus annulatus, Tylenchulus spp., e.g. Tylenchulus semipenetrans, Xiphinema spp., e.g. Xiphinema index.

The compounds of the formula (I) or the formula (I') can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I) or the formula (I'). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I) or the formula (I'), optionally comprise further active agrochemical ingredients.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) or the formula (I') with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I) or the formula (I'), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, for example xylene, toluene or alkylnaphthalenes, chlorinated aromatic or aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulphoxide, and water.

In principle, it is possible to use all suitable carriers. Useful carriers especially include, for example, ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) or the formula (I') and/or one of the inert carriers is insoluble in water and when the application is effected in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) or the formula (I') can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of active agrochemical ingredients into plants. Penetrants are defined in this context by their ability to penetrate from the (generally aqueous) application liquor and/or from the spray coating into the cuticle of the plant and hence increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I) or the formula (I'), more preferably between 0.01% and 95% by weight of the compound of the formula (I) or the formula (I'), most preferably between 0.5% and 90% by weight of the compound of the formula (I) or the formula (I'), based on the weight of the formulation.

The content of the compound of the formula (I) or the formula (I') in the use forms prepared from the formulations (in particular pesticides) may vary within wide ranges. The concentration of the compound of the formula (I) or the formula (I') in the use forms may typically be between 0.00000001% and 95% by weight of the compound of the formula (I) or the formula (I'), preferably between 0.00001% and 1% by weight, based on the weight of the use form. Application is accomplished in a customary manner appropriate for the use forms.

Mixtures

The compounds of the formula (I) or the formula (I') can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) or the formula (I') may be present in a mixture with other active ingredients or semiochemicals such as attractants and/or bird repellents and/or plant activators and/or growth regulators and/or fertilizers. Likewise, the compounds of the formula (I) or the formula (I') can be used to improve plant properties, for example growth, yield and quality of the harvested material.

In a particular embodiment according to the invention, the compounds of the formula (I) or the formula (I') are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinergic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example, juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulphuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect midgut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinergic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, novifluuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilide, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulphinyl]propanamide, (+)-N-[3-chloro-1-(3-pyridinyl)-1H-pyrazol-4-yl]-N-ethyl-3-[(3,3,3-trifluoropropyl)sulphinyl]propanamide and (−)-N-[3-chloro-1-(3-pyridinyl)-1H-pyrazol-4-yl]-N-ethyl-3-[(3,3,3-trifluoropropyl)sulphinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulphinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8) and N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9).

Fungicides

The active ingredients specified here by their "common names" are known and are described, for example, in the "Pesticide Manual" (16th ed., British Crop Protection Council) or can be searched for on the Internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components of classes (1) to (15) mentioned, as the case may be, may include tautomeric forms.

1) Ergosterol biosynthesis inhibitors, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1 S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1 S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl]-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)

phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulphanyl)-1-{[3-(2-chlorophenyl)-2-(2,4-difluorophenyl)oxiran-2-yl]methyl]-1H-1,2,4-triazole, (1.061) 5-(allylsulphanyl)-1-{[rel(2R,3R)-3-(2-chlorophenyl)-2-(2,4-difluorophenyl)oxiran-2-yl]methyl}-1H-1,2,4-triazole, (1.062) 5-(allylsulphanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulphanyl}phenyl)-N-ethyl-N-methylimidoformamide, (1.064) N'-(2,5-dimethyl-4-{[3-(2,2,2-trifluoroethoxy)phenyl]sulphanyl}phenyl)-N-ethyl-N-methylimidoformamide, (1.065) N'-(2,5-dimethyl-4-{[3-(2,2,3,3-tetrafluoropropoxy)phenyl]sulphanyl}phenyl)-N-ethyl-N-methylimidoformamide, (1.066) N'-(2,5-dimethyl-4-{[3-(pentafluoroethoxy)phenyl]sulphanyl}phenyl)-N-ethyl-N-methylimidoformamide, (1.067) N'-(2,5-dimethyl-4-{3-[(1,1,2,2-tetrafluoroethyl)sulphanyl]phenoxyl}phenyl)-N-ethyl-N-methylimidoformamide, (1.068) N'-(2,5-dimethyl-4-{3-[(2,2,2-trifluoroethyl)sulphanyl]phenoxy}phenyl)-N-ethyl-N-methylimidoformamide, (1.069) N'-(2,5-dimethyl-4-{3-[(2,2,3,3-tetrafluoropropyl)sulphanyl]phenoxy}phenyl)-N-ethyl-N-methylimidoformamide, (1.070) N'-(2,5-dimethyl-4-{3-[(pentafluoroethyl)sulphanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulphanyl}-2,5-dimethylphenyl)-N-ethyl-N-methylimidoformamide, (1.073) N'-(4-{3-[(difluoromethyl)sulphanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H- pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide (5.006) copper naphthenate, (5.007) copper oxide, (5.008) copper oxychloride, (5.009) copper (2+) sulphate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulphur and sulphur preparations including calcium polysulphide, (5.020) thiram, (5.021) zineb, (5.022) ziram.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as decouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2, 3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulphonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulphate (2:1), (15.061) tert-butyl {6-[({[(1-methyl-1H-tetrazol-5-yl)(phenyl)methylene]amino}oxy)methyl]pyridin-2-yl}carbamate.

Biological Pesticides as Mixing Components

The compounds of the formula (I) or the formula (I') can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, especially strain ATCC 74040, *Coniothyrium minitans*, especially strain CON/M/91-8 (Accession No. DSM-9660), *Lecanicillium* spp., especially strain HRO LEC 12, *Lecanicillium lecanii*, (formerly known as *Verticillium lecanii*), especially strain KV01, *Metarhizium anisopliae*, especially strain F52 (DSM3884/ATCC 90448), *Metschnikowia fructicola*, especially strain NRRL Y-30752, *Paecilomyces fumosoroseus* (now: *Isaria fumosorosea*), especially strain IFPC 200613, or strain Apopka 97 (Accesion No. ATCC 20874), *Paecilomyces lilacinus*, especially *P. lilacinus* strain 251 (AGAL 89/030550), *Talaromyces flavus*, especially strain V117b, *Trichoderma atroviride*, especially strain SC1 (Accession Number CBS 122089), *Trichoderma harzianum*, especially *T. harzianum rifai* T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Zaccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), pyrethrum/pyrethrins, *Quassia amara*, *Quercus*, Quillaja, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) or the formula (I') can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) or the formula (I') is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active ingredients, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soybeans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soybeans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) or the formula (I') directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) or the formula (I') by the ultra-low volume method or to inject the application form or the compound of the formula (I) or the formula (I') itself into the soil.

A preferred direct treatment of the plants is foliar application, i.e. compounds of the formula (I) or the formula (I') are applied to the foliage, in which case treatment frequency and the application rate should be adjusted according to the level of infestation with the pest in question.

In the case of systemically active ingredients, the compounds of the formula (I) or the formula (I') also gain access to the plants via the root system. In that case, the plants are treated by the action of the compounds of the formula (I) or the formula (I') on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I) or the formula (I'), or by soil application, meaning that the inventive compounds of the formula (I) or the formula (I') are introduced in solid form (e.g. in the form of granules) into the locus of the plants. In the case of paddy rice crops, this can also be accomplished by metering the compound of the formula (I) or the formula (I') in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I) or the formula (I'). The method according to the invention for protecting seed and germinating plants against attack by pests further comprises a method in which the seed is treated simultaneously in one operation or sequentially with a compound of the formula (I) or the formula (I') and a mixing component. It further also comprises a method where the seed is treated at different times with a compound of the formula (I) or the formula (I') and a mixing component.

The invention likewise relates to the use of the compounds of the formula (I) or the formula (I') for the treatment of seed for protecting the seed and the resulting plant from animal pests.

The invention further relates to seed which has been treated with an inventive compound of the formula (I) or the formula (I') for protection from animal pests. The invention also relates to seed which has been treated simultaneously with a compound of the formula (I) or the formula (I') and a mixing component. The invention further relates to seed which has been treated at different times with a compound of the formula (I) or the formula (I') and a mixing component. In the case of seed which has been treated at different times with a compound of the formula (I) or the formula (I') and a mixing component, the individual substances may be present on the seed in different layers. In this case, the layers comprising a compound of the formula (I) or the formula (I') and mixing components may optionally be separated by an intermediate layer. The invention also relates to seed in which a compound of the formula (I) or the formula (I') and a mixing component have been applied as part of a coating or as a further layer or further layers in addition to a coating.

The invention further relates to seed which, after the treatment with a compound of the formula (I) or the formula (I'), is subjected to a film-coating process to prevent dust abrasion on the seed.

One of the advantages that occur when one of the compounds of the formula (I) or the formula (I') acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) or the formula (I') can enhance germination and emergence of the treated seed.

It is likewise considered to be advantageous that compounds of the formula (I) or the formula (I') can especially also be used for transgenic seed.

Compounds of the formula (I) or the formula (I') can also be used in combination with signalling technology compositions, which results, for example, in better colonization by symbionts, for example *rhizobia*, mycorrhizae and/or endophytic bacteria or fungi, and/or in optimized nitrogen fixation.

The compounds of the formula (I) or the formula (I') are suitable for protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) or the formula (I') is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) or the formula (I') is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

In general, in the treatment of the seed, it has to be ensured that the amount of the compound of the formula (I) and/or the formula (I') and/or further additives applied to the seed is chosen such that the germination of the seed is not impaired and the plant which arises therefrom is not damaged. This has to be ensured particularly in the case of active ingredients which can exhibit phytotoxic effects at certain application rates.

The compounds of the formula (I) or the formula (I') are generally applied to the seed in a suitable formulation. Suitable formulations and processes for seed treatment are known to the person skilled in the art.

The compounds of the formula (I) or the formula (I') can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) or the formula (I') with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Usable with preference are alkyl naphthalenesulphonates, such as diisopropyl or diisobutyl naphthalenesulphonates.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Compositions and Pesticides], vol. 2, Springer Verlag, 1970, p. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) or the formula (I') in the formulations and by the seed. The application rates of the compound of the formula (I) or the formula (I') are generally between 0.001 and 50 g per kilogram of seed, preferably between 0.01 and 15 g per kilogram of seed.

Animal Health

In the animal health field, i.e. the field of veterinary medicine, the compounds of the formula (I) or the formula (I') are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) or the formula (I') having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds, reptiles, amphibians or aquarium fish.

In a particular embodiment, the compounds of the formula (I) or the formula (I') are administered to mammals.

In another particular embodiment, the compounds of the formula (I) or the formula (I') are administered to birds, namely caged birds and particularly poultry.

Use of the compounds of the formula (I) or the formula (I') for the control of animal parasites is intended to reduce or prevent illness, cases of deaths and reductions in performance (in the case of meat, milk, wool, hides, eggs, honey and the like), such that more economical and simpler animal keeping is enabled and better animal well-being is achievable.

In relation to the field of animal health, the term "control" or "controlling" in the present context means that the compounds of the formula (I) or the formula (I') are effective in reducing the incidence of the particular parasite in an animal infected with such parasites to an innocuous degree. More specifically, "controlling" in the present context means that the compounds of the formula (I) or the formula (I') kill the respective parasite, inhibit its growth, or inhibit its proliferation.

The arthropods include, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example, *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example, *Ceratophyllus* spp., *Ctenocephalides* spp., *Pulex* spp., *Tunga* spp., *Xenopsylla* spp.;

from the order of Heteropterida, for example *Cimex* spp., *Panstrongylus* spp., *Rhodnius* spp., *Triatoma* spp.; and also nuisance and hygiene pests from the order Blattarida.

In addition, in the case of the arthropods, mention should be made, without limitation, of the following Acari:

from the subclass of Acari (Acarina) and the order of Metastigmata, for example from the family of Argasidae such as *Argas* spp., *Ornithodorus* spp., *Otobius* spp., from the family of Ixodidae such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata such as *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example, *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example, *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example *Giardia* spp., *Spironucleus* spp.

Parabasala: from the order of Trichomonadida, for example *Histomonas* spp., *Pentatrichomonas* spp., *Tetratrichomonas* spp., *Trichomonas* spp., *Tritrichomonas* spp.

Euglenozoa: from the order of Trypanosomatida, for example *Leishmania* spp., *Trypanosoma* spp.

Sarcomastigophora (Rhizopoda) such as Entamoebidae, for example *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, Nematoden, Pentastoma and Platyhelminthes (e.g. Monogenea, cestodes and trematodes).

Illustrative helminths include, but are not limited to,

Monogenea: for example: *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp. *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditida, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclod-

*ontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal husbandry, the compounds of the formula (I) or the formula (I') are administered by methods generally known in the art, such as via the enteral, parenteral, dermal or nasal route in the form of suitable preparations. Administration may be prophylactic, metaphylactic or therapeutic.

Thus, one embodiment of the present invention refers to the compounds of the formula (I) or the formula (I') for use as a medicament.

A further aspect relates to the compounds of the formula (I) or the formula (I') for use as an antiendoparasitic agent.

A further specific aspect of the invention relates to the compounds of the formula (I) or the formula (I') for use as an antithelminthic agent, especially for use as a nematicide, platyhelminthicide, acanthocephalizide or pentastomicide.

A further specific aspect relates to the compounds of the formula (I) or the formula (I') for use as an antiprotozoic agent.

A further aspect relates to the compounds of the formula (I) or the formula (I') for use as an antiectoparasitic agent, especially an arthropodicide, very particularly an insecticide or an acaricide.

Further aspects of the invention are veterinary medicine formulations comprising an effective amount of at least one compound of the formula (I) or the formula (I') and at least one of the following: a pharmaceutically compatible excipient (e.g. solid or liquid diluent), a pharmaceutically compatible auxiliary (e.g. surfactants), especially a pharmaceutically compatible excipient used conventionally in veterinary medicine formulations and/or a pharmaceutically compatible auxiliary conventionally used in veterinary medicine formulations.

A related aspect of the invention is a method for production of a veterinary medicine formulation as described here, which comprises the step of mixing at least one compound of the formula (I) or the formula (I') with pharmaceutically compatible excipients and auxiliaries, especially with pharmaceutically compatible excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalidicidal, pentastomicidal, insecticidal and acaricidal formulations, according to the above aspects, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) or the formula (I') in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) or the formula (I') in the treatment of a parasite infection, especially an infection caused by a parasite selected from the group of ectoparasites and endoparasites mentioned here, in an animal, especially a nonhuman animal.

In the present context of animal health or veterinary medicine, the term "treatment" refers to prophylactic, metaphylactic and therapeutic treatment.

In a particular embodiment, in this way, mixtures of at least one compound of the formula (I) or the formula (I') with active ingredients, especially with endo- and ectoparasiticides, are provided for the field of veterinary medicine.

In the field of animal health, "mixture" means not just that two (or more) different active ingredients are formulated in a common formulation and correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active ingredients specified here by their "common names" are known and are described, for example, in the "Pesticide Manual" (see above) or can be searched for on the Internet (e.g.: http://www.alanwood.net/pesticides).

Illustrative active ingredients from the group of the ectoparasiticides as mixing components, without any intention that this should constitute a restriction, include the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos (-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive *varroa* acaricides, for example organic acids, e.g. formic acid, oxalic acid.

Illustrative active ingredients from the group of the endoparasiticides, as mixing components, include but are not limited to active anthelmintic ingredients and active antiprotozoic ingredients.

The active anthelmintic ingredients include but are not limited to the following active nematicidal, trematicidal and/or cestocidal ingredients:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophen, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Active antiprotozoic ingredients include but are not limited to the following active ingredients:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquin;

from the class of the pyrimidines, for example: pyrimethamine;

from the class of the sulphonamides, for example: sulfaquinoxaline, trimethoprim, sulfaclozin;

from the class of the thiamines, for example: amprolium;
from the class of the lincosamides, for example: clindamycin;
from the class of the carbanilides, for example: imidocarb;
from the class of the nitrofurans, for example: nifurtimox;
from the class of the quinazolinone alkaloids, for example: halofuginone;
from various other classes, for example: oxamniquin, paromomycin;
from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) or the formula (I') can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted into a host either mechanically (for example trachoma by non-stinging flies) to a host or after injection (for example malaria parasites by mosquitoes).

Examples of vectors and the diseases or pathogens they transmit are:

1) mosquitoes
*Anopheles*: malaria, filariasis;
*Culex*: Japanese encephalitis, filariasis, other viral diseases, transmission of other worms;
*Aedes*: yellow fever, dengue fever, further viral disorders, filariasis;
Simuliidae: transmission of worms, especially *Onchocerca volvulus*;
Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia bungdorferi* sensu lato., *Borrelia duttoni*, tick-borne encephalitis, Q fever (*Coxiella burnetii*), babesioses (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) or the formula (I') are resistance-breaking.

Compounds of the formula (I) or the formula (I') are suitable for use in the prevention of diseases and/or pathogens transmitted by vectors. Thus, a further aspect of the present invention is the use of compounds of the formula (I) or the formula (I') for vector control, for example in agriculture, in horticulture, in forests, in gardens and in leisure facilities, and also in the protection of materials and stored products.

Protection of Industrial Materials

The compounds of the formula (I) or the formula (I') are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) or the formula (I') are used together with at least one further insecticide and/or at least one fungicide.

In a further embodiment, the compounds of the formula (I) or the formula (I') take the form of a ready-to-use pesticide, meaning that they can be applied to the material in question without further modifications. Useful further insecticides or fungicides especially include those mentioned above.

It has also been found that, surprisingly, the compounds of the formula (I) or the formula (I') can be used to protect objects which come into contact with saltwater or brackish water, especially hulls, screens, nets, buildings, moorings and signalling systems, against fouling. It is equally possible to use the compounds of the formula (I) or the formula (I'), alone or in combinations with other active ingredients, as antifouling agents.

Control of Animal Pests in the Hygiene Sector

The compounds of the formula (I) or the formula (I') are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For control of animal pests, the compounds of the formula (I) or the formula (I') are used alone or in combination with other active ingredients and/or auxiliaries. They are preferably used in domestic insecticide products. The compounds of the formula (I) or the formula (I') are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

3-Ethylsulphonyl-2-[3-methyl-6-(trifluoromethyl)imidazo[4,5-c]pyridin-2-yl]quinoline (I-1)

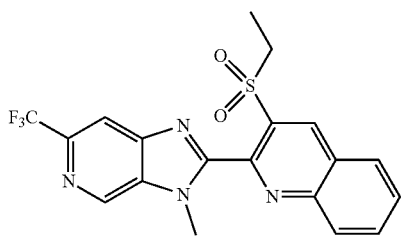 [SMILES: CCS(=O)(=O)c1cc2ccccc2nc1-c1nc2cc(C(F)(F)F)ncc2n1C]

800 mg (2.06 mmol) of 3-ethylsulphanyl-2-[3-methyl-6-(trifluoromethyl)imidazo[4,5-c]pyridin-2-yl]quinoline were dissolved in 200 ml of dichloromethane, 948 mg (20.5 mmol) of formic acid and 2.00 g (20.5 mmol) of hydrogen peroxide were added at room temperature, and then the mixture was stirred at room temperature for 5 h. The mixture was diluted with water, sodium bisulphite solution was added, the mixture was stirred for 1 h, and then 10% sodium hydrogencarbonate solution was added. The organic phase was separated off, the aqueous phase was extracted twice with dichloromethane and the combined organic phases were then freed of the solvent under reduced pressure. The residue was purified by column chromatography purification by means of preparative HPLC with a water/acetonitrile gradient as eluent.

(log P (neutral): 2.75; MH$^+$: 421; $^1$H-NMR (400 MHz, D$_6$-DMSO) δ ppm: 1.23 (t, 3H), 3.83 (q, 2H), 3.93 (s, 3H), 7.97 (t, 1H), 8.15 (t, 1H), 8.29 (d, 1H), 8.33 (s, 1H), 8.51 (d, 1H), 9.32 (s, 1H), 9.34 (s, 1H).

3-Ethylsulphanyl-2-[3-methyl-6-(trifluoromethyl)imidazo[4,5-c]pyridin-2-yl]quinoline (I-2)

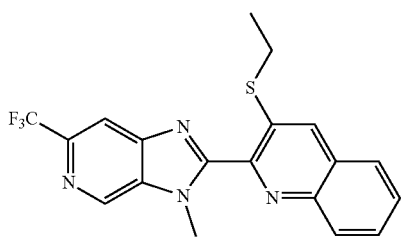 [SMILES: CCSc1cc2ccccc2nc1-c1nc2cc(C(F)(F)F)ncc2n1C]

800 mg (2.20 mmol) of 3-chloro-2-[3-methyl-6-(trifluoromethyl)imidazo[4,5-c]pyridin-2-yl]quinoline and 557 mg (6.61 mmol) of sodium ethanethiolate were stirred in DMF at room temperature under argon for 4 h. Water was added and the mixture was extracted twice with ethyl acetate. The combined organic phases were washed with a sodium chloride solution, removed, dried over sodium sulphate and freed of the solvent under reduced pressure.

(log P (neutral): 3.30; MH$^+$: 389; $^1$H-NMR (400 MHz, D$_6$-DMSO) δ ppm: 1.27 (t, 3H), 3.12 (q, 2H), 4.03 (s, 3H), 7.74-7.84 (m, 2H), 8.08-8.11 (m, 2H), 8.32 (s, 1H), 8.58 (s, 1H), 9.29 (s, 1H).

3-Chloro-2-[3-methyl-6-(trifluoromethyl)imidazo[4,5-c]pyridin-2-yl]quinoline (V-1)

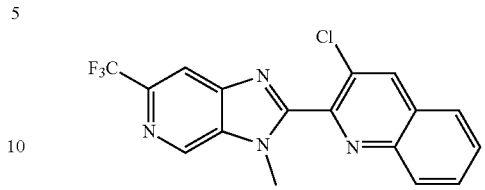

450 mg (2.35 mmol) of N$^3$-methyl-6-(trifluoromethyl)pyridine-3,4-diamine, 489 g (2.35 mmol) of 3-chloroquinoline-2-carboxylic acid and 451 mg (2.35 mmol) of 1-(3-dimethylaminopropyl)-3-ethylcarbodiimide hydrochloride (EDCI) were stirred in 6 ml of pyridine at 120° C. for 9 h. The reaction mixture was freed of the solvent under reduced pressure, then water was added and the mixture was extracted three times with ethyl acetate. The combined organic phases were dried over sodium sulphate and concentrated again.

The residue was dissolved in 15 ml of toluene, 582 mg (3.06 mmol) of para-toluenesulphonic acid were added, and the mixture was stirred at 80° C. for 1 h and 120° C. for 3 h. Subsequently, the reaction mixture was admixed with saturated sodium hydrogencarbonate solution and extracted twice with ethyl acetate. The combined organic phases were dried over sodium sulphate and freed of the solvent under reduced pressure.

(log P (neutral): 2.89; MH$^+$: 363; $^1$H-NMR (400 MHz, D$_6$-DMSO) δ ppm: 4.03 (s, 3H), 7.83-7.87 (m, 1H), 7.93-7.97 (m, 1H), 8.15-8.19 (m, 1H), 8.33 (s, 1H), 8.95 (s, 1H), 9.31 (s, 1H).

2-Ethylsulphonyl-3-[3-methyl-6-(trifluoromethyl)imidazo[4,5-c]pyridin-2-yl]quinoxaline (I-3)

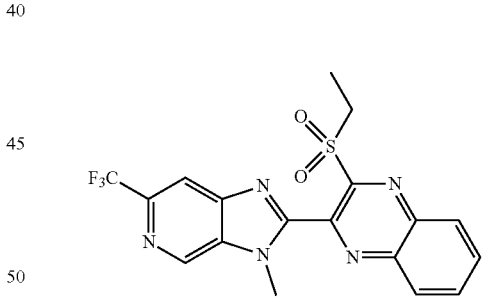

160.7 mg (0.41 mmol) of 3-ethylsulphanyl-2-[3-methyl-6-(trifluoromethyl)imidazo[4,5-c]pyridin-2-yl]quinoxaline were dissolved in 10 ml of dichloromethane, 195.1 mg (0.82 mmol) of meta-chloroperbenzoic acid were added at 0° C., and the mixture was stirred at 0° C. for 5 min and at room temperature for 2 h. The mixture was admixed with sodium bisulphite solution, stirred for 1 h, diluted with 20 ml of water and adjusted to pH 9-10 with 45% sodium hydroxide solution. Then the mixture was extracted three times with dichloromethane and then the combined organic phases were freed of the solvent under reduced pressure.

(log P (neutral): 2.45; MH$^+$: 422; $^1$H-NMR (400 MHz, D$_6$-DMSO) δ ppm: 1.28 (t, 3H), 3.82 (q, 2H), 4.00 (s, 3H), 8.22-8.26 (m, 2H), 8.33 (s, 1H), 8.38-8.40 (m, 1H), 8.45-8.47 (m, 1H), 9.32 (s, 1H).

2-Ethylsulphanyl-3-[3-methyl-6-(trifluoromethyl)imidazo[4,5-c]pyridin-2-yl]quinoxaline (I-4)

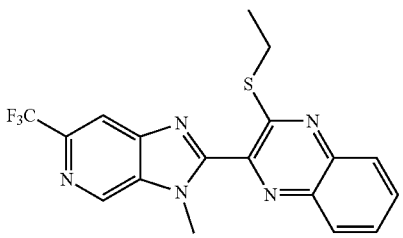 [SMILES: CCSc1nc2ccccc2nc1-c1nc2cc(C(F)(F)F)ncc2n1C]

280 mg (0.66 mmol) of 2-chloro-3-[3-methyl-6-(trifluoromethyl)imidazo[4,5-c]pyridin-2-yl]quinoxaline and 111.4 mg (1.32 mmol) of sodium ethanethiolate were stirred in 8 ml of DMF at room temperature under argon for 30 min. Water was added and the mixture was extracted twice with ethyl acetate. The combined organic phases were washed with a sodium chloride solution, removed, dried over sodium sulphate and freed of the solvent under reduced pressure. The residue was purified by column chromatography purification with a cyclohexane/ethyl acetate gradient as eluent.

(log P (neutral): 4.10; MH$^+$: 390; $^1$H-NMR (400 MHz, D$_6$-DMSO) δ ppm: 1.37 (t, 3H), 3.31 (q, 2H), 4.18 (s, 3H), 7.85 (t, 1H), 7.96 (t, 1H), 8.08 (d, 1H), 8.16 (d, 1H), 8.37 (s, 1H), 9.33 (s, 1H).

2-Chloro-3-[3-methyl-6-(trifluoromethyl)imidazo[4,5-c]pyridin-2-yl]quinoxaline (V-2)

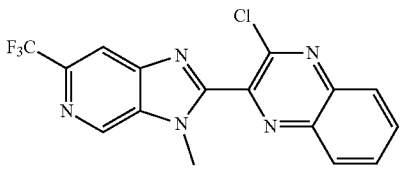 [SMILES: Cn1c(-c2nc3ccccc3nc2Cl)nc2cc(C(F)(F)F)ncc21]

385 mg (2.01 mmol) of N$^3$-methyl-6-(trifluoromethyl)pyridine-3,4-diamine, 504 mg (2.41 mmol) of 3-chloroquinoxaline-2-carboxylic acid and 386 mg (2.01 mmol) of 1-(3-dimethylaminopropyl)-3-ethylcarbodiimide hydrochloride (EDCI) were stirred in 10 ml of pyridine at room temperature for 18 h. The reaction mixture was freed of the solvent under reduced pressure, then water was added and the mixture was extracted three times with ethyl acetate. The combined organic phases were dried over sodium sulphate and concentrated again.

The residue was dissolved in 5 ml of toluene, 181.3 mg (0.95 mmol) of para-toluenesulphonic acid were added, and the mixture was stirred at 120° C. for 2 h. Subsequently, the reaction mixture was admixed with saturated sodium hydrogencarbonate solution and extracted twice with ethyl acetate. The combined organic phases were dried over sodium sulphate and freed of the solvent under reduced pressure.

(log P (neutral): 2.84; MH$^+$: 364; $^1$H-NMR (400 MHz, D$_6$-DMSO) δ ppm: 4.12 (s, 3H), 8.03-8.13 (m, 2H), 8.22-8.31 (m, 2H), 8.37 (s, 1H), 9.33 (s, 1H).

6-(3-Ethylsulphonyl-2-quinolyl)-2,2-difluoro-7-methyl-[1,3]dioxolo[4,5-f]benzimidazole

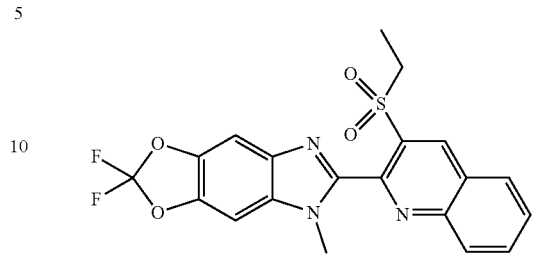

13 mg (0.03 mmol) of 6-(3-ethylsulphonyl-2-quinolyl)-2,2-difluoro-5H-[1,3]dioxolo[4,5-f]benzimidazole, 4.9 mg (0.03 mmol) of methyl iodide and 8.6 mg (0.06 mmol) of potassium carbonate were dissolved in 3 ml of acetone and stirred under reflux for 3 h. The reaction mixture was filtered off, the mother liquor was freed of the solvent, the residue was taken up in dichloromethane, washed with water, dried over sodium sulphate and then the solvent was distilled off under reduced pressure.

(log P (neutral): 3.39; MH$^+$: 432; $^1$H-NMR (400 MHz, D$_6$-DMSO) δ ppm: 1.23 (t, 3H), 3.76 (s, 3H), 3.90 (q, 2H), 7.80 (s, 1H), 7.91 (s, 1H), 7.93 (t, 1H), 8.12 (t, 1H), 8.25 (d, 1H), 8.47 (d, 1H), 9.28 (s, 1H).

6-(3-Ethylsulphonyl-2-quinolyl)-2,2-difluoro-5H-[1,3]dioxolo[4,5-f]benzimidazole

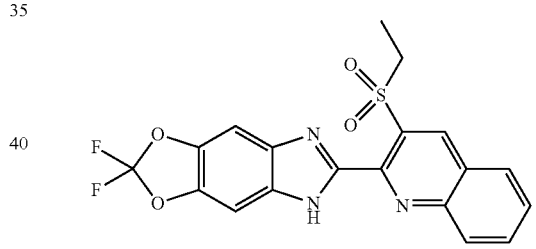

26 mg (0.06 mmol) of 6-(3-ethylsulphanyl-2-quinolyl)-2,2-difluoro-5H-[1,3]dioxolo[4,5-f]benzimidazole were dissolved in 3 ml of dichlormethane, 9.2 mg (0.20 mmol) of formic acid and 45.4 mg (0.46 mmol) of 35% hydrogen peroxide were added at room temperature, and then the mixture was stirred at room temperature for 4 h. Subsequently, 3 further equivalents of formic acid and 7 equivalents of 35% hydrogen peroxide were added and the mixture was stirred at room temperature for a further 2 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane, and the combined organic phases were then freed of the solvent under reduced pressure. The residue was purified by column chromatography purification with a cyclohexane/ethyl acetate gradient (70:30 to 30:70) as eluent.

(log P (neutral): 3.37; MH$^+$: 418; $^1$H-NMR (400 MHz, D$_6$-DMSO) δ ppm: 1.30 (t, 3H), 4.31 (q, 2H), 7.63 (br. s, 1H), 7.80 (br. s, 1H), 7.89 (t, 1H), 8.10 (t, 1H), 8.24 (d, 1H), 8.43 (d, 1H), 9.27 (s, 1H), 13.54 (s, 1H).

6-(3-Ethylsulphanyl-2-quinolyl)-2,2-difluoro-5H-[1,3]dioxolo[4,5-f]benzimidazole

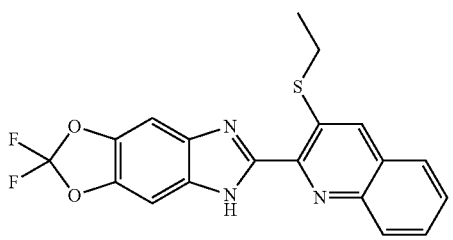 [SMILES: CCSc1cc2ccccc2nc1-c1nc2cc3c(cc2[nH]1)OC(F)(F)O3]

590 mg (2.97 mmol) of 2,2-difluoro-1,3-benzodioxole-5,6-diamine, 926.7 mg (3.57 mmol) of 3-ethylsulphanylquinoline-2-carboxylic acid, 576.9 mg (2.97 mmol) of 1-(3-dimethylaminopropyl)-3-ethylcarbodiimide hydrochloride (EDCI) and 4.4 mg of molecular sieve (4 A) were stirred in 30 ml of pyridine under argon at 120° C. for 8 h. The reaction mixture was freed of solvent under reduced pressure, and the residue was taken up in ethyl acetate and washed with water. The aqueous phase was extracted twice with ethyl acetate, the organic phases were combined and dried over sodium sulphate, and then the solvent was distilled off under reduced pressure. The residue was stirred at reflux in 30 ml of phosphoryl chloride for 4 h and then the solvent was removed again under reduced pressure. The residue was taken up in dichloromethane, washed with water and dried over sodium sulphate, and then the solvent was distilled off under reduced pressure. The residue was purified by column chromatography purification with a cyclohexane/ethyl acetate gradient (70:30 to 0:100) as eluent.

(log P (neutral): 4.26; MH+: 386; $^1$H-NMR (400 MHz, D$_6$-DMSO) δ ppm: 1.39 (t, 3H), 3.14 (q, 2H), 7.56 (br. s, 1H), 7.66 (t, 1H), 7.76 (t, 1H), 7.84 (br. s, 1H), 8.02 (d, 1H), 8.07 (d, 1H), 8.37 (s, 1H), 13.31 (s, 1H).

2-(3-Ethylsulphonyl-2-quinolyl)-5-(trifluoromethylsulphonyl)-1,3-benzoxazole

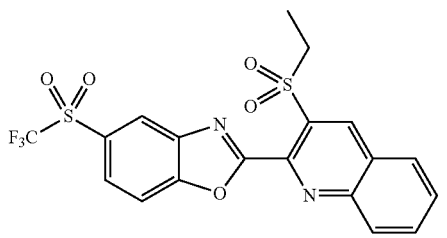 [SMILES: CCS(=O)(=O)c1cc2ccccc2nc1-c1nc2cc(S(=O)(=O)C(F)(F)F)ccc2o1]

103 mg (0.06 mmol) of 2-(3-ethylsulphonyl-2-quinolyl)-5-(trifluoromethylsulphanyl)-1,3-benzoxazole were dissolved in 12 ml of dichlormethane, 182 mg (3.93 mmol) of formic acid and 1.81 g (18.59 mmol) of 35% hydrogen peroxide were added at room temperature, and then the mixture was stirred at 40° C. for 72 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane and the combined organic phases were then freed of the solvent under reduced pressure. The residue was purified by column chromatography with a dichloromethane/ethyl acetate gradient (0:100 to 40:60) as eluent.

(log P (neutral): 3.62; MH+: 471; $^1$H-NMR (400 MHz, D$_6$-DMSO) δ ppm: 1.33 (t, 3H), 4.00 (q, 2H), 8.00 (t, 1H), 8.18 (t, 1H), 8.32-8.37 (m, 2H), 8.45 (d, 1H), 8.51 (d, 1H), 8.87 (s, 1H), 9.40 (s, 1H).

2-(3-Ethylsulphonyl-2-quinolyl)-5-(trifluoromethylsulphinyl)-1,3-benzoxazole

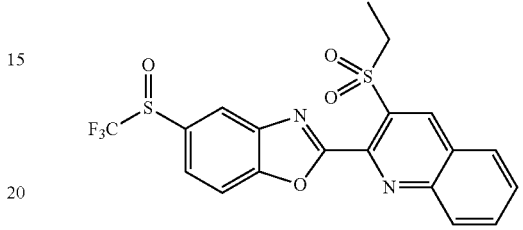

The same method as described for the synthesis of 2-(3-ethylsulphonyl-2-quinolyl)-5-(trifluoromethylsulphonyl)-1,3-benzoxazole was also used to obtain the corresponding trifluoromethylsulphoxide derivative 2-(3-ethylsulphonyl-2-quinolyl)-5-(trifluoromethylsulphinyl)-1,3-benzoxazole.

(log P (neutral): 3.05; MH+: 455; $^1$H-NMR (400 MHz, D$_6$-DMSO) δ ppm: 1.32 (t, 3H), 3.99 (q, 2H), 7.99 (t, 1H), 8.11-8.18 (m, 2H), 8.32-8.34 (m, 2H), 8.50 (d, 1H), 8.55 (s, 1H), 9.38 (s, 1H).

2-(3-Ethylsulphonyl-2-quinolyl)-5-(trifluoromethylsulphanyl)-1,3-benzoxazole

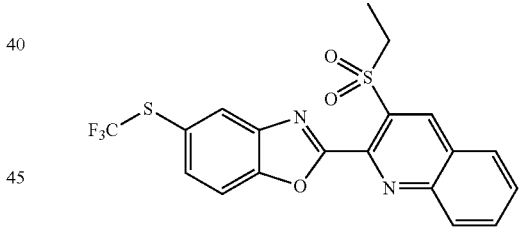

244 mg (0.57 mmol) of 2-(3-ethylsulphanyl-2-quinolyl)-5-(trifluoromethylsulphanyl)-1,3-benzoxazole were dissolved in 16 ml of dichloromethane, 157.5 mg (3.42 mmol) of formic acid and 554.0 mg (5.7 mmol) of 35% hydrogen peroxide were added at room temperature, and then the mixture was stirred at room temperature for 6 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane and the combined organic phases were then freed of the solvent under reduced pressure. The residue was purified by column chromatography purification with a cyclohexane/ethyl acetate gradient (70:30 to 0:100) as eluent.

(log P (neutral): 4.17; MH+: 439; $^1$H-NMR (400 MHz, D$_6$-DMSO) δ ppm: 1.32 (t, 3H), 3.98 (q, 2H), 7.93-8.00 (m, 2H), 8.13-8.18 (m, 2H), 8.31 (d, 1H), 8.40 (s, 1H), 8.50 (d, 1H), 9.37 (s, 1H).

2-(3-Ethylsulphanyl-2-quinolyl)-5-(trifluoromethylsulphanyl)-1,3-benzoxazole

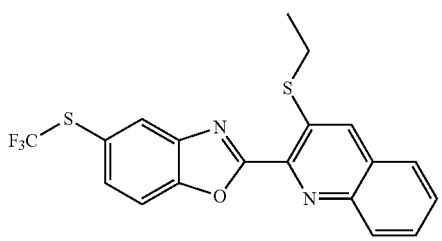 [SMILES: CCSc1cc2ccccc2nc1-c1nc2cc(SC(F)(F)F)ccc2o1]

446 mg (2.02 mmol) of 2-amino-4-(trifluoromethylsulphanyl)phenol, 708.8 mg (2.43 mmol) of 3-ethylsulphanylquinoline-2-carboxylic acid and 465.9 mg (2.97 mmol) of 1-(3-dimethylaminopropyl)-3-ethylcarbodiimide hydrochloride (EDCI) were stirred in 20 ml of pyridine under argon at 80° C. for 4 h. The reaction mixture was freed of the solvent under reduced pressure and the residue was purified by column chromatography purification with cyclohexane/ethyl acetate as eluent.

540 mg (1.17 mmol) of the 3-ethyl sulphanyl-N-[2-hydroxy-5-(trifluoromethylsulphanyl)phenyl]quinoline-2-carboxamide intermediate prepared in this way were stirred in 30 ml of tetrahydrofuran in the presence of 409 mg (1.68 mmol) of di-2-methoxyethyl azodicarboxylate (DMEAD) and 434 mg of triphenylphospine at room temperature for 1 h and at 50° C. for 1 h. Subsequently, the reaction mixture was freed of the solvent under reduced pressure and the residue was purified by column chromatography purification with a cyclohexane/ethyl acetate gradient (80:20 to 40:60) as eluent.

(log P (neutral): 5.43; MH$^+$: 407; $^1$H-NMR (400 MHz, D$_6$-DMSO) δ ppm: 1.38 (t, 3H), 3.21 (q, 2H), 7.73-7.82 (m, 2H), 7.90 (d, 1H), 8.07-8.15 (m, 3H), 8.41 (s, 1H), 8.54 (s, 1H).

3-Ethylsulphonyl-2-[1-methyl-5-(trifluoromethylsulphonyl)benzimidazol-2-yl]quinoline

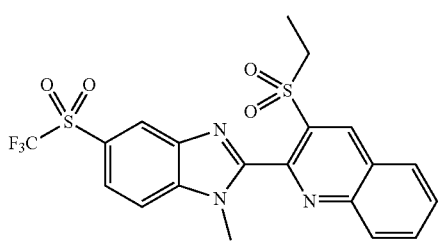 [SMILES: CCS(=O)(=O)c1cc2ccccc2nc1-c1nc2cc(S(=O)(=O)C(F)(F)F)ccc2n1C]

71 mg (0.15 mmol) of 3-ethylsulphonyl-2-[1-methyl-5-(trifluoromethylsulphinyl)benzimidazol-2-yl]quinoline were dissolved in 6 ml of acetonitrile, 10.0 mg (0.02 mmol) of sodium tungstate(VI) dihydrate and 738.0 mg (7.58 mmol) of 35% hydrogen peroxide were added at room temperature, and then the mixture was stirred at reflux for 24 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane and the combined organic phases were then freed of the solvent under reduced pressure. The residue was purified by column chromatography purification with a dichloromethane/ethyl acetate gradient (70:30 to 0:100) as eluent.

(log P (neutral): 3.42; MH$^+$: 484; $^1$H-NMR (400 MHz, D$_6$-DMSO) δ ppm: 1.24 (t, 3H), 3.87 (q, 2H), 3.89 (s, 3H), 7.97 (t, 1H), 8.10-8.28 (m, 4H), 8.50 (d, 1H), 8.56 (s, 1H), 9.34 (s, 1H).

3-Ethylsulphonyl-2-[1-methyl-5-(trifluoromethylsulphinyl)benzimidazol-2-yl]quinoline

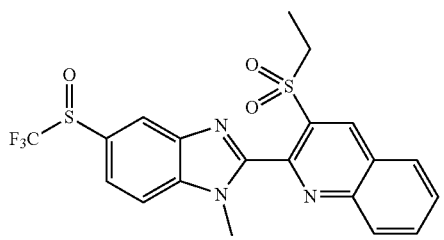 [SMILES: CCS(=O)(=O)c1cc2ccccc2nc1-c1nc2cc(S(=O)C(F)(F)F)ccc2n1C]

262 mg (0.62 mmol) of 3-ethylsulphanyl-2-[1-methyl-5-(trifluoromethylsulphanyl)benzimidazol-2-yl]quinoline were dissolved in 6 ml of dichloromethane, 143.7 mg (3.12 mmol) of formic acid and 424.9 mg (4.37 mmol) of 35% hydrogen peroxide were added at room temperature, and then the mixture was stirred at room temperature for 4 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane and the combined organic phases were then freed of the solvent under reduced pressure. The residue was purified by column chromatography purification with a cyclohexane/ethyl acetate gradient (80:20 to 0:100) as eluent.

(log P (neutral): 2.79; MH$^+$: 468; $^1$H-NMR (400 MHz, D$_6$-DMSO) δ ppm: 1.24 (t, 3H), 3.85 (s, 1H), 3.90 (q, 2H), 7.91-7.97 (m, 2H), 8.10-8.15 (m, 2H), 8.26 (d, 1H), 8.34 (s, 1H), 8.50 (d, 1H), 9.32 (s, 1H).

3-Ethylsulphonyl-2-[1-methyl-5-(trifluoromethylsulphanyl)benzimidazol-2-yl]quinoline

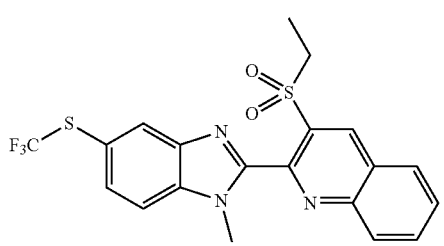 [SMILES: CCS(=O)(=O)c1cc2ccccc2nc1-c1nc2cc(SC(F)(F)F)ccc2n1C]

The same method as described for the synthesis of 3-ethylsulphonyl-2-[1-methyl-5-(trifluoromethylsulphinyl)benzimidazol-2-yl]quinoline was also used to obtain the corresponding trifluoromethylsulphide derivative 3-ethylsulphonyl-2-[1-methyl-5-(trifluoromethylsulphanyl) benzimidazol-2-yl]quinoline.

(log P (neutral): 3.96; MH$^+$: 452; $^1$H-NMR (400 MHz, D$_6$-DMSO) δ ppm: 1.23 (t, 3H), 3.80 (s, 1H), 3.90 (q, 2H), 7.71 (d, 1H), 7.90-7.97 (m, 2H), 8.11-8.15 (m, 2H), 8.26 (d, 1H), 8.49 (d, 1H), 9.31 (s, 1H).

3-Ethylsulphanyl-2-[1-methyl-5-(trifluoromethylsulphanyl)benzimidazol-2-yl]quinoline

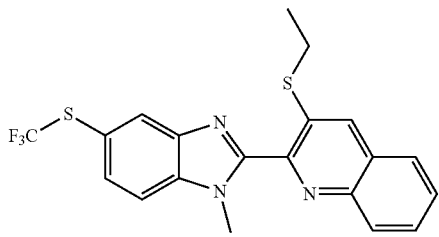 [SMILES: CCSc1cc2ccccc2nc1-c1nc2cc(SC(F)(F)F)ccc2n1C]

806 mg (3.37 mmol) of N1-methyl-4-(trifluoromethylsulphanyl)phenylene-1,2-diamine, 966.5 mg (4.04 mmol) of 3-ethylsulphanylquinoline-2-carboxylic acid, 673.0 mg (3.37 mmol) of 1-(3-dimethylaminopropyl)-3-ethylcarbodiimide hydrochloride (EDCI) and 4 mg of molecular sieve (4 A) were stirred in 30 ml of pyridine under argon at 120° C. for 8 h. The reaction mixture was freed of solvent under reduced pressure, and the residue was taken up in ethyl acetate and washed once with water. The aqueous phase was extracted twice with ethyl acetate, the combined organic phases were dried over sodium sulphate and the solvent was then distilled off under reduced pressure. The residue was purified by column chromatography purification with a water/acetonitrile gradient plus 0.1 ml/l formic acid as eluent.

(log P (neutral): 4.63; MH$^+$: 420; $^1$H-NMR (400 MHz, D$_6$-DMSO) δ ppm: 1.27 (t, 3H), 3.11 (q, 2H), 3.91 (s, 1H), 7.69-7.80 (m, 4H), 7.89 (d, 1H), 8.07 (d, 1H), 8.16 (s, 1H), 8.53 (s, 1H).

2-(3-Ethylsulphonyl-2-quinolyl)-6-methyloxazolo[5,4-b]pyridine

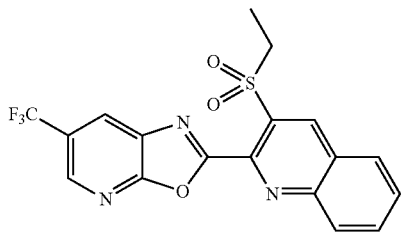 [SMILES: CCS(=O)(=O)c1cc2ccccc2nc1-c1nc2cc(C(F)(F)F)cnc2o1]

86 mg (0.21 mmol) of 2-(3-ethylsulphanyl-2-quinolyl)-6-methyloxazolo[5,4-b]pyridine were dissolved in 6 ml of dichlormethane, 49.6 mg (1.07 mmol) of formic acid and 188.4 mg (1.93 mmol) of 35% hydrogen peroxide were added at room temperature, and then the mixture was stirred at room temperature for 7 h. The reaction mixture was diluted with water and admixed with sodium bisulphite solution, stirred for 30 min, and then admixed with saturated sodium hydrogencarbonate solution. The organic phase was separated off, the aqueous phase was extracted twice with dichloromethane and the combined organic phases were then freed of the solvent under reduced pressure. The residue was purified by column chromatography purification with a cyclohexane/ethyl acetate gradient (80:20 to 0:100) as eluent.

(log P (neutral): 3.27; MH$^+$: 408; $^1$H-NMR (400 MHz, D$_6$-DMSO) δ ppm: 1.32 (t, 3H), 3.93 (q, 2H), 8.00 (t, 1H), 8.18 (t, 1H), 8.35 (d, 1H), 8.51 (d, 1H), 9.03 (s, 1H), 9.04 (s, 1H), 9.40 (s, 1H).

2-(3-Ethylsulphinyl-2-quinolyl)-6-methyloxazolo[5,4-b]pyridine

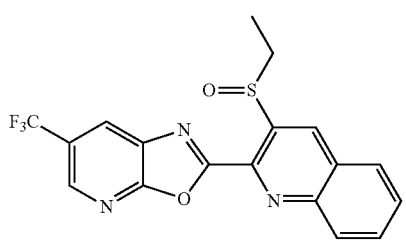 [SMILES: CCS(=O)c1cc2ccccc2nc1-c1nc2cc(C(F)(F)F)cnc2o1]

The same method as described for the synthesis of 2-(3-ethylsulphonyl-2-quinolyl)-6-methyloxazolo[5,4-b]pyridine was also used to obtain the corresponding sulphoxide derivative 2-(3-ethylsulphinyl-2-quinolyl)-6-methyloxazolo[5,4-b]pyridine.

(log P (neutral): 2.98; MH$^+$: 492; $^1$H-NMR (400 MHz, D$_6$-DMSO) δ ppm: 1.25 (t, 3H), 2.93-3.02 (m, 1H), 3.47-3.56 (m, 1H), 7.90 (t, 1H), 8.05 (t, 1H), 8.37-8.41 (m, 2H), 8.99 (s, 1H), 9.03 (s, 1H), 9.10 (s, 1H).

2-(3-Ethylsulphanyl-2-quinolyl)-6-methyloxazolo[5,4-b]pyridine

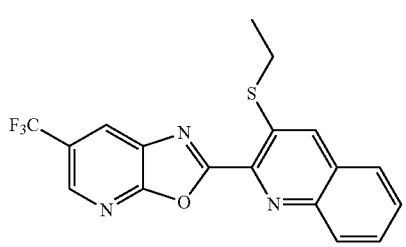 [SMILES: CCSc1cc2ccccc2nc1-c1nc2cc(C(F)(F)F)cnc2o1]

172 mg (0.36 mmol) of N-(2-chloro-5-methyl-3-pyridyl)-3-ethylsulphanylquinoline-2-carboxamide were dissolved in 6 ml of dimethylformamide, 38.9 mg (0.36 mmol) of sodium carbonate were added and the mixture was stirred at 145° C. for 4 h. The mixture was added to ice-water and extracted twice with ethyl acetate, the combined organic phases were washed with water and dried over sodium sulphate, and the solvent was distilled off under reduced pressure. The residue was purified by column chromatography purification with a cyclohexane/ethyl acetate gradient as eluent.

(log P (neutral): 4.36; MH$^+$: 376; $^1$H-NMR (400 MHz, D$_6$-DMSO) δ ppm: 1.38 (t, 3H), 3.22 (q, 2H), 7.75-7.85 (m, 2H), 8.09 (d, 1H), 8.17 (d, 1H), 8.55 (s, 1H), 8.97 (s, 1H), 9.01 (s, 1H).

N-(2-Chloro-5-methyl-3-pyridyl)-3-ethylsulpha-nylquinoline-2-carboxamide (IV-1)

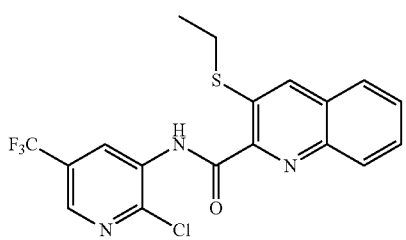 [SMILES: CCSc1cc2ccccc2nc1C(=O)Nc1cc(C(F)(F)F)cnc1Cl]

240 mg (1.19 mmol) of 2-chloro-5-(trifluoromethyl)pyridin-3-amine and 357 mg (1.31 mmol) of 3-ethylsulphanylquinoline-2-carboxylic acid were dissolved together with 0.39 ml (4.78 mmol) of pyridine in 20 ml of dioxane, 367 mg (2.39 mmol) of phosphoryl chloride were added, and the mixture was stirred at reflux for 90 min. The mixture was concentrated, the residue was taken up in ethyl acetate and washed with water, and the aqueous phase was extracted twice with ethyl acetate. The combined organic phases were dried over sodium sulphate and the solvent was distilled off under reduced pressure. The residue was purified by column chromatography purification with a cyclohexane/ethyl acetate gradient (80:20 to 40:60) as eluent.

(log P (neutral): 5.71; MH$^+$: 412; $^1$H-NMR (400 MHz, D$_6$-DMSO) δ ppm: 1.37 (t, 3H), 3.12 (q, 2H), 7.74-7.84 (m, 2H), 8.07-8.14 (m, 2H), 8.49 (s, 1H), 8.70 (s, 1H), 9.02 (s, 1H), 11.12 (s, 1H).

3-(Ethylsulphonyl)-2-[7-(trifluoromethyl)imidazo[1,2-c]pyrimidin-2-yl]quinoline

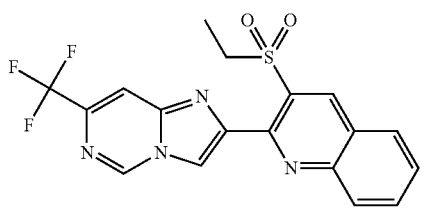 [SMILES: CCS(=O)(=O)c1cc2ccccc2nc1-c1cn2cnc(C(F)(F)F)cc2n1]

3-(Ethylsulphanyl)-2-[7-(trifluoromethyl)imidazo[1,2-c]pyrimidin-2-yl]quinoline (24 mg, 0.06 mmol) was dissolved in 2 ml of dichloromethane. Hydrogen peroxide (35% aqueous solution, 43 mg, 0.44 mmol) and formic acid (15 mg, 0.32 mmol) were added and the reaction mixture was stirred for 12 h. While cooling with ice, 1 ml of 40% sodium bisulphite solution was added dropwise and the mixture was stirred for 1 h. The phases were separated, and the organic phase was washed with sodium hydrogencarbonate solution, dried over sodium sulphate and concentrated on a rotary evaporator. The residue was purified by chromatography (eluent: cyclohexane, ethyl acetate).

log P (neutral): 2.63; MH$^+$: 407; $^1$H-NMR (400 MHz, D$_6$-DMSO) δ ppm: 9.70 (s, 1H), 9.23 (s, 1H), 8.74 (s, 1H), 8.41-8.39 (m, 2H), 8-21-8.19 (m, 1H), 8.08-8.04 (m, 1H), 7.87-7.83 (m, 1H), 4.17-4.12 (m, 2H), 1.30-1.27 (m, 3H).

3-(Ethylsulphanyl)-2-[7-(trifluoromethyl)imidazo[1,2-c]pyrimidin-2-yl]quinoline

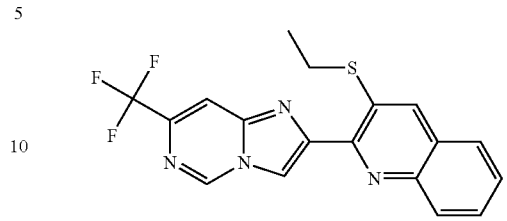

2-Bromo-1-[3-(ethylsulphanyl)quinolin-2-yl]ethanone (453 mg, 0.92 mmol) and 6-(trifluoromethyl)pyrimidin-4-amine (150 mg, 0.92 mmol) were dissolved in 5 ml of tert-butanol, and sodium hydrogencarbonate (386 mg, 4.59 mmol) was added. The reaction mixture was stirred at 80° C. for 5 h. After the solvent had been removed on a rotary evaporator, the residue was purified by chromatography.

log P (neutral): 3.24; MH$^+$: 375; $^1$H-NMR (400 MHz, D$_6$-DMSO) δ ppm: 9.68 (s, 1H), 8.80 (s, 1H), 8.37 (s, 2H), 8.02-7.99 (m, 2H), 7.75-7.70 (m, 1H), 7.66-7.62 (m, 1H), 3.16-3.10 (m, 2H), 1.34-1.30 (m, 3H).

2-Bromo-1-[3-(ethylsulphanyl)quinolin-2-yl]ethanone

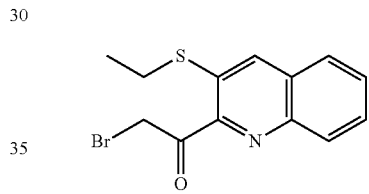

Pyridine hydrobromide perbromide (PyBr$_3$, 100 mg, 0.43 mmol) was dissolved in 4 ml of glacial acetic acid. HBr (32% in glacial acetic acid, 0.15 ml) was added and the mixture was stirred at room temperature for 30 min. Then 1-[3-(ethylsulphanyl)quinolin-2-yl]ethanone (100 mg, 0.43 mmol) dissolved in 1 ml of glacial acetic acid was added dropwise. The reaction mixture was stirred at room temperature for 12 h and then concentrated. The residue was taken up with ethyl acetate and washed with saturated sodium hydrogencarbonate solution and saturated sodium chloride solution. After the organic phase had been dried over sodium sulphate, the solvent was removed on a rotary evaporator. The residue was converted in the subsequent reaction without further purification.

log P (acidic): 3.95; MH$^+$: 312

1-[3-(Ethylsulphanyl)quinolin-2-yl]ethanone

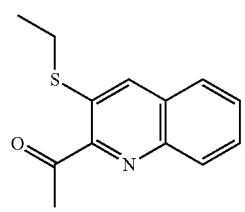 [SMILES: CCSc1cc2ccccc2nc1C(C)=O]

Under an argon atmosphere, 3-(ethylsulphanyl)-N-methoxy-N-methylquinoline-2-carboxamide (2.8 g, 8.1 mmol) was dissolved in 155 ml of dry THF and cooled to 0° C. Methylmagnesium bromide (3M in diethyl ether, 8.1 ml, 24.3 mmol) was slowly added dropwise, then the mixture was stirred for 2 h at 0° C. In order to end the reaction, 5 ml of ammonium chloride solution were added gradually while cooling. The organic phase was separated off and washed with saturated sodium chloride solution. The solvent was removed on a rotary evaporator and the crude product was used in the subsequent reaction without further purification.

log P (neutral): 3.31; MH$^+$: 232; $^1$H-NMR (400 MHz, D$_6$-DMSO) δ ppm: 8.38 (s, 1H), 8.08-8.00 (m, 2H), 7.79-7.70 (m, 2H), 3.10-3.04 (m, 2H), 2.75 (s, 3H), 1.35-1.31 (m, 3H).

3-(Ethylsulphanyl)-N-methoxy-N-methylquinoline-2-carboxamide

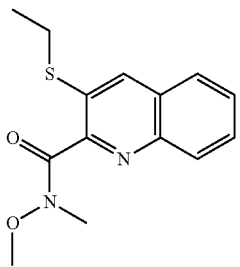 [SMILES: CCSc1cc2ccccc2nc1C(=O)N(C)OC]

3-(Ethylsulphanyl)quinoline-2-carboxylic acid (240 mg, 1.02 mmol) and N,O-dimethylhydroxylamine hydrochloride (100 mg, 1.02 mmol) were dissolved in 3 ml of dichloromethane and cooled to 0° C. 4-Dimethylaminopyridine (DMAP, 150 mg, 1.23 mmol) and N-(dimethylaminopropyl)-N'-ethylcarbodiimide hydrochloride (EDCI, 217 mg, 1.13 mmol) were added and the reaction mixture was stirred for 2 h at 0° C., then for 12 h at room temperature. The solution was washed once with saturated sodium hydrogencarbonate solution and once with sodium chloride solution, dried over sodium sulphate and concentrated. The crude product was used in the subsequent reaction without further purification.

log P (neutral): 2.17; MH$^+$: 277; $^1$H-NMR (400 MHz, D$_6$-DMSO) δ ppm: 8.46 (s, 1H), 8.02-7.98 (m, 2H), 7.78-7.75 (m, 1H), 7.70-7.64 (m, 1H), 3.51 (s, 3H), 3.32 (s, 3H), 3.12-3.05 (m, 2H), 1.28-1.24 (m, 3H).

3-(Ethylsulphanyl)quinoline-2-carboxylic acid

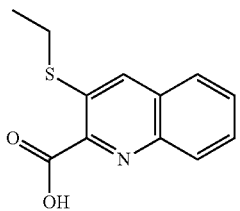 [SMILES: CCSc1cc2ccccc2nc1C(=O)O]

Under an argon atmosphere, 2,2,6,6-tetramethylpiperidine (5.34 g, 38 mmol) was dissolved in 50 ml of dry THF and cooled to −25° C. n-Butyllithium (2.5 M in hexane, 2.44 g, 38.1 mmol, 15.2 ml) was added dropwise and the mixture was stirred at −25° C. for 20 min. Then quinoline-2-carboxylic acid (3.00 g, 17.3 mmol) dissolved in 20 ml of THF was added dropwise and the mixture was stirred at −25° C. for a further 30 min. Diethyl disulphide (5.29 g, 43.3 mmol) was added dropwise and, after stirring at −25° C. for 30 min, the mixture was warmed gradually to room temperature. The reaction mixture was concentrated on a rotary evaporator and the residue was taken up in 100 ml of cyclohexane/diethyl ether (3:7). The remaining solids were isolated by filtration. Water was added, and 2.5 M HCl solution was added until a pH of 4 was obtained. The aqueous solution was extracted three times with dichloromethane. The combined organic extracts were dried over sodium sulphate and the solvent was removed on a rotary evaporator. The crude product was used in the subsequent reaction without further purification.

log P (neutral): 0.48; MH$^+$: 234; $^1$H-NMR (400 MHz, D$_6$-DMSO) δ ppm: 8.43 (s, 1H), 8.03-8.00 (m, 2H), 7.78-7.74 (m, 1H), 7.70-7.67 (m, 1H), 3.13-3.07 (m, 2H), 1.32-1.28 (m, 3H).

3,6-Bis(ethylsulphonyl)-2-[3-methyl-6-(trifluoromethyl)-3H-imidazo[4,5-c]pyridin-2-yl]-1,8-naphthyridine

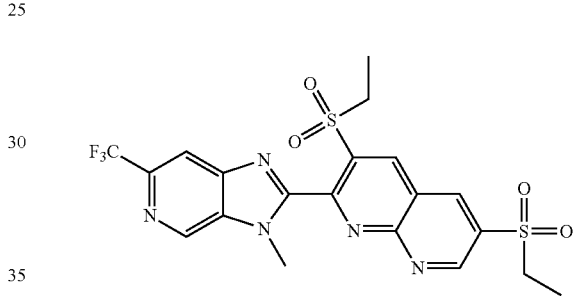

35 mg (0.078 mmol) of 3,6-bis(ethylsulphanyl)-2-[3-methyl-6-(trifluoromethyl)imidazo[4,5-c]pyridin-2-yl]-1,8-naphthyridine were dissolved in 3.5 ml of dichloromethane, 18 mg (0.39 mmol) of formic acid and 53 mg (0.545 mmol) of hydrogen peroxide were added at room temperature, and then the mixture was stirred at room temperature for 18 h. The mixture was freed of the solvent under reduced pressure. The residue was purified by column chromatography purification with a cyclohexane/ethyl acetate gradient as eluent.

log P (neutral): 2.21; MH$^+$: 514; $^1$H-NMR (400 MHz, CD$_3$CN) δ ppm: 1.29 (t, 3H), 1.33 (t, 3H), 3.41 (q, 2H), 3.92 (q, 2H), 4.00 (s, 3H), 8.22 (s, 1H), 9.155 (s, 1H), 9.26 (d, 1H), 9.43 (s, 1H), 9.65 (d, 1H).

3,6-Bis(ethylsulphanyl)-2-[3-methyl-6-(trifluoromethyl)-3H-imidazo[4,5-c]pyridin-2-yl]-1,8-naphthyridine

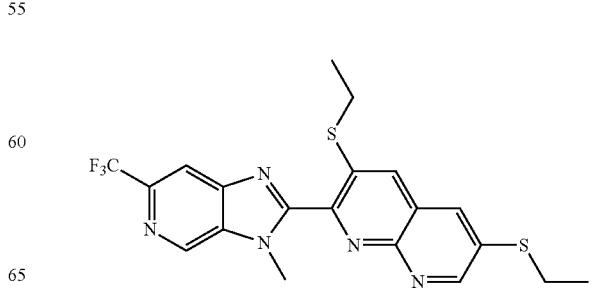

255 mg (0.493 mmol) of 3,6-dichloro-2-[3-methyl-6-(trifluoromethyl)-3H-imidazo[4,5-c]pyridin-2-yl]-1,8-naphthyridine and 156 mg (1.48 mmol) of sodium ethanethiolate were stirred in 14.2 ml of DMF at room temperature under argon for 2 h. Water was added and the mixture was extracted twice with ethyl acetate. The combined organic phases were dried over sodium sulphate and freed of the solvent under reduced pressure. The residue was purified by column chromatography purification with a cyclohexane/ethyl acetate gradient as eluent.

log P (neutral): 3.23; MH+: 450; 1H-NMR (400 MHz, CD3CN) δ ppm: 1.34 (t, 3H), 1.42 (t, 3H), 3.10 (q, 2H), 3.19 (q, 2H), 4.06 (s, 3H), 8.15 (d, 1H), 8.18 (s, 1H), 8.29 (s, 1H), 8.92 (d, 1H), 9.10 (s, 1H).

3,6-Dichloro-2-[3-methyl-6-(trifluoromethyl)-3H-imidazo[4,5-c]pyridin-2-yl]-1,8-naphthyridine (V-3)

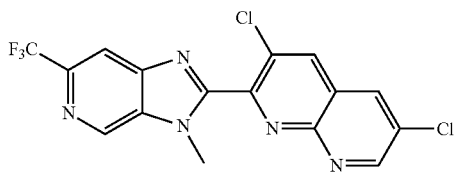 [SMILES: Cn1c(-c2nc3ncc(Cl)cc3cc2Cl)nc2cc(C(F)(F)F)ncc21]

310 mg (1.62 mmol) of N3-methyl-6-(trifluoromethyl)pyridine-3,4-diamine, 512 mg (2.11 mmol) of 3,6-dichloro-1,8-naphthyridine-2-carboxylic acid and 622 mg (3.24 mmol) of 1-(3-dimethylaminopropyl)-3-ethylcarbodiimide hydrochloride (EDCI) were stirred in 18 ml of pyridine at 120° C. for 18 h. 140 mg (0.811 mmol) of para-toluenesulphonic acid were added and the reaction mixture was stirred at 120° C. for 18 h. The mixture was diluted with acetonitrile, filtered and freed of the solvent under reduced pressure. The residue was purified by column chromatography purification with a dichloromethane/methanol gradient as eluent.

log P (neutral): 2.44; MH+: 398; 1H-NMR (400 MHz, CD3CN) δ ppm: 4.03 (s, 3H), 8.22 (s, 1H), 8.48 (d, 1H), 8.65 (s, 1H), 9.13 (s, 2H).

3,6-Dichloro-1,8-naphthyridine-2-carboxylic acid (III-1)

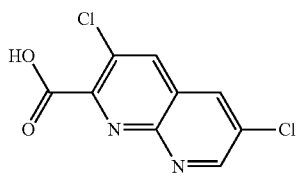

990 mg (3.85 mmol) of methyl 3,6-dichloro-1,8-naphthyridine-2-carboxylate and 184 mg (7.70 mmol) of lithium hydroxide were stirred in 6.9 ml of tetrahydrofuran and 2.3 ml of water at room temperature for 18 h. An aqueous 1 N chloric acid solution was added, and the mixture was freed of the solvent under reduced pressure. Toluene was twice added to the residue and the mixture was freed of the solvent under reduced pressure.

log P (acidic): 0.70; MH+: 243; 1H-NMR (400 MHz, CD3CN) δ ppm: 8.39 (m, 1H), 8.49 (s, 1H), 9.07 (m, 1H).

Methyl 3,6-dichloro-1,8-naphthyridine-2-carboxylate (XXXI-1)

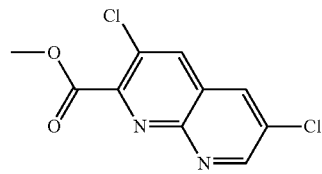

2.37 g (12.6 mmol) of methyl 1,8-naphthyridine-2-carboxylate and 1.93 g (14.5 mmol) of N-chlorosuccinimide were stirred in 118 ml of acetonitrile at 60° C. for 18 h. The mixture was freed of the solvent under reduced pressure. The residue was purified by column chromatography purification with an ethyl acetate/methanol gradient as eluent.

log P (neutral): 1.93; MH+: 257; 1H-NMR (400 MHz, CD3CN) δ ppm: 4.01 (s, 3H), 8.71 (d, 1H), 8.845 (s, 1H), 9.20 (d, 1H).

Methyl 1,8-naphthyridine-2-carboxylate (XXII-1)

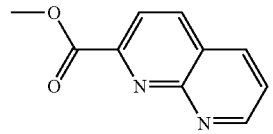

600 mg (3.44 mmol) of 1,8-naphthyridine-2-carboxylic acid and 0.754 ml (10.3 mmol) of thionyl chloride were stirred in 15 ml of methanol at 60° C. for 6 h. The mixture was freed of the solvent under reduced pressure. Methyl tert-butyl ether was added to the residue and the mixture was freed of the solvent under reduced pressure.

log P (neutral): 0.77; MH+: 189; 1H-NMR (400 MHz, CD3CN) δ ppm: 4.00 (s, 3H), 7.84 (dd, 1H), 8.27 (d, 1H), 8.70 (dd, 1H), 8.76 (d, 1H), 9.28 (m, 1H).

1,8-Naphthyridine-2-carboxylic acid (XXX-1)

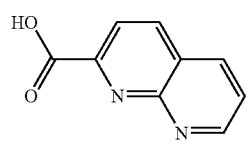

3.00 g (24.6 mmol) of 2-aminonicotinaldehyde and 4.44 ml (49.1 mmol) of methyl pyruvate were stirred in 30 ml of ethanol and 5.0 ml of water at 0° C. 30 ml (90.0 mmol) of an aqueous 3 N sodium hydroxide solution were added and the reaction mixture was stirred at RT for 18 h. The mixture was adjusted to pH=1 at 0° C. with about 50 ml of an aqueous 1 N chloric acid solution, freed of ethanol under reduced pressure and filtered.

log P (acidic): −0.12; MH+: 175; 1H-NMR (400 MHz, CD3CN) δ ppm: 7.72 (dd, 1H), 8.30 (d, 1H), 8.495 (dd, 1H), 8.62 (d, 1H), 9.22 (m, 1H).

Methyl 3,6-dichloro-1,5-naphthyridine-2-carboxylate (XXXI-2)

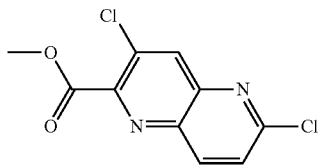

1.07 g (5.69 mmol) of methyl 1,5-naphthyridine-2-carboxylate and 873 mg (6.54 mmol) of N-chlorosuccinimide were stirred in 100 ml of acetonitrile at 60° C. for 18 h. The mixture was freed of the solvent under reduced pressure. The residue was purified by column chromatography purification with an ethyl acetate/methanol gradient as eluent.

log P (neutral): 2.46; MH$^+$: 257; $^1$H-NMR (400 MHz, CD$_3$CN) δ ppm: 4.02 (s, 3H), 8.49 (m, 1H), 8.61 (s, 1H), 9.01 (d, 1H).

Methyl 1,5-naphthyridine-2-carboxylate (XXII-2)

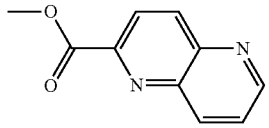

1.00 g (5.74 mmol) of 1,5-naphthyridine-2-carboxylic acid and 1.26 ml (17.2 mmol) of thionyl chloride were stirred in 15 ml of methanol at 60° C. for 6 h. The mixture was freed of the solvent under reduced pressure. Methyl tert-butyl ether was added to the residue and the mixture was freed of the solvent under reduced pressure.

log P (neutral): 0.92; MH$^+$: 189; $^1$H-NMR (400 MHz, CD$_3$CN) δ ppm: 4.04 (s, 3H), 8.19 (dd, 1H), 8.57 (d, 1H), 9.06 (dd, 1H), 9.15-9.19 (m, 2H).

7-Chloro-3-ethylsulphonyl-2-[3-methyl-6-(trifluoromethyl)imidazo[4,5-c]pyridin-2-yl]quinoline

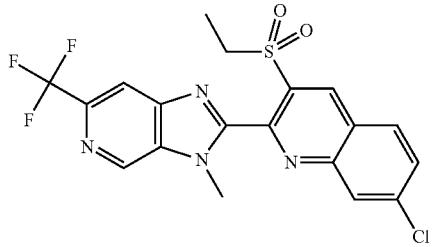 [SMILES: CCS(=O)(=O)c1cc2ccc(Cl)cc2nc1-c1nc2cc(C(F)(F)F)ncc2n1C]

6-Chloro-3-ethylsulphanyl-2-[3-methyl-6-(trifluoromethyl)imidazo[4,5-c]pyridin-2-yl]quinoline (250 mg, 0.59 mmol, mixture with bissulphide) was dissolved in dichloromethane (20 ml), and then formic acid (136 mg, 2.95 mmol) and H$_2$O$_2$ (402 mg, 4.13 mmol) were added. The mixture was stirred at RT for 14 h and washed with sodium thiosulphate solution. The organic phase was removed, dried over Na$_2$SO$_4$ and concentrated. The solids were triturated with MeCN, filtered off and dried under reduced pressure, giving the title compound as a clean product.

(log P (neutral): 2.63; MH$^+$: 455; $^1$H-NMR (400 MHz, CDCl$_3$): δ 9.05 (s, 1H), 8.79 (s, 1H), 8.57 (s, 1H), 8.23 (dd, 1H), 8.14 (d, 1H), 8.12 (d, 1H), 4.11 (s, 3H), 3.26 (q, 2H), 1.34 (t, 3H).

3,6-Bis(ethylsulphonyl)-2-[3-methyl-6-(trifluoromethyl)imidazo[4,5-c]pyridin-2-yl]quinoline

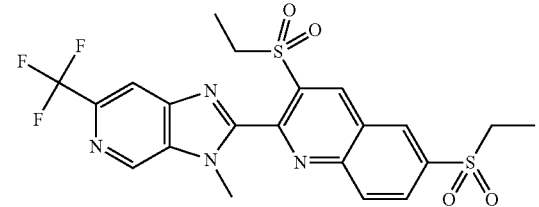 [SMILES: CCS(=O)(=O)c1ccc2nc(-c3nc4cc(C(F)(F)F)ncc4n3C)c(S(=O)(=O)CC)cc2c1]

3,6-Bis(ethylsulphanyl)-2-[3-methyl-6-(trifluoromethyl)imidazo[4,5-c]pyridin-2-yl]quinoline (25 mg, 0.05 mmol) was dissolved in dichloromethane (5 ml), and then formic acid (13 mg, 0.27 mmol) and H$_2$O$_2$ (38 mg, 0.39 mmol) were added. The mixture was stirred at RT for 14 h and washed with sodium thiosulphate solution. The organic phase was removed, dried over Na$_2$SO$_4$ and concentrated, giving the title compound as a clean product.

(log P (neutral): 2.58; MH$^+$: 513; $^1$H-NMR (400 MHz, CDCl$_3$): δ 9.25 (s, 1H), 9.05 (s, 1H), 8.79 (d, 1H), 8.44 (m, 1H), 8.42 (m, 1H), 8.15 (s, 1H), 4.00 (s, 3H), 3.91 (q, 2H), 3.29 (q, 2H), 1.42 (t, 3H), 1.38 (t, 3H).

6-Chloro-3-ethylsulphanyl-2-[3-methyl-6-(trifluoromethyl)imidazo[4,5-c]pyridin-2-yl]quinoline &
3,6-bis(ethylsulphanyl)-2-[3-methyl-6-(trifluoromethyl)imidazo[4,5-c]pyridin-2-yl]quinoline

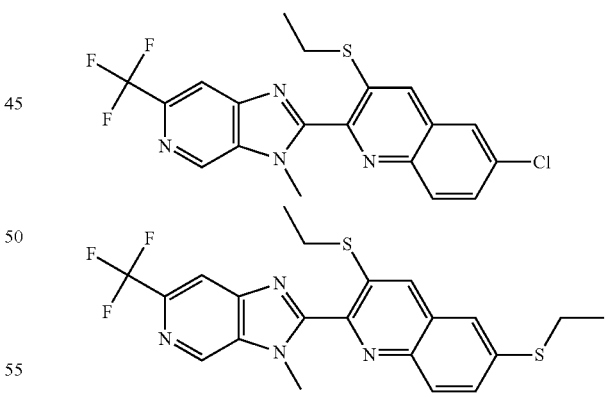

3,6-Dichloro-2-[3-methyl-6-(trifluoromethyl)imidazo[4,5-c]pyridin-2-yl]quinoline (0.20 g, 0.50 mmol) was dissolved in DMF (5 ml), and sodium ethylmercaptan (0.169 g, 2.01 mmol) was added. The reaction mixture was stirred at RT for 14 h, diluted with cyclohexane/ethyl acetate and filtered. The filtrate was concentrated. The column chromatography purification of the raw material via preparative HPLC with an MeCN/water gradient as eluent gave the two title compounds as a mixture, which was converted further without further purification.

(log P (neutral): 3.99; MH+: 423.
(log P (neutral): 4.35; MH+: 423.

3,6-Dichloro-2-[3-methyl-6-(trifluoromethyl)imidazo[4,5-c]pyridin-2-yl]quinoline (V-4)

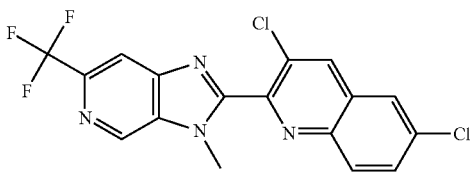 [SMILES: Cn1c(-c2nc3ccc(Cl)cc3cc2Cl)nc2cc(C(F)(F)F)ncc21]

3,6-Dichloroquinoline-2-carboxylic acid (1.00 g, 4.13 mmol), N3-methyl-6-(trifluoromethyl)pyridine-3,4-diamine (0.61 g, 3.17 mmol) and EDCI*HCl (0.61 g, 3.17 mmol) were dissolved in pyridine (20 ml), p-toluenesulphonic acid (0.60 g, 3.17 mmol) was added and then the mixture was stirred at 120° C. for 9 h. After cooling to RT, acetonitrile was added and the suspension obtained was filtered. The filtrate was concentrated and the residue was freed of salts by column chromatography purification with a CH₂Cl₂/MeOH gradient as eluent. The crude product obtained was converted further without further purification.

(log P (neutral): 3.53; MH+: 397; ¹H-NMR (400 MHz, DMSO-d₆): δ 9.31 (s, 1H), 8.91 (s, 1H), 8.34 (s, 1H), 8.29 (d, 1H), 8.20 (d, 1H), 7.95 (dd, 1H), 4.03 (s, 3H).

3,6-Dichloroquinoline-2-carboxylic acid (III-2)

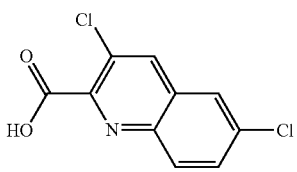 [SMILES: O=C(O)c1nc2ccc(Cl)cc2cc1Cl]

A solution of NaClO₂ (6.02 g, 66.7 mmol) and NaH₂PO₄ (8.00 g, 66.7 mmol) in water (25 ml) was added at 0° C. to a solution of 3,6-dichloroquinoline-2-carbaldehyde (3.00 g, 13.33 mmol) in t-BuOH (30 ml). The mixture was warmed up gradually to RT and stirred at this temperature for 3 h. After adding water, the product was extracted with dichloromethane. The combined organic phases were washed with saturated aqueous NaHSO₃ solution and saturated aqueous NaCl solution, dried over Na₂SO₄ and concentrated. The crude product was converted further without further purification.

MH+: 240; ¹H-NMR (400 MHz, DMSO-d₆): δ 7.86-7.89 (dd, J=2.4 & 9.04 Hz, 1H), 8.09-8.11 (d, J=9.08 Hz, 1H), 8.17 (d, J=2.36 Hz, 1H), 8.71 (s, 1H), 14.26 (brs, 1H).

3,6-Dichloroquinoline-2-carbaldehyde

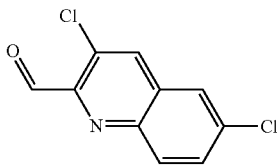 [SMILES: O=Cc1nc2ccc(Cl)cc2cc1Cl]

To a solution of 3,6-dichloro-2-methylquinoline (3.00 g, 14.2 mmol) in 1,4-dioxane (30 ml) was added SeO₂ (4.73 g, 42.7 mmol). The mixture obtained was refluxed for 3 h and then concentrated to dryness.

The crude product was taken up with water. The white solid that precipitated out was filtered off, washed with hexane and dried under reduced pressure.

MH+: 226; ¹H-NMR (400 MHz, CDCl₃): δ 7.72-7.75 (dd, J=2.28 & 9.0 Hz, 1H), 7.80-7.81 (d, J=2.2 Hz, 1H), 8.17-8.19 (d, J=9.24 Hz, 1H), 8.2 (s, 1H), 10.37 (s, 1H).

3,6-Dichloro-2-methylquinoline

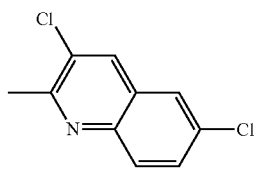

To a solution of 5-chloro-2-methyl-1H-indole (5.00 g, 30.3 mmol) and TEBAC (0.60 g, 0.300 mmol) in CHCl₃ (150 ml) was added, at 0° C., NaOH in water. The mixture was stirred at 0° C. for 3 h and then at RT for 14 h. The reaction mixture was then added gradually to ice-water and extracted with chloroform. The organic phase was washed with water, dried over Na₂SO₄ and concentrated on a rotary evaporator. The residue was purified by column chromatography purification with a hexane/ethyl acetate gradient as eluent.

MH+: 212; ¹H-NMR (400 MHz, CDCl₃): δ 2.78 (s, 3H), 7.58-7.61 (dd, J=2.32 & 9.0 Hz, 1H), 7.68-7.69 (d, J=2.28 Hz, 1H), 7.91-7.94 (d, J=9.0 Hz, 1H), 8.01 (s, 1H).

3,7-Dichloroquinoline-2-carboxylic acid (III-3)

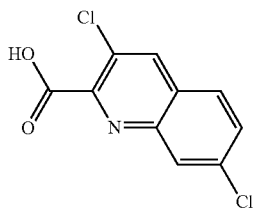 [SMILES: O=C(O)c1nc2cc(Cl)ccc2cc1Cl]

A solution of NaClO₂ (6.02 g, 66.7 mmol) and NaH₂PO₄ (8.00 g, 66.7 mmol) in water (25 ml) was added at 0° C. to a solution of 3,7-dichloroquinoline-2-carbaldehyde (3.00 g, 13.33 mmol) in t-BuOH (30 ml). The mixture was warmed up gradually to RT and stirred at this temperature for 3 h. After adding water, the product was extracted with dichloromethane. The combined organic phases were washed with saturated aqueous NaHCO₃ solution and saturated aqueous NaCl solution, dried over Na₂SO₄ and concentrated. The crude product was converted further without further purification.

MH+: 241; ¹H-NMR (400 MHz, D₆-DMSO) δ ppm: 14.29 (br, 1H), 8.81 (s, 1H), 8.18 (d, 1H), 8.08 (d, 1H), 7.79 (dd, 1H).

3,7-Dichloroquinoline-2-carbaldehyde

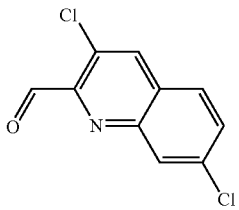 [SMILES: O=Cc1nc2cc(Cl)ccc2cc1Cl]

To a solution of 3,7-dichloro-2-methylquinoline (3.00 g, 14.2 mmol) in 1,4-dioxane (30 ml) was added SeO$_2$ (4.73 g, 42.7 mmol). The mixture obtained was refluxed for 3 h and then concentrated to dryness. The crude product was taken up with water. The white solid that precipitated out was filtered off, washed with hexane and dried under reduced pressure.

MH$^+$: 226; $^1$H-NMR (400 MHz, CDCl$_3$): δ 7.64-7.67 (dd, J=1.96 & 8.76 Hz, 1H), 7.76-7.78 (d, J=8.84 Hz, 1H), 8.24-8.25 (d, J=1.92 Hz, 1H), 8.26 (s, 1H), 10.36 (s, 1H).

3,7-Dichloro-2-methylquinoline

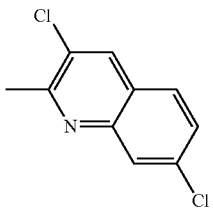

To a solution of 6-chloro-2-methyl-1H-indole (5.00 g, 30.3 mmol) and TEBAC (0.60 g, 0.300 mmol) in CHCl$_3$ (150 ml) was added, at 0° C., NaOH in water. The mixture was stirred at 0° C. for 3 h and then at RT for 14 h. The reaction mixture was then added gradually to ice-water and extracted with chloroform. The organic phase was washed with water, dried over Na$_2$SO$_4$ and concentrated on a rotary evaporator. The residue was purified by column chromatography purification with a hexane/ethyl acetate gradient as eluent.

MH$^+$: 214; $^1$H-NMR (400 MHz, CDCl$_3$): δ 2.79 (s, 3H), 7.44-7.47 (dd, J=2.08 & 8.72 Hz, 1H), 7.63-7.65 (d, J=8.72 Hz, 1H), 7.99-8.00 (d, J=1.92 Hz, 1H), 8.07 (s, 1H).

6-Chloro-2-methyl-1H-indole

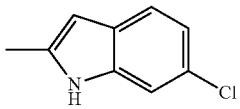

To a solution of 1-(4-chloro-2-nitrophenyl)propan-2-one (10.0 g, 46.9 mmol) in EtOH/H$_2$O (1:1, 50 ml) were added, at 0° C., glacial acetic acid (50 ml) and iron powder (12.4 g, 234.7 mmol). The reaction mixture obtained was then stirred at 100° C. for 4 h. The mixture was concentrated, and the residue was diluted with water and extracted with ethyl acetate. The organic phase was washed with water, dried over Na$_2$SO$_4$ and then concentrated. The residue was purified by column chromatography purification with a hexane/ethyl acetate gradient as eluent.

MH$^+$: 166; $^1$H-NMR (400 MHz, CDCl$_3$): δ 2.42 (s, 3H), 7.00-7.02 (dd, J=1.84 & 8.36 Hz, 1H), 7.25 (s, 1H), 7.37-7.39 (d, J=8.36 Hz, 1H), 7.84 (bs, 1H).

1-(4-Chloro-2-nitrophenyl)propan-2-one

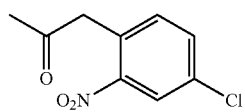

Ethyl 2-(2-nitro-4-chlorophenyl)-3-oxobutyrate (28.0 g, 98.2 mmol) was added at 0° C. to a solution of glacial acetic acid (60 ml) and sulphuric acid (40 ml). The reaction mixture was then stirred at 100° C. for 8 h. After cooling to RT, the mixture was added gradually to ice-water and extracted with ethyl acetate. The combined organic phases were washed with water, dried over Na$_2$SO$_4$ and freed of the solvent. The crude product was purified by column chromatography purification with a hexane/ethyl acetate gradient as eluent.

MH$^+$: 212; $^1$H-NMR (400 MHz, CDCl$_3$): δ 2.32 (s, 3H), 4.09 (s, 2H), 7.19-7.21 (d, J=9.0 Hz, 1H), 7.54-7.57 (dd, J=2.2 & 8.2 Hz, 1H), 8.11 (d, J=2.16 Hz, 1H).

Ethyl 2-(2-nitro-4-chlorophenyl)-3-oxobutyrate

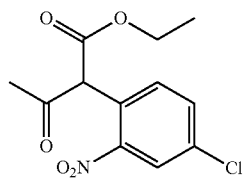

Ethyl acetoacetate (8.16 g, 62.8 mmol) was added at 0° C. to a suspension of Cs$_2$CO$_3$ (51.2 g, 157.1 mmol) in DMF (150 ml). After warming to RT, 1,4-dichloro-2-methylbenzene (10.0 g, 52.4 mmol) was slowly added dropwise. The reaction mixture obtained was then heated to 80° C. for 4 h. For quenching, the mixture was added to ice-water and extracted with ethyl acetate. The combined organic phases were washed with water, dried over Na$_2$SO$_4$ and concentrated. The residue was converted further without further purification.

MH$^+$: 286.

In analogy to the examples and according to the above-described preparation processes, the following compounds of the formula (I) can be obtained:

| Example | Structure |
|---|---|
| I-1 | 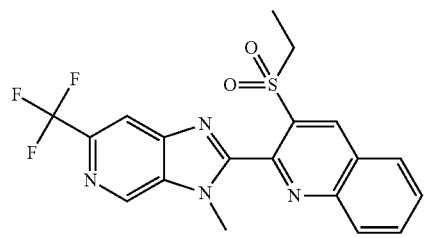 [SMILES: CCS(=O)(=O)c1cc2ccccc2nc1-c1nc2cc(C(F)(F)F)ncc2n1C] |
| I-2 | 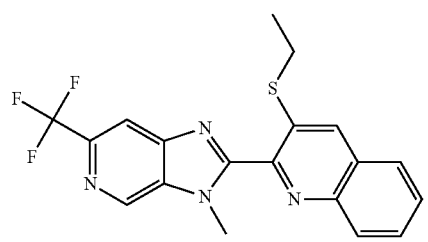 [SMILES: CCSc1cc2ccccc2nc1-c1nc2cc(C(F)(F)F)ncc2n1C] |
| I-3 | 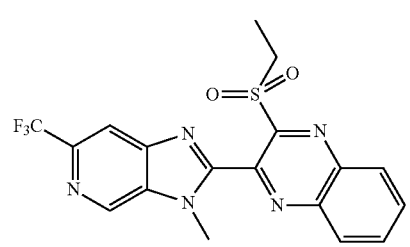 [SMILES: CCS(=O)(=O)c1nc2ccccc2nc1-c1nc2cc(C(F)(F)F)ncc2n1C] |
| I-4 | 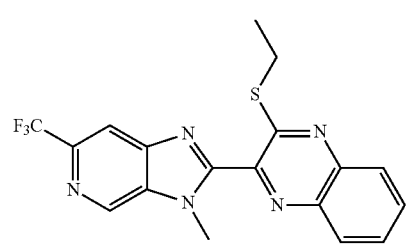 [SMILES: CCSc1nc2ccccc2nc1-c1nc2cc(C(F)(F)F)ncc2n1C] |
| I-5 | 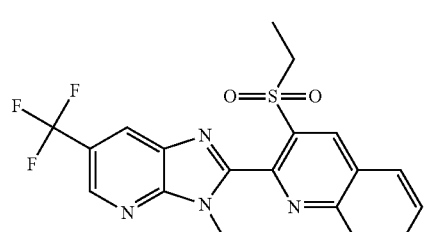 |
| I-6 | 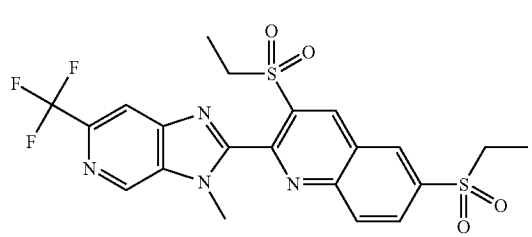 [SMILES: CCS(=O)(=O)c1ccc2nc(-c3nc4cc(C(F)(F)F)ncc4n3C)c(S(=O)(=O)CC)cc2c1] |
-continued
| Example | Structure |
|---|---|
| I-7 | 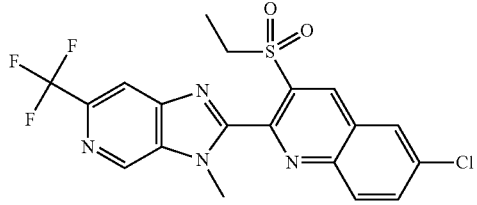 [SMILES: CCS(=O)(=O)c1cc2cc(Cl)ccc2nc1-c1nc2cc(C(F)(F)F)ncc2n1C] |
| I-8 | 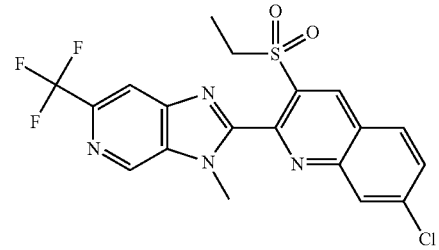 [SMILES: CCS(=O)(=O)c1cc2ccc(Cl)cc2nc1-c1nc2cc(C(F)(F)F)ncc2n1C] |
| I-9 | 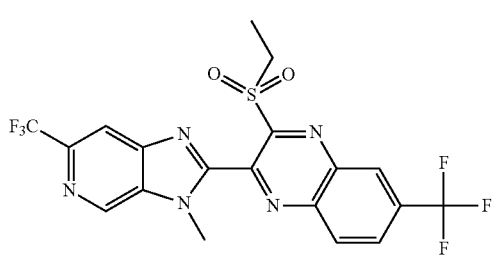 [SMILES: CCS(=O)(=O)c1nc2cc(C(F)(F)F)ccc2nc1-c1nc2cc(C(F)(F)F)ncc2n1C] |
| I-10 | 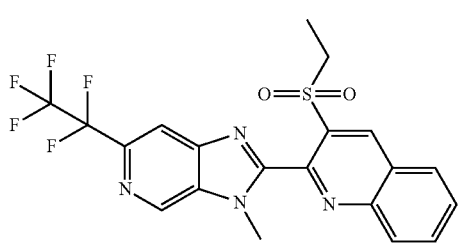 [SMILES: CCS(=O)(=O)c1cc2ccccc2nc1-c1nc2cc(C(F)(F)C(F)(F)F)ncc2n1C] |
| I-11 | 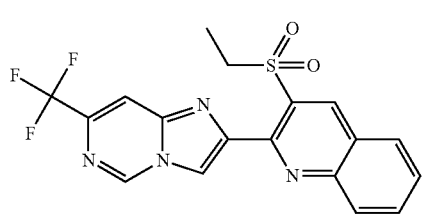 [SMILES: CCS(=O)(=O)c1cc2ccccc2nc1-c1cn2cnc(C(F)(F)F)cc2n1] |
| I-12 | 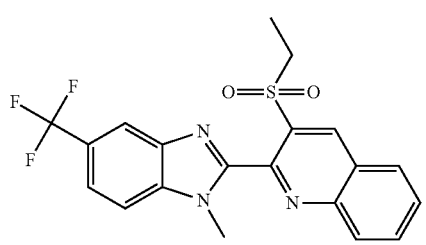 [SMILES: CCS(=O)(=O)c1cc2ccccc2nc1-c1nc2cc(C(F)(F)F)ccc2n1C] |

| Example | Structure |
|---|---|
| I-13 | 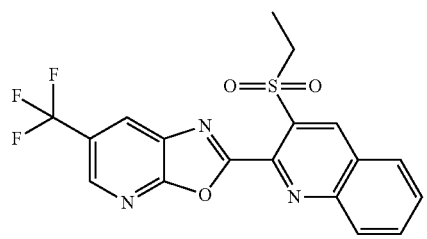 [SMILES: CCS(=O)(=O)c1cc2ccccc2nc1-c1nc2cc(C(F)(F)F)cnc2o1] |
| I-14 | 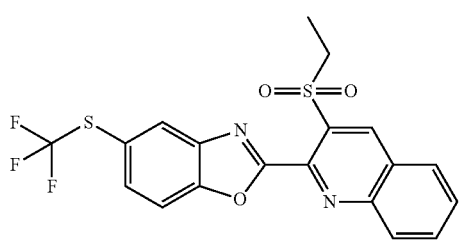 [SMILES: CCS(=O)(=O)c1cc2ccccc2nc1-c1nc2cc(SC(F)(F)F)ccc2o1] |
| I-15 | 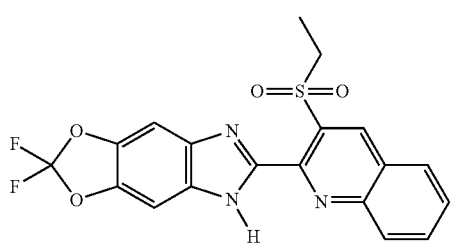 [SMILES: CCS(=O)(=O)c1cc2ccccc2nc1-c1nc2cc3c(cc2[nH]1)OC(F)(F)O3] |
| I-16 | 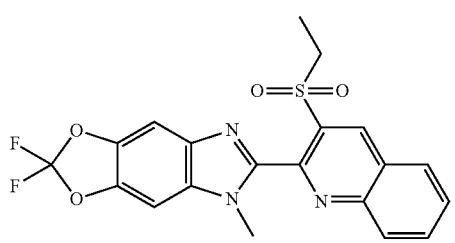 [SMILES: CCS(=O)(=O)c1cc2ccccc2nc1-c1nc2cc3c(cc2n1C)OC(F)(F)O3] |
| I-17 | 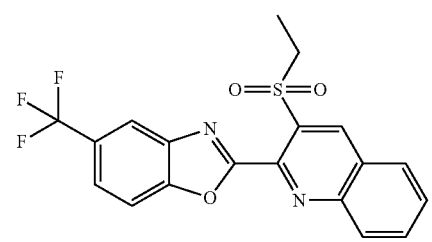 [SMILES: CCS(=O)(=O)c1cc2ccccc2nc1-c1nc2cc(C(F)(F)F)ccc2o1] |
| I-18 | 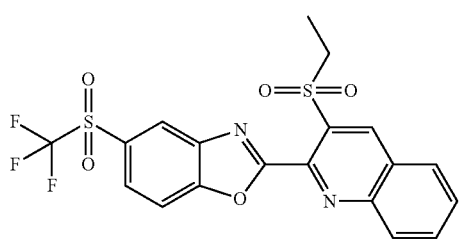 [SMILES: CCS(=O)(=O)c1cc2ccccc2nc1-c1nc2cc(S(=O)(=O)C(F)(F)F)ccc2o1] |
| I-19 | 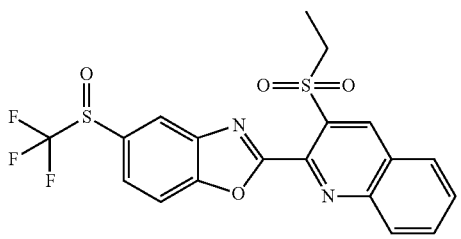 [SMILES: CCS(=O)(=O)c1cc2ccccc2nc1-c1nc2cc(S(=O)C(F)(F)F)ccc2o1] |
| I-20 | 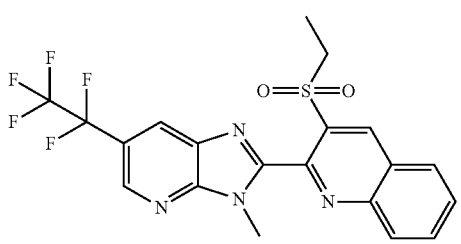 [SMILES: CCS(=O)(=O)c1cc2ccccc2nc1-c1nc2cc(C(F)(F)C(F)(F)F)cnc2n1C] |
| I-21 | 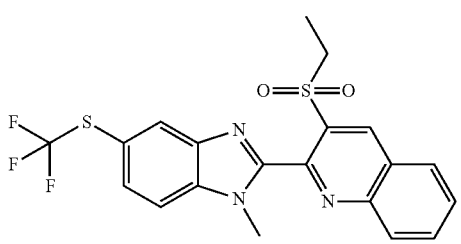 [SMILES: CCS(=O)(=O)c1cc2ccccc2nc1-c1nc2cc(SC(F)(F)F)ccc2n1C] |
| I-22 | 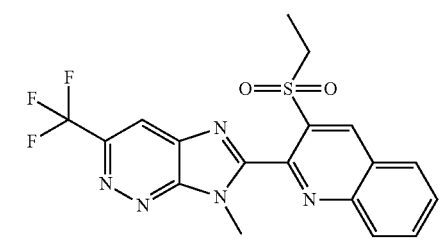 [SMILES: CCS(=O)(=O)c1cc2ccccc2nc1-c1nc2cc(C(F)(F)F)nnc2n1C] |
| I-23 | 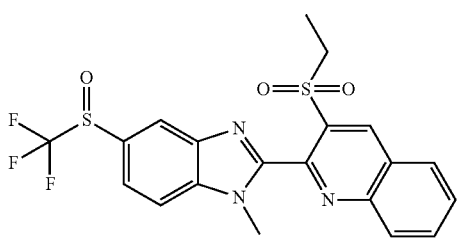 [SMILES: CCS(=O)(=O)c1cc2ccccc2nc1-c1nc2cc(S(=O)C(F)(F)F)ccc2n1C] |
| I-24 | 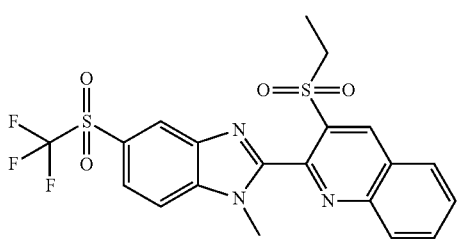 [SMILES: CCS(=O)(=O)c1cc2ccccc2nc1-c1nc2cc(S(=O)(=O)C(F)(F)F)ccc2n1C] |

| Example | Structure |
|---|---|
| I-25 | 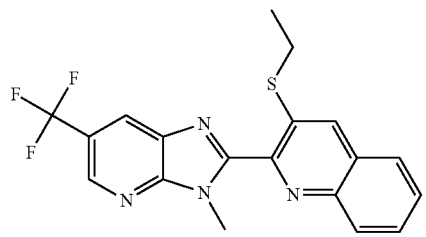 [SMILES: CCSc1cc2ccccc2nc1-c1nc2cc(C(F)(F)F)cnc2n1C] |
| I-26 | 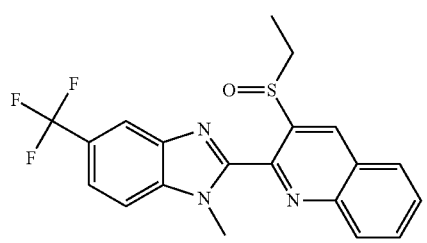 [SMILES: CCS(=O)c1cc2ccccc2nc1-c1nc2cc(C(F)(F)F)ccc2n1C] |
| I-27 | 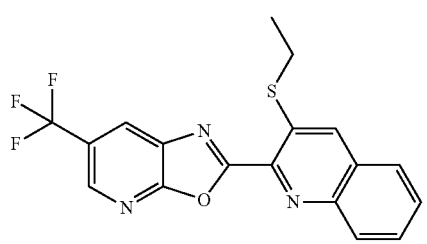 |
| I-28 | 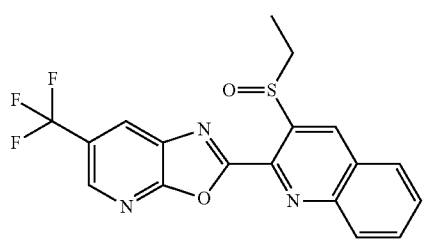 [SMILES: CCS(=O)c1cc2ccccc2nc1-c1nc2cc(C(F)(F)F)cnc2o1] |
| I-29 | 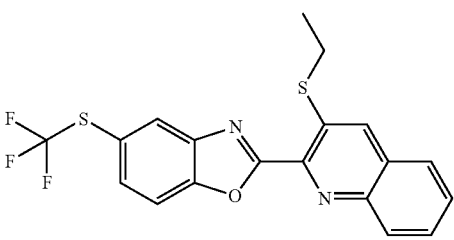 [SMILES: CCSc1cc2ccccc2nc1-c1nc2cc(SC(F)(F)F)ccc2o1] |
| I-30 | 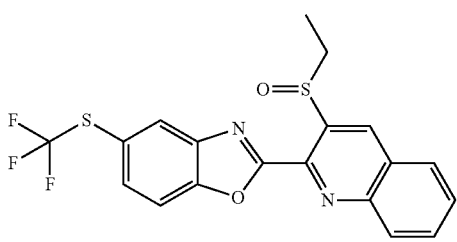 [SMILES: CCS(=O)c1cc2ccccc2nc1-c1nc2cc(SC(F)(F)F)ccc2o1] |
| Example | Structure |
|---|---|
| I-31 | 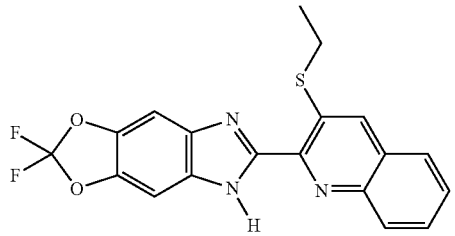 [SMILES: CCSc1cc2ccccc2nc1-c1nc2cc3c(cc2[nH]1)OC(F)(F)O3] |
| I-32 | 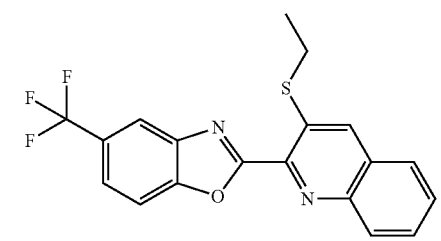 |
| I-33 | 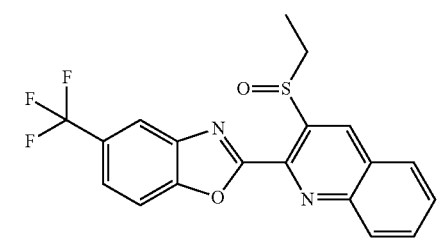 [SMILES: CCS(=O)c1cc2ccccc2nc1-c1nc2cc(C(F)(F)F)ccc2o1] |
| I-34 | 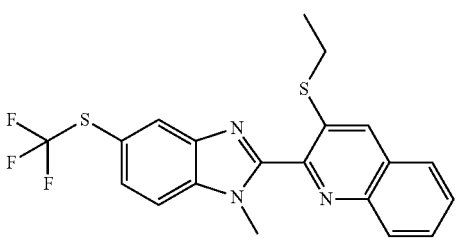 [SMILES: CCSc1cc2ccccc2nc1-c1nc2cc(SC(F)(F)F)ccc2n1C] |
| I-35 | 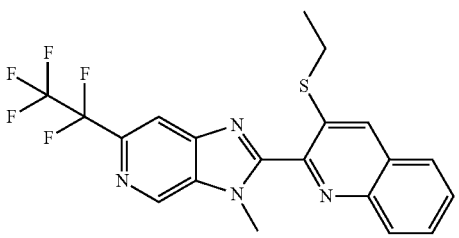 [SMILES: CCSc1cc2ccccc2nc1-c1nc2cc(C(F)(F)C(F)(F)F)ncc2n1C] |
| I-36 | 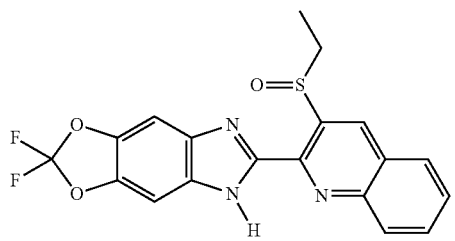 [SMILES: CCS(=O)c1cc2ccccc2nc1-c1nc2cc3c(cc2[nH]1)OC(F)(F)O3] |

| Example | Structure |
|---|---|
| I-37 | 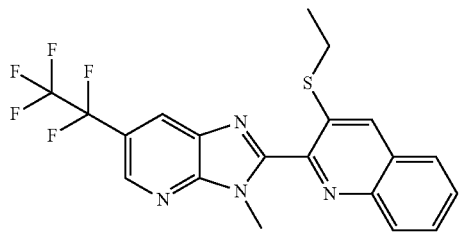 [SMILES: CCSc1cc2ccccc2nc1-c1nc2cc(C(F)(F)C(F)(F)F)cnc2n1C] |
| I-38 | 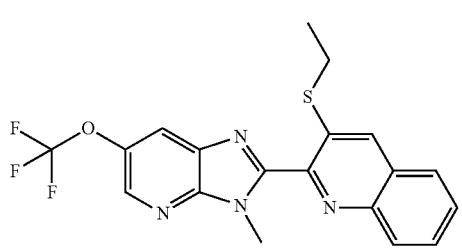 [SMILES: CCSc1cc2ccccc2nc1-c1nc2cc(OC(F)(F)F)cnc2n1C] |
| I-39 | 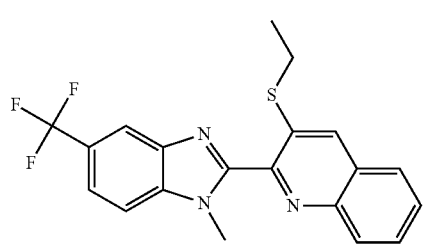 [SMILES: CCSc1cc2ccccc2nc1-c1nc2cc(C(F)(F)F)ccc2n1C] |
| I-40 | 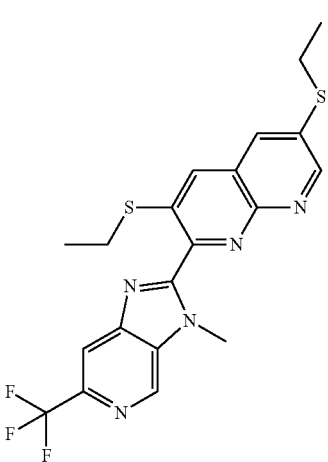 [SMILES: CCSc1cnc2nc(-c3nc4cc(C(F)(F)F)ncc4n3C)c(SCC)cc2c1] |
| Example | Structure |
|---|---|
| I-41 | 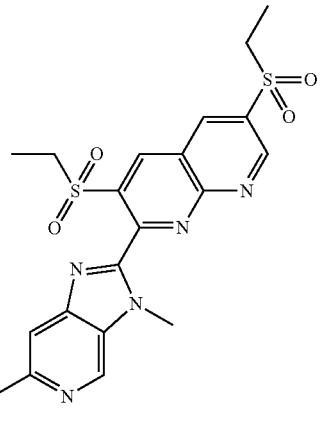 |
| I'-42 | 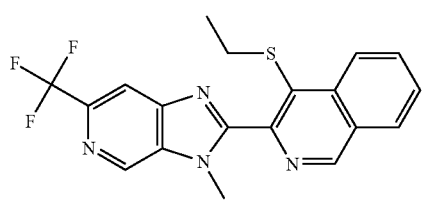 [SMILES: CCSc1c(-c2nc3cc(C(F)(F)F)ncc3n2C)ncc2ccccc12] |
| I'-43 | 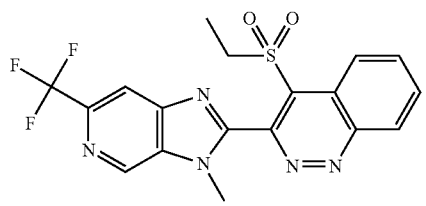 [SMILES: CCS(=O)(=O)c1c(-c2nc3cc(C(F)(F)F)ncc3n2C)nnc2ccccc12] |
| I'-44 | 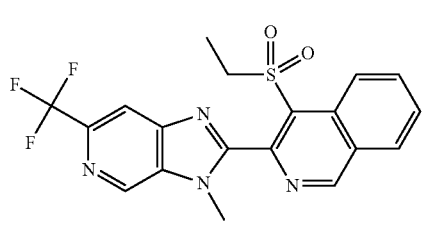 [SMILES: CCS(=O)(=O)c1c(-c2nc3cc(C(F)(F)F)ncc3n2C)ncc2ccccc12] |
| I'-45 | 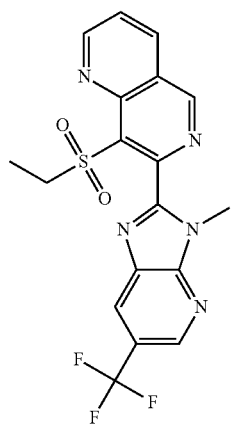 [SMILES: CCS(=O)(=O)c1c(-c2nc3cc(C(F)(F)F)cnc3n2C)ncc2cccnc12] |

| Example | Structure |
|---|---|
| I-46 | 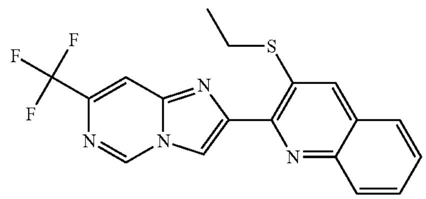 [SMILES: CCSc1cc2ccccc2nc1-c1cn2cnc(C(F)(F)F)cc2n1] |
| I'-47 | 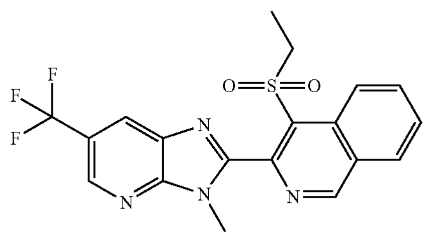 [SMILES: CCS(=O)(=O)c1c(-c2nc3cc(C(F)(F)F)cnc3n2C)ncc2ccccc12] |
| I'-48 | 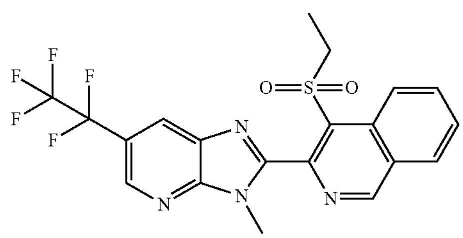 [SMILES: CCS(=O)(=O)c1c(-c2nc3cc(C(F)(F)C(F)(F)F)cnc3n2C)ncc2ccccc12] |
| I'-49 | 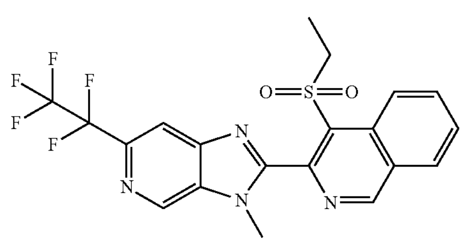 [SMILES: CCS(=O)(=O)c1c(-c2nc3cc(C(F)(F)C(F)(F)F)ncc3n2C)ncc2ccccc12] |
| I'-50 | 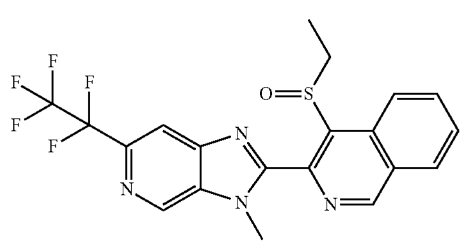 [SMILES: CCS(=O)c1c(-c2nc3cc(C(F)(F)C(F)(F)F)ncc3n2C)ncc2ccccc12] |
| I'-51 | 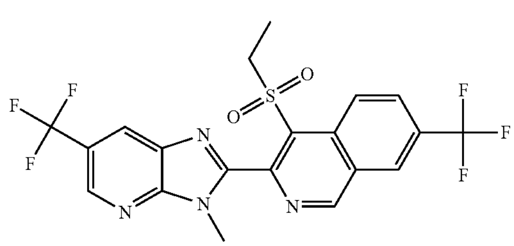 [SMILES: CCS(=O)(=O)c1c(-c2nc3cc(C(F)(F)F)cnc3n2C)ncc2cc(C(F)(F)F)ccc12] |
| I'-52 | |
| I'-53 | |
| I'-54 | |
| I-55 | |
| I-56 | |
| I-57 | |

| Example | Structure |
|---|---|
| I'-58 | 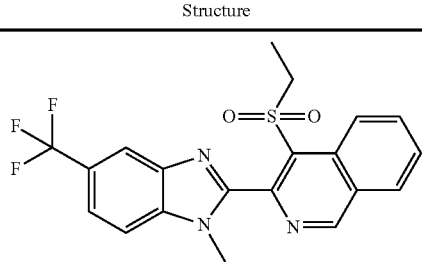 |
| I-59 | 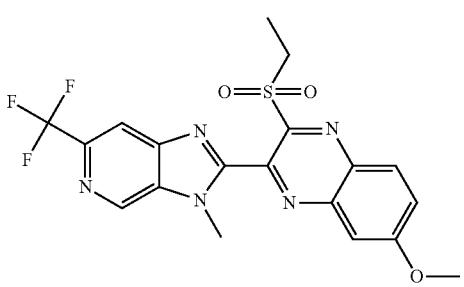 [SMILES: CCS(=O)(=O)c1nc2ccc(OC)cc2nc1-c1nc2cc(C(F)(F)F)ncc2n1C] |

Preparation of
N2-methyl-5-(trifluoromethoxy)pyridine-2,3-diamine
(II-1)

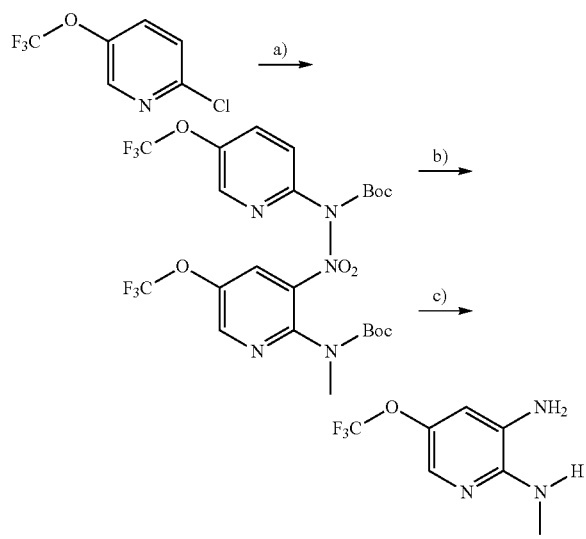

Step a)

24 g (120 mmol) of 2-chloro-5-(trifluoromethoxy)pyridine, 19.1 g (150 mmol) of tert-butyl N-methylcarbamate and 17.5 g (180 mmol) of sodium tert-butoxide were dissolved in 400 ml of toluene, 2.8 g (3 mmol) of tris(dibenzylideneacetone)dipalladium(0) and 1.73 g (3 mmol) of Xantphos were added under argon, and the mixture was stirred at 100-105° C. for 12 h. Subsequently, the mixture was filtered through Celite and the solvent was distilled off under reduced pressure.

Step b)

To 100 ml of a sulphuric acid solution cooled to 0° C. were added 30 g (103 mmol) of tert-butyl N-methyl-N-[5-(trifluoromethoxy)-2-pyridyl]carbamate and then 10.4 ml (166 mmol) of concentrated nitric acid. The mixture was stirred at 5-10° C. for 2 h and admixed with ice-water. The solution was neutralized with sodium hydroxide and extracted with ethyl acetate. The organic phase was dried over magnesium sulphate and the solvent was distilled off under reduced pressure. The residue was purified by column chromatography purification with a chloroform/hexane mixture (1:2) as eluent.

Step c)

A mixture of 10.0 g (42.2 mmol) of tert-butyl N-methyl-N-[3-nitro-5-(trifluoromethoxy)-2-pyridyl]carbamate and 0.7 g of palladium/charcoal (10%) was stirred in 250 ml of methanol under a hydrogen atmosphere at room temperature for 2 h. Subsequently, the mixture was filtered through Celite and the solvent was distilled off under reduced pressure. The further purification of the product was effected by vacuum distillation at 88-90° C. and 0.1 mbar.

$^1$H NMR (400 MHz, CDCl$_3$, ppm): δ 7.70 (d, J=0.8 Hz, 1H), 6.75 (d, J=0.8 Hz, 1H), 4.20 (br. s., 1H), 3.32 (br. s., 2H), 3.00 (s, 3H). This measurement of the NMR spectrum was effected on a Bruker Avance 3300 equipped with a 5 mm broadband liquid probe.

The log P values are measured according to EEC Directive 79/831 Annex V.A8 by HPLC (high-performance liquid chromatography) on a reversed-phase column (C 18). Temperature: 55° C.

The LC-MS determination in the acidic range is effected at pH 2.7 using 0.1% aqueous formic acid and acetonitrile (contains 0.1% formic acid) as eluents; linear gradient from 10% acetonitrile to 95% acetonitrile. Called log P (HCOOH) in the table.

LC-MS determination in the neutral range is effected at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is carried out using unbranched alkan-2-ones (having 3 to 16 carbon atoms) with known log P values (log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum was recorded is stated.

NMR Peak List Method

The NMR data of selected examples are stated in the form of NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form:

δ$_1$ (intensity$_1$); δ$_2$ (intensity$_2$); . . . ; δ$_i$ (intensity$_i$); . . . ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the NMR peaks are similar to the conventional $^1$H-NMR printouts and thus usually contain all peaks listed in a conventional NMR interpretation.

In addition, like conventional NMR printouts, they may show solvent signals, signals of stereoisomers of the target compounds which are likewise provided by the invention, and/or peaks of impurities.

In the reporting of compound signals within the delta range of solvents and/or water, our lists of NMR peaks show the standard solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional NMR interpretation.

Further details of NMR peak lists can be found in the Research Disclosure Database Number 564025.

Example I-1:

$^1$H-NMR(400.0 MHz, $d_6$-DMSO): δ =
9.338(4.4); 9.320(3.8); 8.518(1.5); 8.498(1.6); 8.328(4.0); 8.300(1.5); 8.278(2.0); 8.172(0.9); 8.168(0.9); 8.154(1.2); 8.151(1.6); 8.133(0.8); 8.130(0.8); 7.993(1.0); 7.991(1.0); 7.973(1.7); 7.955(0.8); 7.953(0.8); 3.927(16.0); 3.864(1.0); 3.846(3.4); 3.827(3.4); 3.809(1.0); 3.321(49.5); 2.672(0.4); 2.525 (0.9); 2.512(22.4); 2.507(46.3); 2.503(61.4); 2.498(44.5); 2.494(21.5); 2.330(0.4); 2.074(1.7); 1.252(3.6); 1.234(8.1); 1.215(3.5); 0.000(1.7)

Example I-2:

$^1$H-NMR(400.0 MHz, $d_6$-DMSO): δ =
9.289(4.1); 8.816(0.4); 8.584(4.4); 8.317(4.4); 8.290(0.7); 8.135(0.5); 8.107(3.4); 8.085(3.9); 7.953(0.4); 7.838(0.8); 7.823(1.4); 7.820(1.7); 7.799(1.3); 7.776(1.3); 7.774(1.3); 7.756(1.6); 7.736(0.7); 7.572(0.3); 6.839(0.4); 4.029(16.0); 3.385(0.8); 3.333(91.2); 3.324(82.2); 3.151(1.2); 3.133(3.8); 3.115(3.9); 3.096(1.3); 2.891(2.9); 2.879(0.8); 2.811(0.6); 2.799(0.6); 2.732(2.0); 2.671(0.7); 2.667(0.6); 2.507(91.1); 2.502(120.9); 2.498(95.2); 2.329(0.7); 1.316(0.5); 1.310(0.3); 1.298(0.9); 1.285(4.1); 1.267(8.5); 1.249(4.0); 1.169(0.3); 0.000(1.3)

Example I-3:

$^1$H-NMR(400.0 MHz, $d_6$-DMSO): δ =
9.382(0.4); 9.321(4.0); 8.471(1.3); 8.466(0.9); 8.458(1.4); 8.454(1.0); 8.447(1.5); 8.439(0.3); 8.401(1.2); 8.395(1.0); 8.390(1.8); 8.382(1.3); 8.377(1.8); 8.370(0.6); 8.333(4.2); 8.265(0.6); 8.252(2.6); 8.248(1.9); 8.240(2.2); 8.233(1.6); 8.228(2.3); 8.216(0.4); 5.754(0.7); 4.390(1.7); 3.993(16.0); 3.847(1.2); 3.829(4.0); 3.810(4.0); 3.792(1.2); 3.317(37.4); 2.676(0.4); 2.671(0.5); 2.667(0.4); 2.506(58.3); 2.502(77.1); 2.497(58.9); 2.333(0.4); 2.329(0.5); 2.324(0.4); 1.425(0.4); 1.406(0.9); 1.388(0.4); 1.289(4.1); 1.270(8.8); 1.252(4.0); 0.000(2.9)

Example I-4:

$^1$H-NMR(400.0 MHz, $d_6$-DMSO): δ =
9.331(3.4); 8.368(3.5); 8.366(3.6); 8.184(1.3); 8.181(1.4); 8.163(1.6); 8.161(1.6); 8.086(1.2); 8.084(1.3); 8.065(1.7); 8.063(1.7); 7.980(0.9); 7.976(1.0); 7.963(1.2); 7.959(1.6); 7.956(0.8); 7.942(0.9); 7.938(0.9); 7.872(1.1); 7.868(1.1); 7.854(0.9); 7.851(1.6); 7.848(1.1); 7.834(0.7); 7.830(0.7); 4.178(16.0); 3.327(2.2); 3.317(49.6); 3.309(4.9); 3.290(4.0); 3.272(1.3); 2.671(0.4); 2.511(24.5); 2.507(48.6); 2.502(65.4); 2.498(49.8); 2.493(25.2); 2.472(0.5); 2.329(0.4); 1.398(0.4); 1.384(4.1); 1.366(8.9); 1.347(4.0); 0.146(0.3); 0.008(3.7); 0.000(82.5); −0.008(3.5); −0.150(0.4)

Example I-5:

$^1$H-NMR(400.0 MHz, $d_6$-DMSO): δ =
9.342(4.1); 8.924(2.2); 8.921(2.2); 8.712(2.2); 8.708(2.2); 8.518(1.4); 8.498(1.5); 8.304(1.3); 8.283(1.8); 8.172(0.9); 8.168(0.9); 8.154(1.1); 8.151(1.5); 8.147(0.8); 8.133(0.9); 8.129(0.8); 7.992(1.0); 7.989(1.0); 7.971(1.6); 7.969(1.1); 7.954(0.8); 7.951(0.8); 5.756(0.9); 3.903(0.9); 3.884(3.2); 3.866(3.2); 3.847(1.0); 3.833(16.0); 3.323(80.9); 2.676(0.3); 2.672(0.4); 2.667(0.3); 2.525(1.0); 2.511(25.5); 2.507(54.0); 2.502(75.3); 2.498(55.4); 2.493(25.9); 2.329(0.5); 1.265(3.3); 1.246(7.6); 1.228(3.3); 0.008(0.5); 0.000(17.4); −0.009(0.6)

Example I-6:

$^1$H-NMR(400.0 MHz, $CDCl_3$): δ =
9.245(4.5); 9.045(3.7); 8.795(2.5); 8.791(2.5); 8.464(1.0); 8.442(3.3); 8.426(2.5); 8.421(2.3); 8.403(0.8); 8.399(0.8); 8.148(3.9); 7.265(14.1); 5.301(0.7); 3.996(16.0); 3.939(1.0); 3.921(3.5); 3.902(3.6); 3.884(1.1); 3.319(1.1); 3.300(3.6); 3.281(3.7); 3.263(1.2); 1.624(11.0); 1.440(3.6); 1.421(7.7); 1.402(6.1); 1.382(8.0); 1.364(3.6); 1.255(0.9); 0.000(0.5)

Example I-7:

$^1$H-NMR(601.6 MHz, $CDCl_3$): δ =
9.014(3.6); 8.996(4.2); 8.211(2.0); 8.197(2.3); 8.128(6.8); 7.970(2.0); 7.966(1.5); 7.955(1.8); 7.952(1.3); 7.265(1.8); 7.261(4.8); 5.302(0.6); 5.298(1.5); 3.950(16.0); 3.872(1.2); 3.859(3.8); 3.847(3.8); 3.835(1.2); 1.565(3.0); 1.401(3.9); 1.388(8.0); 1.376(3.7); 1.257(0.4); 0.004(1.9); 0.000(5.0)

Example I-8:

$^1$H-NMR(601.6 MHz, $CDCl_3$): δ =
9.053(3.3); 8.793(2.3); 8.792(2.5); 8.790(2.4); 8.565(3.7); 8.227(3.4); 8.226(3.4); 8.153(1.0); 8.150(1.1); 8.138(2.0); 8.136(2.1); 8.108(2.8); 8.094(1.6); 7.265(6.5); 5.299(1.2); 4.114(16.0); 4.011(0.4); 3.938(0.4); 3.279(1.1); 3.267(3.6); 3.254(3.6); 3.242(1.2); 1.612(2.0); 1.370(3.7); 1.357(7.9); 1.345(3.7); 1.322(0.5); 1.256(0.4); 0.000(4.7)

Example I-9:

$^1$H-NMR(400.0 MHz, $d_6$-DMSO): δ =
9.340(4.1); 8.840(2.5); 8.685(1.7); 8.663(2.1); 8.490(1.7); 8.485(1.6); 8.468(1.3); 8.463(1.4); 8.357(4.4); 8.315(0.5); 4.096(0.4); 4.025(16.0); 3.896(1.1); 3.877(3.9); 3.859(3.9); 3.840(1.2); 3.320(70.9); 2.676(1.0); 2.671(1.4); 2.666(1.0); 2.524(3.5); 2.510(79.2); 2.506(167.8); 2.502(236.0); 2.497(178.5); 2.333(1.0); 2.328(1.4); 2.324(1.0); 1.305(4.1); 1.287(8.9); 1.268(4.0); 1.235(0.9); 0.146(0.7); 0.008(5.0); 0.000(162.7); −0.008(6.4); −0.150(0.7)

| Example I-10: |
|---|

$^1$H-NMR(400.0 MHz, d$_6$-DMSO): δ =
9.344(8.5); 8.520(1.5); 8.501(1.6); 8.360(4.4); 8.358(4.3); 8.297(1.5); 8.276(2.0); 8.173(0.9); 8.170(0.9); 8.156(1.2); 8.152(1.6); 8.135(0.9); 8.131(0.9); 7.996(1.1); 7.993(1.1); 7.975(1.7); 7.958(0.8); 7.955(0.8); 3.929(16.0); 3.873(1.0); 3.854(3.4); 3.836(3.5); 3.817(1.0); 3.319(42.6); 2.675(0.9); 2.671 (1.2); 2.666(0.9); 2.524(2.9); 2.519(4.5); 2.511(74.4); 2.506(154.2); 2.502(204.0); 2.497(145.1); 2.493(69.5); 2.333(0.9); 2.328(1.2); 2.324(0.9); 1.398(8.1); 1.251(3.6); 1.232(8.1); 1.214(3.5); 0.146(0.3); 0.008(2.3); 0.000(74.8); −0.008(2.7); −0.150(0.3)

| Example I-11: |
|---|

$^1$H-NMR(400.0 MHz, d$_6$-DMSO): δ =
9.701(6.1); 9.234(8.6); 8.736(9.1); 8.412(3.2); 8.395(8.0); 8.206(2.9); 8.184(4.0); 8.084(1.9); 8.081(1.9); 8.067(2.4); 8.064(3.2); 8.046(1.7); 8.043(1.6); 7.871(2.1); 7.869(2.1); 7.851(3.4); 7.833(1.7); 7.831(1.6); 5.758(0.9); 4.174(1.9); 4.156(6.5); 4.137(6.5); 4.119(2.0); 4.099(0.5); 4.085(0.4); 3.322(51.5); 3.176(2.4); 3.163(2.3); 2.676(0.6); 2.672(0.8); 2.667(0.6); 2.525(2.1); 2.507(108.3); 2.503(142.1); 2.498(103.3); 2.334(0.6); 2.329(0.8); 2.325(0.6); 1.305(7.2); 1.286(16.0); 1.268(7.1); 1.259(1.4); 1.241(1.0); 1.233(1.0); 0.880(0.6); 0.008(0.9); 0.000(29.2); −0.009(1.2)

| Example I-12: |
|---|

$^1$H-NMR(400.0 MHz, d$_6$-DMSO): δ =
9.308(4.8); 8.502(1.7); 8.482(1.8); 8.282(1.6); 8.261(2.2); 8.151(4.0); 8.134(1.7); 8.116(0.8); 8.113(0.9); 7.984(1.9); 7.970(1.4); 7.963(2.4); 7.952(1.8); 7.932(0.9); 7.753(1.7); 7.732(1.4); 3.926(1.0); 3.908(3.5); 3.889(3.5); 3.871(1.1); 3.817(16.0); 3.320(31.9); 2.670(1.3); 2.666(1.1); 2.523(2.9); 2.506 (167.3); 2.501(228.6); 2.497(175.1); 2.332(1.0); 2.328(1.3); 2.324(1.1); 1.397(2.8); 1.253(3.6); 1.235(8.0); 1.217(3.6); 0.146(0.4); 0.008(2.2); 0.000(74.0); −0.150(0.4)

| Example I-13: |
|---|

$^1$H-NMR(400.0 MHz, d$_6$-DMSO): δ =
9.396(8.7); 9.044(6.3); 9.032(5.5); 8.522(3.1); 8.502(3.3); 8.360(3.1); 8.339(4.0); 8.203(1.8); 8.200(1.8); 8.185(2.4); 8.182(3.2); 8.164(1.8); 8.161(1.7); 8.025(2.1); 8.023(2.1); 8.005(3.4); 7.987(1.7); 3.962(2.1); 3.943(7.0); 3.925(7.1); 3.906(2.2); 3.321(41.5); 3.151(0.8); 2.676(0.8); 2.672(1.1); 2.667(0.8); 2.525(2.7); 2.507(143.3); 2.503(183.1); 2.498(133.7); 2.334(0.8); 2.329(1.1); 2.325(0.8); 1.990(0.7); 1.397(7.6); 1.340(7.4); 1.322(16.0); 1.303(7.1); 1.175(0.4); 0.000(2.0)

| Example I-14: |
|---|

$^1$H-NMR(400.0 MHz, d$_6$-DMSO): δ =
9.366(8.9); 8.510(3.2); 8.490(3.4); 8.406(5.6); 8.403(5.7); 8.329(3.1); 8.308(4.1); 8.183(1.9); 8.180(1.9); 8.165(2.6); 8.162(3.6); 8.157(5.8); 8.144(2.1); 8.141(2.1); 8.135(6.2); 8.004(2.2); 7.984(3.5); 7.966(1.8); 7.950(3.3); 7.946(3.2); 7.929(2.7); 7.925(2.7); 4.013(2.0); 3.995(6.9); 3.976(7.0); 3.958(2.1); 3.322(22.1); 2.677(0.5); 2.673(0.6); 2.508(83.7); 2.504(107.7); 2.499(78.2); 2.330(0.6); 2.326(0.5); 1.990(0.5); 1.397(15.1); 1.336(7.3); 1.317(16.0); 1.299(7.1); 0.146(0.4); 0.008(3.0); 0.000(78.2); −0.008(3.8); −0.149(0.4)

| Example I-15: |
|---|

$^1$H-NMR(400.0 MHz, d$_6$-DMSO): δ =
13.544(4.7); 9.270(10.1); 8.445(4.0); 8.424(4.2); 8.256(3.8); 8.235(5.0); 8.121(2.3); 8.103(3.7); 8.082(2.0); 7.907(2.6); 7.888(4.0); 7.869(2.2); 7.800(1.0); 7.632(1.0); 4.342(2.2); 4.324(7.0); 4.305(7.1); 4.287(2.3); 3.319(42.7); 2.671(2.2); 2.502(366.5); 2.329(2.1); 1.397(2.2); 1.322(7.5); 1.304(16.0); 1.286(7.5); 1.233(0.5); 0.000(53.2)

| Example I-16: |
|---|

$^1$H-NMR(400.0 MHz, d$_6$-DMSO): δ =
9.280(4.8); 8.483(1.6); 8.462(1.8); 8.265(16); 8.244(2.2); 8.139(1.0); 8.137(1.0); 8.119(1.8); 8.101(1.0); 8.098(0.9); 7.952(1.2); 7.933(1.8); 7.913(1.2); 7.906(5.8); 7.804(6.0); 4.548(0.7); 3.935(1.0); 3.917(3.4); 3.898(3.5); 3.880(1.1); 3.763(16.0); 3.320(48.0); 2.675(0.7); 2.671(0.9); 2.506(120.5); 2.502(157.3); 2.497(116.2); 2.333(0.7); 2.328(0.9); 2.324(0.7); 2.117(2.2); 1.304(0.4); 1.244(4.1); 1.226(8.4); 1.207(3.7); 1.140(4.9); 0.008(0.8); 0.000(16.0)

| Example I-17: |
|---|

$^1$H-NMR(400.0 MHz, d$_6$-DMSO): δ =
9.370(8.8); 8.513(3.1); 8.493(3.3); 8.435(5.2); 8.339(3.1); 8.318(4.0); 8.216(3.6); 8.194(4.5); 8.186(2.1); 8.183(2.0); 8.169(2.4); 8.165(3.2); 8.148(1.8); 8.144(1.7); 8.007(2.1); 8.005(2.2); 7.987(6.2); 7.967(4.0); 4.013(2.0); 3.995(6.9); 3.976(7.0); 3.958(2.2); 3.323(27.9); 2.677(0.5); 2.672(0.6); 2.668(0.5); 2.508(85.4); 2.503(111.3); 2.499(81.1); 2.334(0.5); 2.330(0.6); 1.990(0.6); 1.397(4.8); 1.338(7.3); 1.320(16.0); 1.301(7.2); 1.175(0.3); 0.000(2.1)

| Example I-18: |
|---|

$^1$H-NMR(400.0 MHz, d$_6$-DMSO): δ =
9.396(8.7); 8.872(5.2); 8.868(5.4); 8.524(3.1); 8.504(3.4); 8.460(4.0); 8.438(6.5); 8.371(3.4); 8.367(3.4); 8.345(5.2); 8.323(4.1); 8.198(1.8); 8.195(1.8); 8.177(3.2); 8.159(1.8); 8.156(1.7); 8.022(2.2); 8.002(3.4); 7.984(1.8); 4.038(0.7); 4.021(2.7); 4.003(7.1); 3.984(6.9); 3.965(2.1); 3.319(112.3); 2.675 (1.5); 2.671(2.1); 2.667(1.6); 2.507(270.1); 2.502(351.4); 2.498(258.1); 2.333(1.5); 2.329(2.0); 1.989(2.5); 1.344(7.3); 1.325(16.0); 1.307(7.2); 1.241(1.7); 1.193(0.7); 1.175(1.4); 1.157(0.7); 0.146(1.6); 0.008(18.0); 0.000(369.9); −0.008(19.6); −0.150(1.7)

| Example I-19: |
|---|

$^1$H-NMR(400.0 MHz, d$_6$-DMSO): δ =
9.377(9.2); 8.555(6.3); 8.517(3.5); 8.496(3.7); 8.344(5.2); 8.336(3.8); 8.323(6.5); 8.315(5.1); 8.189(2.0); 8.187(2.0); 8.169(3.5); 8.151(1.9); 8.148(1.9); 8.126(3.5); 8.105(2.9); 8.009(2.4); 7.991(3.7); 7.973(1.9); 4.038(0.8); 4.019(2.7); 4.001(7.2); 3.982(7.2); 3.964(2.3); 3.320(127.4); 2.671(1.9); 2.502 (328.7); 2.498(252.0); 2.329(2.0); 1.989(2.9); 1.341(7.4); 1.322(16.0); 1.304(7.3); 1.193(0.8); 1.175(1.6); 1.158(0.9); 0.146(1.5); 0.000(314.0); −0.150(1.5)

| Example I-20: |
|---|

$^1$H-NMR(400.0 MHz, d$_6$-DMSO): δ =
9.347(4.5); 8.856(2.4); 8.851(2.5); 8.671(2.5); 8.667(2.4); 8.520(1.5); 8.501(1.6); 8.299(1.5); 8.278(2.0); 8.172(0.9); 8.168(0.9); 8.154(1.2); 8.151(1.6); 8.133(0.9); 8.130(0.8); 7.990(1.1); 7.972(1.7); 7.955(0.9); 4.418(0.4); 3.912(0.9); 3.894(3.4); 3.876(3.5); 3.857(1.2); 3.844(16.0); 3.320(26.1); 2.676 (0.6); 2.671(0.7); 2.667(0.6); 2.525(1.9); 2.511(47.8); 2.507(97.0); 2.502(127.6); 2.498(91.3); 2.494(44.2); 2.333(0.5); 2.329(0.8); 1.264(3.5); 1.246(8.1); 1.235(2.1); 1.227(3.8); 0.146(0.6); 0.008(4.6); 0.000(125.9); −0.008(5.3); −0.150(0.6)

| Example I-21: |
|---|

$^1$H-NMR(400.0 MHz, d$_6$-DMSO): δ =
9.306(4.5); 8.500(1.6); 8.480(1.7); 8.270(1.5); 8.249(2.1); 8.153(3.5); 8.131(1.7); 8.113(0.9); 8.110(0.8); 7.969(1.1); 7.967(1.1); 7.949(1.7); 7.927(2.7);

-continued 7.906(2.8); 7.735(1.6); 7.732(1.6); 7.714(1.4); 7.710(1.4); 3.930(0.9); 3.911(3.2); 3.893(3.3); 3.875(1.0); 3.803(15.0); 3.325(91.4); 2.671(0.5); 2.667(0.4); 2.507(72.7); 2.502(93.6); 2.498(68.1); 2.329(0.5); 1.398(16.0); 1.253(3.4); 1.234(7.8); 1.216(3.4); 0.146(0.4); 0.008(3.7); 0.000(79.4); −0.008(3.7); −0.150(0.4)
Example I-22:

$^1$H-NMR(400.0 MHz, $d_6$-DMSO): δ =
9.389(4.7); 8.807(6.3); 8.542(2.0); 8.523(1.9); 8.329(1.7); 8.308(2.3); 8.197(1.2); 8.177(1.9); 8.159(1.0); 8.023(1.4); 8.003(2.0); 7.983(1.0); 5.756(0.5); 4.007(16.0); 3.833(1.2); 3.814(3.6); 3.796(3.6); 3.778(1.1); 3.539(0.4); 3.321(145.9); 3.256(0.6); 2.671(1.6); 2.506(238.8); 2.502(294.2); 2.497(210.6); 2.329(1.6); 1.264(4.1); 1.246(8.7); 1.227(4.4); 1.207(0.7); 1.189(1.0); 1.182(0.4); 1.173(0.9); 1.155(0.5); 0.854(0.3); 0.146(0.5); 0.000(101.4); −0.149(0.5)
Example I-23:

$^1$H-NMR(400.0 MHz, $d_6$-DMSO): δ =
9.320(5.2); 8.508(1.9); 8.488(2.1); 8.338(3.8); 8.276(1.8); 8.254(2.5); 8.157(1.1); 8.138(1.9); 8.117(3.4); 8.096(3.1); 7.976(1.3); 7.957(2.0); 7.938(1.1); 7.921(2.0); 7.900(1.7); 3.927(1.1); 3.908(3.5); 3.890(3.6); 3.871(1.3); 3.844(16.0); 3.321(40.5); 2.672(0.6); 2.502(109.7); 2.329(0.6); 1.397(4.1); 1.257(3.8); 1.238(8.3); 1.220(3.8); 0.000(48.0)
Example I-24:

$^1$H-NMR(400.0 MHz, $d_6$-DMSO): δ =
9.340(4.6); 8.561(3.1); 8.518(1.7); 8.497(1.8); 8.285(1.6); 8.263(2.2); 8.225(2.1); 8.203(3.1); 8.165(1.0); 8.147(1.7); 8.124(2.2); 8.102(1.2); 8.098(1.2); 7.987(1.1); 7.969(1.8); 7.951(0.9); 4.056(0.4); 4.039(1.1); 4.021(1.1); 4.003(0.4); 3.908(1.1); 3.884(16.0); 3.871(3.8); 3.853(1.1); 3.322(25.6); 2.672(0.5); 2.507(61.5); 2.503(79.8); 2.498(59.6); 2.329(0.4); 1.989(4.6); 1.397(2.1); 1.260(3.5); 1.242(7.7); 1.224(3.5); 1.193(1.3); 1.175(2.4); 1.158(1.2); 0.000(29.1)
Example I-25:

$^1$H-NMR(400.0 MHz, $d_6$-DMSO): δ =
8.896(2.3); 8.893(2.3); 8.700(2.5); 8.697(2.3); 8.569(4.0); 8.111(1.6); 8.096(1.6); 8.091(1.8); 8.080(1.6); 7.835(0.7); 7.832(0.7); 7.818(1.2); 7.814(1.5); 7.797(1.1); 7.793(1.0); 7.769(1.2); 7.766(1.2); 7.749(1.5); 7.732(0.7); 3.982(16.0); 3.319(54.7); 3.159(1.1); 3.140(3.5); 3.122(3.5); 3.104(1.1); 2.672(0.5); 2.507(51.6); 2.503(69.7); 2.498(51.9); 2.330(0.4); 1.397(2.4); 1.299(3.8); 1.280(8.0); 1.262(3.7); 0.008(1.8); 0.000(40.5); −0.008(1.7)
Example I-26:

$^1$H-NMR(400.0 MHz, $d_6$-DMSO): δ =
9.080(4.2); 8.356(1.5); 8.337(1.6); 8.305(1.5); 8.284(1.8); 8.203(2.6); 8.028(1.9); 8.005(3.0); 7.987(0.9); 7.984(0.9); 7.860(1.0); 7.857(1.0); 7.840(1.7); 7.822(0.8); 7.820(0.8); 7.768(1.4); 7.765(1.4); 7.746(1.2); 7.743(1.2); 4.320(16.0); 3.643(0.9); 3.624(1.0); 3.610(1.1); 3.591(1.0); 3.320(13.3); 3.031(1.0); 3.013(1.1); 2.998(1.0); 2.980(1.0); 2.676(0.4); 2.671(0.6); 2.667(0.4); 2.524(1.4); 2.511(34.4); 2.507(70.4); 2.502(92.9); 2.498(67.2); 2.494(32.9); 2.333(0.4); 2.329(0.5); 2.325(0.4); 1.989(0.4); 1.313(3.7); 1.295(8.0); 1.276(3.6); 1.231(0.4); 0.146(0.5); 0.008(3.3); 0.000(96.4); −0.008(4.1); −0.150(0.5)
Example I-27:

$^1$H-NMR(400.0 MHz, $d_6$-DMSO): δ =
9.013(3.9); 9.008(5.0); 8.972(4.4); 8.968(3.8); 8.555(7.2); 8.185(2.9); 8.164(3.2); 8.100(2.5); 8.081(2.8); 8.079(2.8); 7.850(1.2); 7.846(1.4); 7.832(2.2); 7.829(2.9); 7.825(1.5); 7.812(2.1); 7.808(2.0); 7.785(2.1); 7.782(2.5); 7.765(2.9); 7.762(2.4); 7.748(1.2); 7.745(1.3); 3.321(34.2); 3.248(1.9); 3.230(6.5); 3.212(6.6); 3.193(2.1); 3.078(1.1); 2.677(0.5); 2.672(0.8); 2.668(0.6); 2.525(1.7); 2.521.(2.6); 2.512(43.1); 2.508(92.6); 2.503(125.7); 2.499(91.2); 2.494(44.3); 2.334(0.5); 2.330(0.7); 2.325(0.5); 1.402(7.3); 1.384(16.0); 1.365(7.1); 1.350(0.4); 0.008(0.3); 0.000(11.2); −0.008(0.4)
Example I-28:

$^1$H-NMR(400.0 MHz, $d_6$-DMSO): δ =
9.097(9.4); 9.036(4.7); 9.032(5.7); 8.994(5.2); 8.411(3.4); 8.388(5.7); 8.365(4.1); 8.073(1.8); 8.054(3.2); 8.036(1.9); 7.922(2.4); 7.903(3.4); 7.884(1.8); 3.555(0.5); 3.536(1.8); 3.518(2.1); 3.502(2.3); 3.484(2.1); 3.465(0.6); 3.319(76.6); 3.020(0.6); 3.001(2.1); 2.983(2.3); 2.968(2.2); 2.949(1.9); 2.931(0.6); 2.671(2.4); 2.506(320.5); 2.502(411.7); 2.498(298.4); 2.328(2.4); 1.989(0.5); 1.397(0.8); 1.263(7.5); 1.245(16.0); 1.226(7.3); 1.175(0.4); 0.000(4.5)
Example I-29:

$^1$H-NMR(400.0 MHz, $d_6$-DMSO): δ =
8.537(7.6); 8.408(4.8); 8.405(4.9); 8.154(3.2); 8.142(5.2); 8.133(3.7); 8.120(6.0); 8.092(2.8); 8.073(3.1); 7.915(3.1); 7.911(3.1); 7.894(2.6); 7.890(2.6); 7.834(1.3); 7.830(1.5); 7.817(2.5); 7.813(3.0); 7.796(2.2); 7.792(2.0); 7.769(2.3); 7.767(2.4); 7.749(3.1); 7.732(1.3); 7.729(1.3); 3.321(49.4); 3.236(2.0); 3.218(6.7); 3.199(6.8); 3.181(2.2); 2.676(1.0); 2.672(1.3); 2.667(1.0); 2.525(2.9); 2.507(128.8); 2.503(169.0); 2.498(122.4); 2.334(1.0); 2.329(1.3); 2.325(1.0); 1.393(7.8); 1.375(16.0); 1.357(7.2); 0.000(4.8)
Example I-30:

$^1$H-NMR(400.0 MHz, $d_6$-DMSO): δ =
9.068(8.7); 8.425(5.6); 8.421(5.7); 8.393(3.1); 8.374(3.3); 8.345(3.4); 8.324(3.8); 8.185(5.1); 8.164(6.0); 8.053(1.8); 8.032(3.2); 8.014(1.8); 8.011(1.9); 7.936(3.3); 7.932(3.0); 7.915(2.7); 7.911(2.6); 7.900(2.2); 7.880(3.3); 7.862(1.8); 3.578(0.5); 3.559(1.9); 3.540(2.1); 3.525(2.3); 3.506(2.0); 3.487(0.7); 3.318(145.3); 3.027(0.7); 3.008(2.2); 2.990(2.3); 2.975(2.3); 2.956(1.9); 2.938(0.6); 2.675(3.6); 2.670(4.9); 2.666(3.6); 2.608(0.5); 2.524(13.1); 2.506(637.5); 2.502(820.8); 2.497(582.4); 2.333(3.4); 2.328(4.6); 2.324(3.5); 1.988(0.4); 1.398(3.3); 1.266(7.4); 1.248(16.0); 1.229(7.3); 1.167(0.3); 0.146(2.5); 0.008(20.7); 0.000(548.6); −0.008(20.5); −0.149(2.3)
Example I-31:

$^1$H-NMR(400.0 MHz, $d_6$-DMSO): δ =
13.309(3.9); 8.373(8.3); 8.084(3.5); 8.063(4.0); 8.032(3.2); 8.012(3.5); 7.844(2.7); 7.784(1.7); 7.781(1.8); 7.764(3.3); 7.747(2.1); 7.743(2.0); 7.680(2.4); 7.661(3.4); 7.643(1.6); 7.558(2.7); 3.321(90.4); 3.172(2.1); 3.153(6.8); 3.135(7.0); 3.117(2.2); 2.675(1.5); 2.671(2.0); 2.666(1.5); 2.524(4.7); 2.506(259.4); 2.502(340.0); 2.498(245.8); 2.333(1.5); 2.329(2.0); 2.324(1.5); 1.404(7.5); 1.386(16.0); 1.368(7.2); 1.312(0.3); 0.146(0.7); 0.008(5.3); 0.000(154.9); −0.008(6.2); −0.150(0.7)
Example I-32:

$^1$H-NMR(400.0 MHz, $d_6$-DMSO): δ =
8.541(8.1); 8.431(5.4); 8.196(3.8); 8.174(4.6); 8.158(3.4); 8.137(3.7); 8.094(3.0); 8.075(3.3); 7.946(3.0); 7.943(3.0); 7.925(2.6); 7.921(2.6); 7.836(1.4); 7.833(1.5); 7.819(2.6); 7.816(3.1); 7.798(2.3); 7.795(2.1); 7.771(2.4); 7.769(2.5); 7.751(3.3); 7.734(1.4); 3.322(44.3); 3.237(2.1); 3.218(7.0); 3.200(7.1);

-continued 3.182(2.3); 2.677(0.8); 2.672(1.0); 2.668(0.8); 2.508(124.2); 2.503(160.8); 2.499(118.4); 2.330(0.9); 2.325(0.7); 1.393(7.7); 1.374(16.0); 1.356(7.3); 0.000(17.4)
Example I-33:

$^1$H-NMR(400.0 MHz, d$_6$-DMSO): δ =
9.073(6.9); 8.444(4.4); 8.394(2.6); 8.374(2.8); 8.345(2.7); 8.323(3.1); 8.238(2.9); 8.216(3.4); 8.051(1.4); 8.033(2.4); 8.013(1.5); 7.964(2.4); 7.942(2.1); 7.900(1.8); 7.881(2.6); 7.862(1.4); 3.575(0.4); 3.557(1.3); 3.538(1.6); 3.523(1.6); 3.504(1.5); 3.486(0.5); 3.321(52.8); 3.021(0.4); 3.003(1.5); 2.984(1.8); 2.969(1.6); 2.951(1.4); 2.933(0.4); 2.671(1.0); 2.502(172.9); 2.329(1.0); 1.397(16.0); 1.276(5.4); 1.258(11.4); 1.240(5.3); 0.000(2.6)
Example I-34:

$^1$H-NMR(400.0 MHz, d$_6$-DMSO): δ =
8.526(4.4); 8.316(0.4); 8.159(3.3); 8.081(2.7); 8.060(3.1); 7.900(2.4); 7.878(2.9); 7.815(0.8); 7.796(1.6); 7.778(1.2); 7.750(1.4); 7.729(1.8); 7.713(2.5); 7.693(1.5); 3.906(16.0); 3.322(207.8); 3.143(1.2); 3.125(3.8); 3.107(3.9); 3.088(1.3); 2.671(1.8); 2.506(247.9); 2.502(313.4); 2.498(227.1); 2.328(1.7); 2.074(0.6); 1.292(4.1); 1.274(8.7); 1.255(3.9); 0.146(1.2); 0.008(12.9); 0.000(260.3); −0.149(1.2)
Example I-35:

$^1$H-NMR(400.0 MHz, d$_6$-DMSO): δ =
9.317(3.9); 8.590(4.2); 8.348(4.0); 8.346(4.1); 8.109(3.0); 8086(3.7); 7.842(0.7); 7.839(0.7); 7.825(1.3); 7.822(1.4); 7.804(1.0); 7.801(1.1); 7.779(1.2); 7.776(1.2); 7.758(1.4); 7.741(0.6); 7.739(0.7); 4.032(16.0); 3.157(1.1); 3.138(3.7); 3.120(3.8); 3.102(1.2); 2.513(14.0); 2.509(28.3); 2.504(37.2); 2.500(27.4); 1.396(8.0); 1.288(4.1); 1.269(8.7); 1.251(4.0); 1.197(0.4); 0.000(3.6)
Example I-36:

$^1$H-NMR(600.1 MHz, CD3CN): δ =
11.745(0.5); 8.966(6.6); 8.206(2.5); 8.192(2.7); 8.191(2.7); 8.163(2.3); 8.161(2.3); 8.149(2.4); 8.148(2.5); 7.936(1.6); 7.934(1.5); 7.925(1.9); 7.922(2.9); 7.920(1.5); 7.911(1.6); 7.908(1.5); 7.755(1.7); 7.753(1.7); 7.743(1.8); 7.741(3.0); 7.739(1.8); 7.730(1.5); 7.728(1.4); 7.579(1.4); 7.483(1.4); 3.575(0.6); 3.562(1.8); 3.552(0.8); 3.550(2.0); 3.540(2.1); 3.538(0.8); 3.528(2.0); 3.515(0.6); 2.984(0.6); 2.971(2.0); 2.959(2.2); 2.949(2.0); 2.947(0.9); 2.925(0.6); 2.130(50.4); 2.058(0.4); 2.054(0.6); 2.050(2.0); 2.046(0.6); 1.964(3.8); 1.956(6.9); 1.951(8.6); 1.948(62.4); 1.943(113.2); 1.939(164.6); 1.935(112.0); 1.931(56.5); 1.922(1.1); 1.833(0.4); 1.828(0.7); 1.824(0.9); 1.820(0.6); 1.816(0.3); 1.451(0.4); 1.340(0.7); 1.320(7.8); 1.308(16.0); 1.296(7.6); 1.285(1.1); 1.268(1.8); 0.881(0.4); 0.005(0.5); 0.000(16.1); −0.006(0.6)
Example I-37:

$^1$H-NMR(400.0 MHz, d$_6$-DMSO): δ =
8.829(2.3); 8.824(2.4); 8.659(2.4); 8.655(2.3); 8.574(4.0); 8.110(1.6); 8.102(1.4); 8.089(1.8); 8.082(1.6); 7.836(0.7); 7.833(0.7); 7.819(1.2); 7.815(1.5); 7.798(1.0); 7.794(1.0); 7.772(1.1); 7.768(1.2); 7.751(1.5); 7.734(0.7); 7.731(0.6); 3.989(16.0); 3.328(1.2); 3.164(1.1); 3.146(3.6); 3.127(3.7); 3.109(1.2); 2.673(0.4); 2.526(0.9); 2.512(23.0); 2.508(47.2); 2.504(62.5); 2.499(44.6); 2.495(21.3); 2.330(0.3); 1.301(3.9); 1.283(8.3); 1.265(3.8); 1.232(1.7); 0.008(0.4); 0.000(12.0); −0.009(0.4)
Example I-38:

$^1$H-NMR(400.0 MHz, d$_6$-DMSO): δ =
8.618(2.6); 8.553(4.3); 8.428(2.5); 8.100(2.0); 8.090(1.9); 8.079(2.3); 8.074(2.1); 7.825(0.9); 7.807(1.6); 7.790(1.2); 7.786(1.1); 7.760(1.3); 7.742(1.7); 7.724(0.8); 3.951(16.0); 3.814(0.5); 3.323(100.5); 3.156(1.2); 3.137(3.7); 3.119(3.8); 3.100(1.3); 2.671(1.3); 2.506(182.8); 2.502(229.6); 2.498(173.1); 2.329(1.2); 1.299(4.0); 1.281(8.3); 1.263(4.1); 1.235(3.3); 0.854(0.3); 0.146(0.8); 0.000(148.6); −0.149(0.7)
Example I-39:

$^1$H-NMR(400.0 MHz, d$_6$-DMSO): δ =
8.532(4.8); 8.427(0.4); 8.150(3.6); 8.089(4.0); 8.068(4.4); 7.958(2.1); 7.936(2.5); 7.819(0.9); 7.802(1.9); 7.782(1.4); 7.753(1.6); 7.733(4.3); 7.713(2.5); 3.923(16.0); 3.325(15.4); 3.140(1.2); 3.122(3.9); 3.104(4.0); 3.085(1.4); 2.805(0.6); 2.794(0.6); 2.671(0.5); 2.502(80.3); 2.329(0.5); 1.397(1.5); 1.347(0.4); 1.329(0.7); 1.311(0.4); 1.288(4.2); 1.269(8.6); 1.251(4.0); 0.000(9.9)
Example I-40:

$^1$H-NMR(400.0 MHz, CD3CN): δ =
9.101(3.4); 8.922(2.5); 8.916(2.5); 8.287(4.5); 8.180(3.7); 8.153(2.5); 8.147(2.4); 4.062(16.0); 3.219(1.2); 3.201(3.7); 3.183(3.8); 3.164(1.3); 3.131(1.1); 3.112(3.5); 3.094(3.5); 3.076(1.2); 2.131(29.4); 2.129(37.1); 2.113(0.7); 2.107(0.7); 2.100(0.5); 1.971(1.0); 1.963(2.8); 1.952(40.0); 1.945(73.2); 1.939(97.8); 1.933(67.1); 1.927(34.0); 1.774(0.4); 1.768(0.6); 1.762(0.4); 1.438(4.0); 1.420(8.0); 1.401(3.9); 1.361(3.9); 1.342(7.9); 1.324(3.7); 1.204(0.4); 0.000(1.5)
Example I-41:

$^1$H-NMR(400.0 MHz, CD3CN): δ =
9.656(2.7); 9.649(2.7); 9.429(5.4); 9.267(2.9); 9.261(2.6); 9.155(3.5); 8.217(3.8); 4.068(0.4); 4.050(0.4); 4.000(16.0); 3.944(1.2); 3.926(3.8); 3.907(3.8); 3.889(1.2); 3.440(1.1); 3.422(3.6); 3.403(3.7); 3.385(1.2); 2.463(0.6); 2.249(0.4); 2.230(0.4); 2.144(556.5); 2.119(2.0); 2.113(2.2); 2.107(2.5); 2.101(1.7); 2.095(0.9); 1.971(2.3); 1.964(9.6); 1.952(134.3); 1.946(247.3); 1.940(334.2); 1.933(228.1); 1.927(116.0); 1.780(0.7); 1.774(1.4); 1.768(1.8); 1.762(1.3); 1.756(0.6); 1.351(3.8); 1.333(7.7); 1.313(5.9); 1.293(7.9); 1.286(1.6); 1.275(5.1); 1.222(0.4); 1.203(0.7); 1.186(0.4); 0.908(0.5); 0.881(0.4) 0.000(25.0)
Example I'-42:

$^1$H-NMR(400.0 MHz, d$_6$-DMSO): δ =
9.531(4.5); 9.255(3.9); 8.638(1.7); 8.616(1.8); 8.391(1.6); 8.371(1.8); 8.285(4.2); 8.104(0.8); 8.102(0.9); 8.084(1.6); 8.066(1.0); 8.063(1.0); 7.960(1.2); 7.942(1.7); 7.922(0.9); 3.860(16.0); 3.386(0.9); 3.319(36.4); 2.854(1.3); 2.835(4.1); 2.817(4.2); 2.798(1.4); 2.672(0.4); 2.525(0.8); 2.512(19.0); 2.507(40.4); 2.503(57.2); 2.498(44.0); 2.494(22.1); 2.330(0.3); 1.236(0.4); 1.001(4.4); 0.983(9.2); 0.964(4.3); 0.008(1.7); 0.000(51.1); −0.008(2.1)
Example I'-43:

$^1$H-NMR(400.0 MHz, CDCl$_3$): δ =
9.131(1.1); 9.111(1.2); 9.108(1.1); 9.064(2.8); 9.052(0.4); 9.013(0.6); 8.871(1.0); 8.868(1.2); 8.850(1.1); 8.848(1.1); 8.184(0.4); 8.180(0.5); 8.166(1.1); 8.163(1.1); 8.146(1.2); 8.137(4.0); 8.124(0.6); 8.120(1.1); 8.116(1.1); 8.103(0.6); 8.099(0.4); 7.264(22.4); 5.301(3.3); 4.373(0.4); 4.339(0.5); 4.008(13.2); 3.989(2.7); 3.913(0.4); 3.900(0.7); 3.882(2.3); 3.863(2.3); 3.844(0.8); 3.778(0.4); 3.760(0.4); 3.416(0.4); 1.619(16.0); 1.501(3.0); 1.492(0.8); 1.482(6.3); 1.473(1.5); 1.463(3.0); 1.454(0.7); 1.256(0.9); 0.070(1.9); 0.000(3.1)

-continued

Example I'-44:

¹H-NMR(400.0 MHz, d₆-DMSO): δ =
9.805(5.2); 9.277(4.7); 8.954(2.1); 8.933(2.2); 8.518(1.9); 8.498(2.1); 8.248(5.0); 8.194(0.9); 8.176(1.7); 8.156(1.1); 8.060(1.5); 8.041(2.0); 8.022(1.1); 5.755(0.6); 3.886(16.0); 3.785(1.4); 3.766(1.4); 3.320(25.3); 2.672(0.4); 2.507(44.1); 2.503(58.0); 2.500(45.6); 2.330(0.4); 1.280(4.0); 1.261(8.3); 1.243(3.8); 0.001(13.6); 0.000(14.1)

Example I'-45:

¹H-NMR(300.1 MHz, d₆-DMSO): δ =
9.884(6.3); 9.464(1.7); 9.458(1.8); 9.450(1.8); 9.444(1.7); 8.955(1.5); 8.949(1.6); 8.927(1.7); 8.921(1.6); 8.858(2.4); 8.854(2.4); 8.606(2.5); 8.601(2.4); 8.083(1.7); 8.069(1.6); 8.055(1.6); 8.041(1.6); 7.906(0.4); 7.899(0.4); 7.546(0.4); 5.756(0.9); 3.977(1.0); 3.952(3.2); 3.927(3.3); 3.902(1.0); 3.745(16.0); 3.316(7.7); 2.514(4.6); 2.509(8.9); 2.503(11.6); 2.497(8.0); 1.235(0.8); 1.182(3.7); 1.158(8.1); 1.133(3.5); 0.000(5.7)

Example I-46:

¹H-NMR(400.0 MHz, d₆-DMSO): δ =
10.312(1.0); 9.681(6.0); 8.972(0.9); 8.800(9.0); 8.368(11.7); 8.164(0.4); 8.143(0.4); 8.075(0.5); 8.055(0.5); 8.019(3.2); 8.003(3.3); 7.999(3.8); 7.987(3.3); 7.811(0.3); 7.793(0.5); 7.748(1.6); 7.745(1.6); 7.731(2.4); 7.728(3.0); 7.710(2.0); 7.707(1.8); 7.655(2.3); 7.652(2.2); 7.635(3.2); 7.617(1.7); 7.084(1.3); 5.758(1.2); 3.322(39.8); 3.157(2.1); 3.139(6.9); 3.120(7.0); 3.102(2.3); 2.676(0.7); 2.672(1.0); 2.668(0.8); 2.525(2.2); 2.507(132.8); 2.503(172.9); 2.498(123.6); 2.334(0.8); 2.329(1.0); 2.325(0.8); 1.990(0.9); 1.398(1.7); 1.360(0.5); 1.352(0.8); 1.340(7.8); 1.321(16.0); 1.303(7.5); 1.274(0.3); 1.259(1.2); 1.250(0.7); 1.232(1.8); 1.193(0.5); 1.175(0.9); 1.158(0.5); 0.853(0.5); 0.842(0.3); 0.835(0.4); 0.147(0.4); 0.008(2.7); 0.000(87.3); − 0.007(3.3); −0.008(3.3); −0.149(0.4)

Example I'-47:

¹H-NMR(400.0 MHz, d₆-DMSO): δ =
9.806(4.4); 8.956(1.8); 8.934(1.9); 8.873(2.7); 8.611(2.7); 8.515(1.7); 8.495(1.8); 8.192(0.9); 8.174(1.5); 8.155(1.0); 8.153(1.1); 8.057(1.3); 8.038(1.8); 8.019(0.9); 4.038(0.3); 3.828(0.7); 3.808(1.9); 3.783(16.0); 3.752(3.0); 3.701(0.9); 3.645(0.4); 3.626(0.4); 3.323(184.7); 2.671(1.2); 2.506(162.5); 2.502(211.5); 2.498(167.4); 2.329(1.2); 1.988(1.4); 1.398(0.6); 1.339(0.4); 1.321(0.9); 1.292(4.0); 1.278(8.1); 1.255(4.0); 1.235(1.6); 1.220(0.9); 1.207(0.4); 1.201(0.5); 1.192(0.5); 1.175(0.8); 1.157(0.4); 0.981(0.4); 0.146(0.9); −0.001(180.5); −0.150(0.9)

Example I'-48:

¹H-NMR(400.0 MHz, d₆-DMSO): δ =
9.809(4.1); 9.654(0.3); 8.956(1.7); 8.934(1.8); 8.808(2.5); 8.804(2.5); 8.571(2.6); 8.567(2.5); 8.517(1.6); 8.497(1.7); 8.195(0.8); 8.177(1.4); 8.158(1.0); 8.061(1.2); 8.041(1.8); 8.023(0.9); 4.045(1.1); 3.825(0.7); 3.806(1.9); 3.788(16.0); 3.369(11.9); 2.671(1.1); 2.506(157.0); 2.502(197.3); 2.498(147.4); 2.329(1.2); 1.989(0.4); 1.453(0.6); 1.398(1.1); 1.290(3.5); 1.271(7.5); 1.253(3.6); 1.236(2.1); 0.146(0.5); 0.008(6.4); 0.000(105.6); −0.149(0.5)

Example I'-49:

¹H-NMR(400.0 MHz, d₆-DMSO): δ =
9.806(4.7); 9.299 (4.4); 8.951(1.9); 8.929(2.1); 8.517(1.7); 8.498(1.9); 8.272(4.6); 8.196(0.9); 8.178(1.6); 8.157(1.1); 8062(1.4); 8.043(1.9); 8.024(1.0); 4.038(0.4); 4.020(0.4); 3.884(16.0); 3.782(1.3); 3.764(1.3); 3.335(11.1); 2.671(0.9); 2.506(123.8); 2.502(160.6); 2.498(121.6); 2.329(0.9); 1.989(1.6); 1.277(4.1); 1.259(8.7); 1.240(4.5); 1.193(0.4); 1.175(0.8); 1.157(0.4); 0.146(0.4); 0.008(4.6); 0.000(90.8); −0.150(0.4)

Example I'-50:

¹H-NMR(400.0 MHz, d₆-DMSO): δ =
9.654(5.0); 9.326 (4.5); 9.234(1.5); 9.213(1.5); 8.453(1.7); 8.433(1.8); 8.323(4.9); 8.066(0.9); 8.048(1.7); 8.031(1.3); 8.027(1.3); 7.996(1.5); 7.978(1.8); 7.959(0.8); 4.105(16.0); 4.038(0.4); 3.884(0.3); 3.767(0.7); 3.749(0.9); 3.735(1.4); 3.717(1.3); 3.698(0.4); 3.684(0.4); 3.666(1.3); 3.647(1.4); 3.634(0.8); 3.628(0.5); 3.615(0.7); 3.323(114.7); 2.675(1.0); 2.671(1.4); 2.666(1.0); 2.506(178.7); 2.502(236.7); 2.497(177.5); 2.333(1.0); 2.329(1.3); 2.324 (1.0); 1.989(1.5); 1.435(3.9); 1.416(8.3); 1.398(3.9); 1.259(0.7); 1.234(0.7); 1.193(0.4); 1.175(0.8); 1.157(0.4); 0.146(0.6); 0.008(6.3); 0.000(145.6); −0.008(7.2); −0.150(0.6)

Example I'-51:

¹H-NMR(400.1.MHz, d₆-DMSO): δ =
9.990(4.2); 9.839(0.4); 9.166(1.5); 9.144(1.7); 9.048(2.3); 8.896(2.4); 8.893(2.4); 8.644(2.5); 8.640(2.5); 8.450(1.4); 8.445(1.3); 8.427(1.3); 8.422(1.3); 4.086(1.3); 3.886(0.6); 3.867(1.8); 3.849(1.8); 3.830(0.7); 3.803(16.0); 3.325(50.7); 3.301(0.6); 2.511(16.3); 2.507(32.4); 2.502(42.6); 2.498(30.2); 1.989(0.3); 1.505(0.6); 1.310(3.7); 1.292(8.1); 1.273(3.7); 1.234(2.0); 0.940(0.3); 0.008(1.1); 0.000(27.8); −0.008(1.1)

Example I'-52:

¹H-NMR(400.0 MHz, d₆-DMSO): δ =
9.796(4.4); 9.286(4.0); 8.949(1.7); 8.928(1.9); 8.518(1.6); 8.497(1.7); 8.245(4.3); 8.202(0.8); 8.199(0.9); 8.185(1.1); 8.181(1.5); 8.163(1.0); 8.160(1.0); 8.061(1.2); 8.043(1.8); 8.024(0.9); 5.757(7.5); 4.122(0.7); 4.039(0.3); 4.021(0.3); 3.924(16.0); 3.643(15.0); 3.430(0.7); 3.327(44.1); 2.512(14.8); 2.508(29.0); 2.503(38.1); 2.499(28.3); 1.990(1.5); 1.193(0.4); 1.175(0.8); 1.158(0.4); 0.008(2.2); 0.000(43.4); −0.008(1.8)

Example I'-53:

¹H-NMR(400.0 MHz, d₆-DMSO): δ =
9.839(4.4); 8.941(1.7); 8.920(1.9); 8.714(6.3); 8.549(1.6); 8.529(1.7); 8.232(0.8); 8.229(0.8); 8.214(1.1); 8.211(1.6); 8.193(1.0); 8.189(1.0); 8.095(1.2); 8.075(1.8); 8.057(0.9); 4.039(0.5); 4.021(0.6); 4.003(0.4); 3.990(16.0); 3.639(14.8); 3.321(26.3); 2.525(0.9); 2.511(17.4); 2.507(35.5); 2.503(48.7); 2.498(37.1); 1.989(2.2); 1.193(0.6); 1.175(1.2); 1.158(0.6); 0.008(2.0); 0.000(52.4); −0.008(2.1)

Example I'-54:

¹H-NMR(400.0 MHz, d₆-DMSO): δ =
9.847(4.7); 8.937(1.8); 8.916(2.0); 8.717(6.4); 8.549(1.7); 8.529(1.8); 8.226(0.8); 8.223(0.9); 8.208(1.2); 8.205(1.6); 8.186(1.0); 8.183(1.0); 8.091(1.3); 8.073(1.9); 8.054(0.9); 3.952(16.0); 3.781(0.7); 3.762(1.9); 3.744(1.9); 3.726(0.7); 3.320(59.5); 2.675(0.5); 2.671(0.6); 2.667(0.5); 2.506(72.1); 2.502(98.9); 2.498(76.0); 2.333(0.4); 2.329(0.6); 2.325(0.5); 1.989(1.0); 1.398(0.9); 1.277(3.8); 1.259(8.2); 1.240(3.8); 1.175(0.5); 0.146(0.4); 0.008(3.6) 0.000(90.1); −0.008(4.1); −0.150(0.4)

Example I-55:

¹H-NMR(600.1 MHz, d₆-DMSO): δ =
9.449(6.4); 9.348(6.1); 9.249(9.4); 8.769(10.1); 8.577(5.6); 8.573(5.7); 8.217(4.2); 8.202(5.2); 8.074(3.6); 8.070(3.6); 8.059(3.0); 8.055(3.0); 4.175(2.1); 4.163(7.0); 4.150(7.0); 4.138(2.2); 4.025(0.3); 3.327(87.0); 2.617(0.4); 2.526(0.8); 2.523(1.0); 2.520(1.2); 2.508(46.7); 2.505(63.1); 2.502(48.2); 2.389(0.4); 1.991(1.4); 1.397(1.5); 1.307(7.4); 1.295(16.0); 1.282(7.3); 1.188(0.4); 1.176(0.7); 1.165(0.4); 0.005(0.5); 0.000(11.7)

Example I-56:

$^1$H-NMR(400.0 MHz, d$_6$-DMSO): δ =
9.467(6.2); 9.350(6.1); 9.302(9.1); 8.754(10.4); 8.480(5.2); 8.458(5.7); 8.337(0.7); 8.315(0.7); 8.280(4.9); 8.275(5.1); 7.918(3.6); 7.913(3.5); 7.896(3.4); 7.891(3.4); 7.720(0.3); 7.699(0.4); 7.355(0.6); 7.350(0.4); 7.299(0.5); 7.283(0.7); 7.272(0.7); 4.180(1.9); 4.161(6.7); 4.143(6.8); 4.124(2.0); 4.038(0.4); 4.020(0.5); 3.318(243.1); 2.689(0.4); 2.675(2.1); 2.671(2.9); 2.666(2.2); 2.524(9.5); 2.510(168.3); 2.506(345.7); 2.502(476.8); 2.497(360.5); 2.493(179.4); 2.333(2.0); 2.328(2.8); 2.324(2.0); 1.989(2.0); 1.649(0.8); 1.398(0.7); 1.315(7.2); 1.296(16.0); 1.278(7.0); 1.236(0.7); 1.193(0.5); 1.175(1.0); 1.157(0.5); 1.105(0.3); 0.146(1.9); 0.008(15.6); 0.000(415.4); −0.008(16.8); −0.150(1.8)

Example I-57:

$^1$H-NMR(400.0 MHz, d$_6$-DMSO): δ =
9.449(6.0); 9.345(5.9); 9.246(9.0); 8.767(10.0); 8.418(3.1); 8.399(3.2); 8.212(3.0); 8.190(4.0); 8.088(1.9); 8.084(2.0); 8.071(2.4); 8.067(3.3); 8.063(1.8); 8.049(1.7); 8.046(1.7); 7.877(2.0); 7.874(2.2); 7.857(3.5); 7.839(1.7); 7.837(1.7); 4.177(2.0); 4.159(6.7); 4.140(6.8); 4.122(2.0); 3.321(82.5); 2.676(0.6); 2.672(0.8); 2.667(0.6); 2.525(2.6); 2.512(45.0); 2.507(93.8); 2.503(130.7); 2.498(100.0); 2.494(50.3); 2.334(0.6); 2.330(0.8); 2.325(0.6); 2.075(3.4); 1.316(7.1); 1.297(16.0); 1.279(7.0); 1.233(0.5); 0.146(0.6); 0.008(5.0); 0.000(132.8); −0.008(5.6); −0.150(0.6)

Example I'-58:

$^1$H-NMR(601.6 MHz, d$_6$-DMSO): δ =
9.774(4.2); 8.964(1.7); 8.950(1.8); 8.488(1.6); 8.475(1.6); 8.165(0.8); 8.163(0.8); 8.153(1.1); 8.151(1.6); 8.149(1.0); 8.139(1.0); 8.137(0.9); 8.068(2.6); 8.027(1.1); 8.015(1.8); 8.003(0.9); 7.937(1.8); 7.923(2.0); 7.712(1.5); 7.710(1.5); 7.698(1.3); 7.696(1.3); 4.036(0.4); 4.024(0.4); 3.819(0.8); 3.780(16.0); 3.307(52.0); 2.615(0.6); 2.612(0.8); 2.609(0.6); 2.521(1.6); 2.518(2.1); 2.515(2.4); 2.506(49.3); 2.503(98.4); 2.500(132.6); 2.497(99.9); 2.495(50.3); 2.387(0.6); 2.384(0.8); 2.381(0.6); 1.988(1.7); 1.907(1.0); 1.287(3.8); 1.274(8.1); 1.262(3.8); 1.235(0.5); 1.187(0.5); 1.175(0.9); 1.163(0.5); 0.005(1.4); 0.000(33.4); −0.006(1.5)

Example I-59:

$^1$H-NMR(601.6 MHz, d$_6$-DMSO): δ =
9.313(3.6); 8.347(3.0); 8.331(3.3); 8.324(3.9); 7.870(1.7); 7.865(1.8); 7.854(1.6); 7.850(1.7); 7.741(2.9); 7.737(2.7); 4.060(15.2); 3.968(16.0); 3.776(1.1); 3.763(3.8); 3.751(3.9); 3.739(1.2); 3.309(240.8); 3.281(0.4); 2.615(0.8); 2.612(1.1); 2.609(0.8); 2.521(2.2); 2.518(2.7); 2.515(2.9); 2.506(66.9); 2.503(136.7); 2.500(184.0); 2.497(137.4); 2.495(66.9); 2.388(0.8); 2.385(1.1); 2.382(0.8); 2.072(0.9); 1.255(4.1); 1.243(8.8); 1.230(4.0); 0.005(1.4); 0.000(37.9); −0.006(1.5)

APPLICATION EXAMPLES

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml test tube by turning and rocking on an orbital shaker (rocking rotation at 30 rpm for 2 h). With 900 ppm active ingredient solution and internal surface area 44.7 cm$^2$, given homogeneous distribution, an area-based dose of 5 μg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/cm$^2$. 100% efficacy means that all the fleas were dead or moribund. 0% efficacy means that no fleas were harmed.

In this test, for example, the following compounds from the preparation examples show an efficacy of 100% at an application rate of 5 μg/cm$^2$ (=500 g/ha): I-1

*Ctenocephalides felis*—Oral Test

| Solvent: | dimethyl sulphoxide |
|---|---|

For the purpose of production of a suitable active ingredient preparation, 10 mg of active ingredient are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-1

*Lucilia cuprina* Test

| Solvent: | dimethyl sulphoxide |
|---|---|

To produce a suitable active ingredient preparation, 10 mg of active ingredient are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active ingredient preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-1

*Musca domestica* Test

| Solvent: | dimethyl sulphoxide |
|---|---|

To produce a suitable active ingredient preparation, 10 mg of active ingredient are mixed with 0.5 ml of dimethyl sulphoxide, and the concentrate is diluted with water to the desired concentration.

Vessels containing a sponge treated with sugar solution and the active ingredient preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 75% at an application rate of 4 ppm: I-1

*Meloidogyne incognita* Test

| Solvent: | 125.0 parts by weight of acetone |
|---|---|

To produce a suitable preparation of active ingredient, 1 part by weight of active ingredient is mixed with the stated amount of solvent and the concentrate is diluted with water to the desired concentration.

Vessels are filled with sand, active ingredient solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: I-32

In this test, for example, the following compounds from the preparation examples show an efficacy of 90% at an application rate of 20 ppm: I-40

In this test, for example, the following compounds from the preparation examples show an efficacy of 70% at an application rate of 20 ppm: I-1

*Myzus persicae*—Spray Test

| Solvent: | 78 parts by weight of acetone |
|---|---|
| | 1.5 parts by weight of dimethylformamide |
| Emulsifier: | alkylaryl polyglycol ether |

To produce a suitable active ingredient preparation, 1 part by weight of active ingredient is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient preparation of the desired concentration.

After 5-6 days, the efficacy in % is determined. 100% means that all the aphids have been killed; 0% means that no aphids have been killed.

In this test, for example, the following compounds from the preparation examples show an efficacy of 100% at an application rate of 500 g/ha: I-13

In this test, for example, the following compounds from the preparation examples show an efficacy of 90% at an application rate of 500 g/ha: I-6, I-7, I-8, I-10, I-12, I-14, I-16, I-17, I-41, I'-42, I'-44

In this test, for example, the following compounds from the preparation examples show an efficacy of 70% at an application rate of 500 g/ha: I-5, I-11, I-30

In this test, for example, the following compounds from the preparation examples show an efficacy of 100% at an application rate of 100 g/ha: I-2, I-18, I-20, I-21, I-22, I-23

In this test, for example, the following compounds from the preparation examples show an efficacy of 90% at an application rate of 100 g/ha: I-1, I-19

*Phaedon cochleariae*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active ingredient preparation, 1 part by weight of active ingredient is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active ingredient preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: I-1, I-5, I-7, I-8, I-10, I-11, I-12, I-14, I-15, I-16, I-17, I-25

In this test, for example, the following compounds from the preparation examples show an efficacy of 83% at an application rate of 500 g/ha: I-6, I-30, I-35, I'-44

In this test, for example, the following compounds from the preparation examples show an efficacy of 100% at an application rate of 100 g/ha: I-13, I-18, I-19, I-20, I-21, I-23

*Spodoptera frugiperda*—Spray Test

| Solvent: | 78.0 parts by weight of acetone |
|---|---|
| | 1.5 parts by weight of dimethylformamide |
| Emulsifier: | alkylaryl polyglycol ether |

To produce a suitable active ingredient preparation, 1 part by weight of active ingredient is dissolved with the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active ingredient preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 500 g/ha: I-1, I-2, I-5, I-6, I-7, I-8, I-10, I-11, I-12, I-14, I-15, I-16, I-17, I-25, I-30, I-35, I'-44

In this test, for example, the following compounds from the preparation examples show an efficacy of 83% at an application rate of 500 g/ha: I-13

In this test, for example, the following compounds from the preparation examples show an efficacy of 100% at an application rate of 100 g/ha: I-19, I-18, I-20, I-21, I-22, I-23

*Tetranychus urticae*—Spray Test, OP-Resistant

| Solvent: | 78.0 parts by weight of acetone |
| | 1.5 parts by weight of dimethylformamide |
| Emulsifier: | alkylaryl polyglycol ether |

To produce a suitable active ingredient preparation, 1 part by weight of active ingredient is dissolved with the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active ingredient preparation of the desired concentration.

After 6 days, the efficacy in % is determined. 100% means that all the spider mites have been killed; 0% means that no spider mites have been killed.

In this test, for example, the following compounds from the preparation examples show an efficacy of 70% at an application rate of 500 g/ha: I'-42

In this test, for example, the following compounds from the preparation examples shows an efficacy of 100% at an application rate of 100 g/ha: I-34

In this test, for example, the following compounds from the preparation examples shows an efficacy of 90% at an application rate of 100 g/ha: I-22, I-36, I-37

In this test, for example, the following compounds from the preparation examples show an efficacy of 70% at an application rate of 100 g/ha: I-4, I-18, I-29

In this test, for example, the following compounds from the preparation examples show an efficacy of 100% at an application rate of 20 g/ha: I-23

In this test, for example, the following compounds from the preparation examples shows an efficacy of 70% at an application rate of 20 g/ha: I-21, I-40

The invention claimed is:

1. A compound of formula (I) or (I')

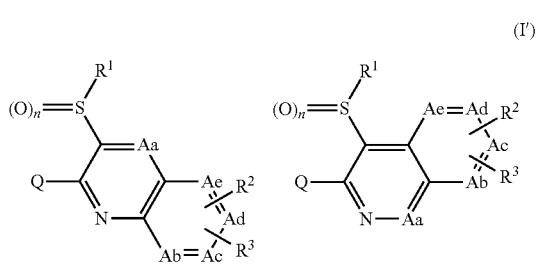

wherein
Aa is nitrogen or $=C(R^7)-$,
Ab is nitrogen or $=C(H)-$,
Ac is nitrogen or $=C(H)-$,
Ad is nitrogen or $=C(H)-$,
Ae is nitrogen or $=C(H)-$,
where Ab, Ac, Ad and Ae cannot all be nitrogen,
$R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di-$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$-alkyl, $(C_1-C_6)$alkylsulphinyl-$(C_1-C_6)$-alkyl, $(C_1-C_6)$haloalkylsulphinyl-$(C_1-C_6)$alkyl, $(C_1-C_6)$alkylsulphonyl-$(C_1-C_6)$alkyl, $(C_1-C_6)$haloalkylsulphonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulphinyl-$(C_1-C_6)$alkyl, $(C_1-C_6)$alkoxy-$(C_1-C_6)$alkylsulphonyl-$(C_1-C_6)$-alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulphonylamino, aminosulphonyl-$(C_1-C_6)$alkyl, $(C_1-C_6)$alkylaminosulphonyl-$(C_1-C_6)$alkyl, di-$(C_1-C_6)$alkylaminosulphonyl-$(C_1-C_6)$alkyl,
or $(C_1-C_6)$alkyl, $(C_1-C_6)$alkoxy, $(C_2-C_6)$alkenyl, $(C_2-C_6)$alkynyl, $(C_3-C_8)$cycloalkyl, each optionally mono- or polysubstituted identically or differently by aryl, hetaryl or heterocyclyl, where aryl, hetaryl or heterocyclyl may each optionally be mono- or polysubstituted identically or differently by halogen, cyano, nitro, hydroxyl, amino, carboxyl, carbamoyl, aminosulphonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl, or
$R^1$ is aryl, hetaryl or heterocyclyl, each mono- or polysubstituted identically or differently by halogen, cyano, nitro, hydroxyl, amino, carboxyl, carbamoyl, $(C_1-C_6)$alkyl, $(C_3-C_8)$cycloalkyl, $(C_1-C_6)$-alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl, (=O) (in the case of heterocyclyl only) and $(=O)_2$ (in the case of heterocyclyl only),
$R^2$, $R^3$ are independently hydrogen, cyano, halogen, nitro, acetyl, hydroxyl, amino, SCN, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$ cycloalkyl, (C₁-C₆)alkyl, (C₁-C₆)haloalkyl, (C₁-C₆)cyanoalkyl, (C₁-C₆)hydroxyalkyl, hydroxycarbonyl-(C₁-C₆)-alkoxy, (C₁-C₆)alkoxycarbonyl-(C₁-C₆)alkyl, (C₁-C₆)alkoxy-(C₁-C₆)alkyl, (C₂-C₆)alkenyl, (C₂-C₆)haloalkenyl, (C₂-C₆)cyanoalkenyl, (C₂-C₆)alkynyl, (C₂-C₆)haloalkynyl, (C₂-C₆)cyanoalkynyl, (C₁-C₆)alkoxy, (C₁-C₆)haloalkoxy, (C₁-C₆)cyanoalkoxy, (C₁-C₆)alkoxycarbonyl-(C₁-C₆)alkoxy, (C₁-C₆)alkoxy-(C₁-C₆)alkoxy, (C₁-C₆)alkylhydroxyimino, (C₁-C₆)alkoxyimino, (C₁-C₆)alkyl-(C₁-C₆)alkoxyimino, (C₁-C₆)haloalkyl-(C₁-C₆)alkoxyimino, (C₁-C₆)alkylthio, (C₁-C₆)haloalkylthio, (C₁-C₆)alkoxy-(C₁-C₆)alkylthio, (C₁-C₆)alkylthio-(C₁-C₆)alkyl, (C₁-C₆)alkylsulphinyl, (C₁-C₆)haloalkylsulphinyl, (C₁-C₆)alkoxy-(C₁-C₆)alkylsulphinyl, (C₁-C₆)alkylsulphinyl-(C₁-C₆)alkyl, (C₁-C₆)alkylsulphonyl, (C₁-C₆)haloalkylsulphonyl, (C₁-C₆)alkoxy-(C₁-C₆)alkylsulphonyl, (C₁-C₆)alkylsulphonyl-(C₁-C₆)alkyl, (C₁-C₆)alkylsulphonyloxy, (C₁-C₆)alkylcarbonyl, (C₁-C₆)alkylthiocarbonyl, (C₁-C₆)haloalkylcarbonyl, (C₁-C₆)alkylcarbonyloxy, (C₁-C₆)alkoxycarbonyl, (C₁-C₆)haloalkoxycarbonyl, aminocarbonyl, (C₁-C₆)alkylaminocarbonyl, di-(C₁-C₆)alkylaminocarbonyl, (C₁-C₆)alkylaminothiocarbonyl, di-(C₁-C₆)alkylaminothiocarbonyl, (C₂-C₆)alkenylaminocarbonyl, di-(C₂-C₆)-alkenylaminocarbonyl, (C₃-C₈)cycloalkylaminocarbonyl, (C₁-C₆)alkylsulphonylamino, (C₁-C₆)alkylamino, di-(C₁-C₆)alkylamino, aminosulphonyl, (C₁-C₆)alkylaminosulphonyl, di-(C₁-C₆)alkylaminosulphonyl, (C₁-C₆)alkylsulphoximino, aminothiocarbonyl, (C₁-C₆)alkylaminothiocarbonyl, di-(C₁-C₆)alkylaminothiocarbonyl, (C₃-C₈)cycloalkylamino or NHCO—(C₁-C₆)alkyl ((C₁-C₆)alkylcarbonylamino), R⁷ is hydrogen, cyano, halogen, acetyl, hydroxyl, amino, (C₃-C₈)cycloalkyl, halo(C₃-C₈)cycloalkyl, (C₁-C₆)alkyl, (C₁-C₆)haloalkyl, (C₁-C₆)cyanoalkyl, (C₂-C₆)alkenyl, (C₂-C₆)haloalkenyl, (C₂-C₆)alkynyl, (C₂-C₆)haloalkynyl, (C₁-C₆)alkoxy, (C₁-C₆)haloalkoxy, (C₁-C₆)alkylthio, (C₁-C₆)haloalkylthio, (C₁-C₆)alkylsulphinyl, (C₁-C₆)haloalkylsulphinyl, (C₁-C₆)alkylsulphonyl or (C₁-C₆)haloalkylsulphonyl, Q is a partly saturated or saturated heterocyclic or heteroaromatic 8-, 9-, 10-, 11- or 12-membered fused bicyclic or tricyclic ring system, where at least one carbonyl group may optionally be present and/or where the ring system is optionally mono- or polysubstituted identically or differently, and where the substituents may independently be selected from hydrogen, cyano, halogen, nitro, acetyl, hydroxyl, amino, SCN, tri(C₁-C₆)alkylsilyl, (C₃-C₈)cycloalkyl, (C₃-C₈)cycloalkyl-(C₃-C₈)cycloalkyl, (C₁-C₆)alkyl-(C₃-C₈)cycloalkyl, halo(C₃-C₈)cycloalkyl, (C₁-C₆)alkyl, (C₁-C₆)haloalkyl, (C₁-C₆)cyanoalkyl, (C₁-C₆)hydroxyalkyl, hydroxycarbonyl-(C₁-C₆)alkoxy, (C₁-C₆)alkoxycarbonyl-(C₁-C₆)alkyl, (C₁-C₆)alkoxy-(C₁-C₆)alkyl, (C₂-C₆)alkenyl, (C₂-C₆)haloalkenyl, (C₂-C₆)cyanoalkenyl, (C₂-C₆)alkynyl, (C₂-C₆)alkynyloxy-(C₁-C₄)alkyl, (C₂-C₆)haloalkynyl, (C₂-C₆)cyanoalkynyl, (C₁-C₆)alkoxy, (C₁-C₆)haloalkoxy, (C₁-C₆)haloalkoxy-(C₁-C₆)alkyl, (C₂-C₆)alkenyloxy-(C₁-C₆)alkyl, (C₂-C₆)haloalkenyloxy-(C₁-C₆)alkyl, (C₁-C₆)cyanoalkoxy, (C₁-C₆)alkoxycarbonyl-(C₁-C₆)alkoxy, (C₁-C₆)alkoxy-(C₁-C₆)alkoxy, (C₁-C₆)alkylhydroxyimino, (C₁-C₆)alkoxyimino, (C₁-C₆)alkyl-(C₁-C₆)alkoxyimino, (C₁-C₆)haloalkyl-(C₁-C₆)alkoxyimino, (C₁-C₆)alkylthio, (C₁-C₆)haloalkylthio, (C₁-C₆)alkoxy-(C₁-C₆)alkylthio, (C₁-C₆)alkylthio-(C₁-C₆)alkyl, (C₁-C₆)alkylsulphinyl, (C₁-C₆)haloalkylsulphinyl, (C₁-C₆)alkoxy-(C₁-C₆)alkylsulphinyl, (C₁-C₆)alkylsulphinyl-(C₁-C₆)alkyl, (C₁-C₆)alkylsulphonyl, (C₁-C₆)haloalkylsulphonyl, (C₁-C₆)alkoxy-(C₁-C₆)alkylsulphonyl, (C₁-C₆)alkylsulphonyl-(C₁-C₆)alkyl, (C₁-C₆)alkylsulphonyloxy, (C₁-C₆)alkylcarbonyl, (C₁-C₆)alkylcarbonyl-(C₁-C₆)alkyl, (C₁-C₆)alkylthiocarbonyl, (C₁-C₆)haloalkylcarbonyl, (C₁-C₆)alkylcarbonyloxy, (C₁-C₆)alkoxycarbonyl, (C₁-C₆)haloalkoxycarbonyl, aminocarbonyl, (C₁-C₆)alkylaminocarbonyl, (C₁-C₆)alkylaminothiocarbonyl, di-(C₁-C₆)alkylaminocarbonyl, di-(C₁-C₆)alkylaminothiocarbonyl, (C₂-C₆)alkenylaminocarbonyl, di-(C₂-C₆)-alkenylaminocarbonyl, (C₃-C₈)cycloalkylaminocarbonyl, (C₁-C₆)alkylsulphonylamino, (C₁-C₆)alkylamino, di-(C₁-C₆)alkylamino, aminosulphonyl, (C₁-C₆)alkylaminosulphonyl, di-(C₁-C₆)alkylaminosulphonyl, (C₁-C₆)alkylsulphoximino, aminothiocarbonyl, (C₁-C₆)alkylaminothiocarbonyl, di-(C₁-C₆)alkylaminothiocarbonyl, (C₃-C₈)cycloalkylamino, NHCO—(C₁-C₆)alkyl ((C₁-C₆)alkylcarbonylamino), or where the substituents may independently be selected from phenyl or a 5- or 6-membered heteroaromatic ring, where phenyl or the ring may optionally be mono- or polysubstituted identically or differently by C₁-C₆-alkyl, C₂-C₆-alkenyl, C₂-C₆-alkynyl, C₃-C₆-cycloalkyl, C₁-C₆-haloalkyl, C₂-C₆-haloalkenyl, C₂-C₆-haloalkynyl, C₃-C₆-halocycloalkyl, halogen, CN, NO₂, C₁-C₄-alkoxy, C₁-C₄-haloalkoxy, n is 0, 1 or 2, where, in the case of the structural unit A4, Q is none of the following ring systems:

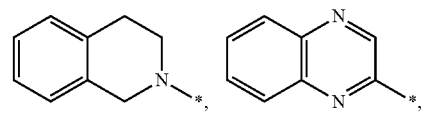

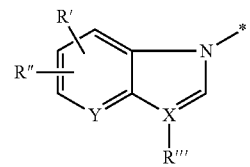

where X and Y, which may be the same or different, are carbon or nitrogen, R''' is hydrogen, aldehyde, oxime or —C(O)O—R_a, with the proviso that X is carbon, where R_a is C₁-C₆-alkyl, R' and R'', which may be the same or different, are hydrogen, halogen, cyano, nitro, C₁-C₆-alkyl or C₁-C₆-alkoxy, and, in addition, when Aa is =C(H)—, in the case of the compounds of the formula (I), Q is not Q1, Q2, Q3, Q4, Q5, Q6, Q7, Q8, Q9, Q10, Q15, or Q17;

with the proviso that the compound of formula (I) or (I') is not

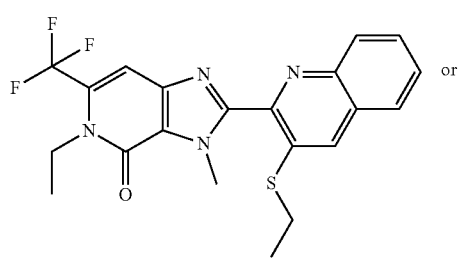
or
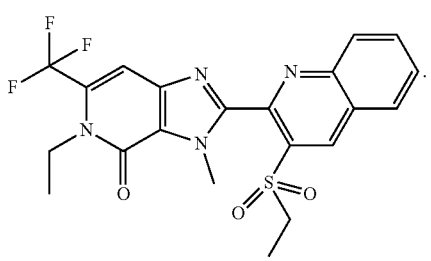
.
2. The compound of formula (I) or (I') according to claim 1, wherein
Aa is nitrogen or =C(R$^7$)—,
Ab is nitrogen or =C(H)—,
Ac is nitrogen or =C(H)—,
Ad is nitrogen or =C(H)—,
Ae is nitrogen or =C(H)—,
where Ab, Ac, Ad and Ae cannot all be nitrogen,
optionally resulting in one of the following structural units A1 to A44:
A1
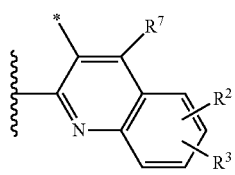
A2
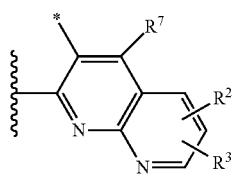
A3
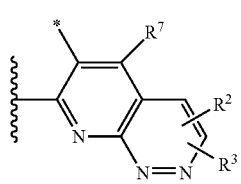
A4
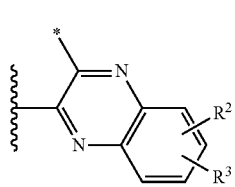
A5
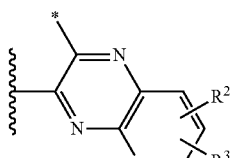
A6
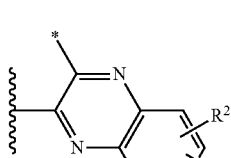
A7
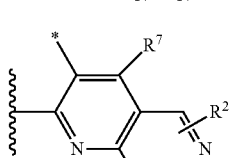
A8
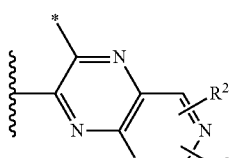
A9
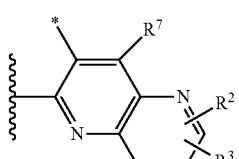
A10
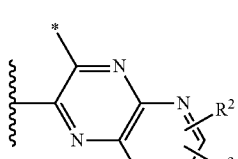
A11
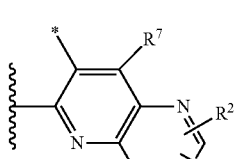
A12
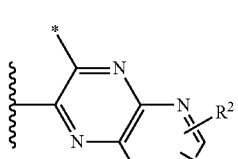
A13
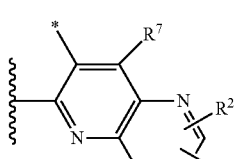

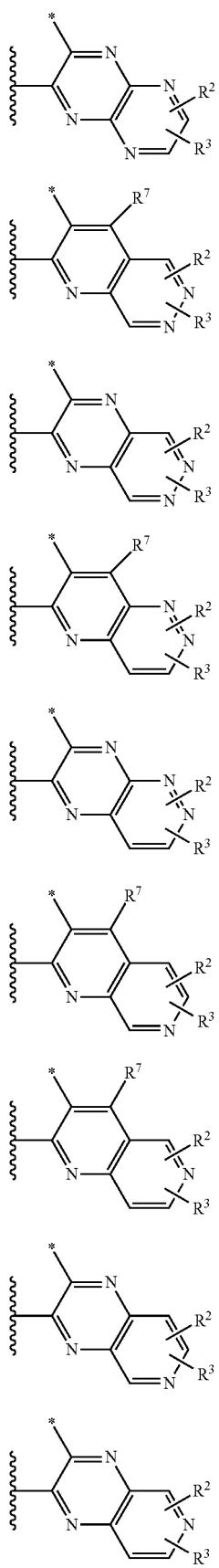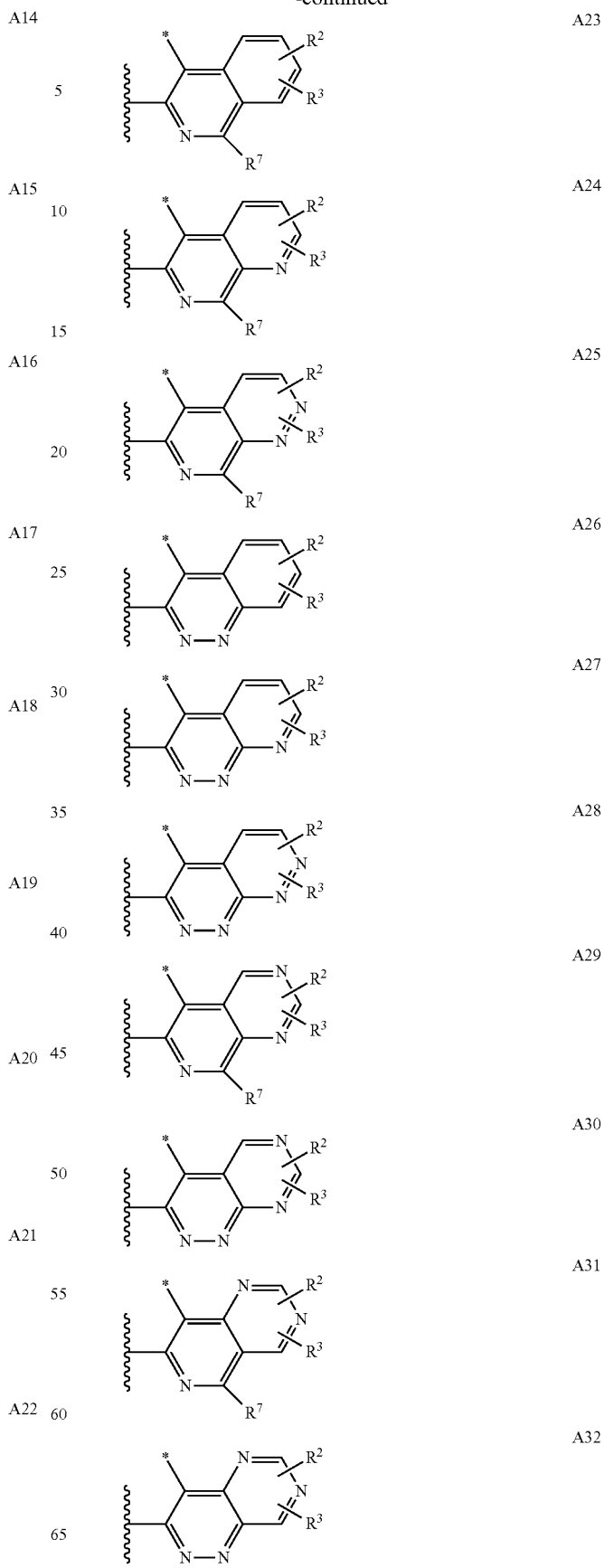

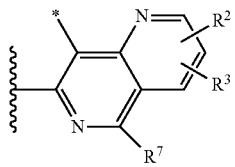
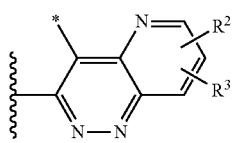
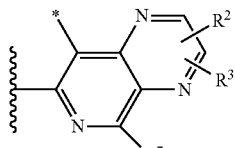
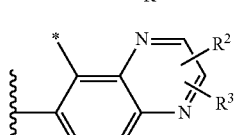
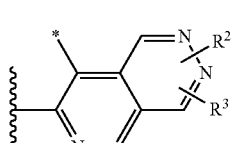
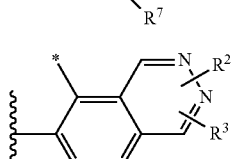
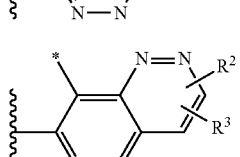
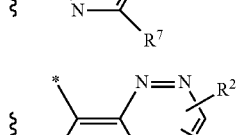
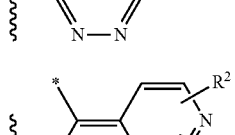
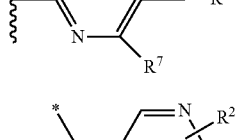
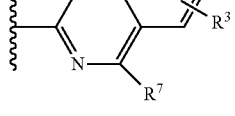

A33

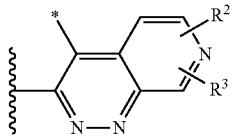

A34

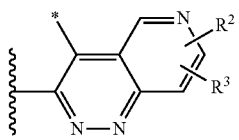

where the bond to the substituent Q is identified by a wavy line and the bond to the sulphur atom by an asterisk *, $R^1$ is $(C_1-C_4)$alkyl, $(C_1-C_4)$hydroxyalkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyloxy-$(C_1-C_4)$alkyl, $(C_2-C_4)$haloalkynyl, $(C_2-C_4)$cyanoalkynyl, $(C_3-C_6)$cycloalkyl, $(C_3-C_6)$cycloalkyl$(C_3-C_6)$cycloalkyl, $(C_1-C_4)$alkyl-$(C_3-C_6)$cycloalkyl, halo$(C_3-C_6)$cycloalkyl, $(C_1-C_4)$alkylamino, di-$(C_1-C_4)$alkylamino, $(C_3-C_6)$cycloalkylamino, $(C_1-C_4)$alkylcarbonylamino, $(C_1-C_4)$alkylthio-$(C_1-C_4)$alkyl, $(C_1-C_4)$haloalkylthio-$(C_1-C_4)$alkyl, $(C_1-C_4)$alkylsulphinyl-$(C_1-C_4)$alkyl, $(C_1-C_4)$haloalkylsulphinyl-$(C_1-C_4)$alkyl, $(C_1-C_4)$alkylsulphonyl-$(C_1-C_4)$alkyl, $(C_1-C_4)$alkylcarbonyl-$(C_1-C_4)$alkyl, $(C_1-C_4)$haloalkylcarbonyl-$(C_1-C_4)$alkyl, $(C_1-C_4)$alkylsulphonylamino, or is $(C_1-C_4)$alkyl, $(C_1-C_4)$alkoxy, $(C_2-C_4)$alkenyl, $(C_2-C_4)$alkynyl, $(C_3-C_6)$cycloalkyl, each optionally mono- or disubstituted identically or differently by aryl, hetaryl and heterocyclyl, where aryl, hetaryl and heterocyclyl may each optionally be mono- or disubstituted identically or differently by halogen, cyano, carbamoyl, aminosulphonyl, $(C_1-C_4)$-alkyl, $(C_3-C_4)$cycloalkyl, $(C_1-C_4)$alkoxy, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$alkylsulphimino, or $R^1$ is optionally aryl, hetaryl or heterocyclyl, each optionally mono- or disubstituted identically or differently by halogen, cyano, carbamoyl, $(C_1-C_4)$alkyl, $(C_3-C_6)$cycloalkyl, $(C_1-C_4)$-alkoxy, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$alkylsulphimino, $(C_1-C_4)$alkylsulphoximino, $(C_1-C_4)$alkylcarbonyl, $(C_3-C_4)$trialkylsilyl, (=O) (in the case of heterocyclyl only) or (=O)$_2$ (in the case of heterocyclyl only), $R^2$, $R^3$ are independently hydrogen, cyano, halogen, nitro, acetyl, hydroxyl, amino, SCN, tri$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_4)$alkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$alkylthio, $(C_1-

$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, aminothiocarbonyl or NHCO—($C_1$-$C_4$)alkyl (($C_1$-$C_4$)alkylcarbonylamino), $R^7$ is hydrogen, cyano, halogen, acetyl, hydroxyl, amino, ($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_2$-$C_4$)alkenyl, ($C_2$-$C_4$)haloalkenyl, ($C_2$-$C_4$)alkynyl, ($C_2$-$C_4$)haloalkynyl, ($C_1$-$C_4$)alkoxy, ($C_1$-$C_4$)haloalkoxy, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl or ($C_1$-$C_4$)haloalkylsulphonyl, Q is a heteroaromatic 8-, 9-, 10-, 11- or 12-membered fused bicyclic or tricyclic ring system, where the ring system is optionally mono- or polysubstituted identically or differently, and where the substituents may independently be selected from hydrogen, cyano, halogen, nitro, acetyl, hydroxyl, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_4$)alkyl, ($C_2$-$C_6$)haloalkynyl, ($C_1$-$C_6$)alkoxy, ($C_1$-$C_6$)haloalkoxy, ($C_1$-$C_6$)haloalkoxy-($C_1$-$C_6$)alkyl, ($C_2$-$C_6$)alkenyloxy-($C_1$-$C_6$)alkyl, ($C_2$-$C_6$)haloalkenyloxy-($C_1$-$C_6$)alkyl, ($C_1$-$C_6$)cyanoalkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkyl, ($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylcarbonyl-($C_1$-$C_6$)alkyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), or where the substituents may independently be selected from phenyl or a 5- or 6-membered heteroaromatic ring, where phenyl or the ring may optionally be mono- or polysubstituted identically or differently by $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n is 0, 1 or 2, where, in the case of the structural unit A4, Q is none of the following ring systems:

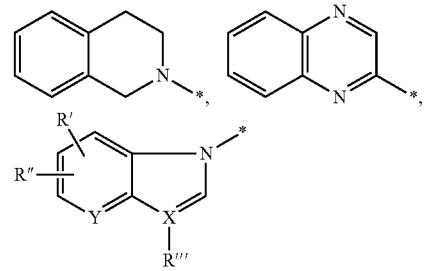

where X and Y, which may be the same or different, are carbon or nitrogen, R''' is hydrogen, aldehyde, oxime or —C(O)O—$R_a$, with the proviso that X is carbon, where $R_a$ is $C_1$-$C_6$-alkyl, R' and R'', which may be the same or different, are hydrogen, halogen, cyano, nitro, $C_1$-$C_6$-alkyl or $C_1$-$C_6$-alkoxy, and, in addition, when Aa is =C(H)—, in the case of the compounds of the formula (I), Q is not Q1, Q2, Q3, Q4, Q5, Q6, Q7, Q8, Q9, Q10, Q15, or Q17.

3. The compound of formula (I) or (I') according to claim 1, wherein

Aa is nitrogen or =C($R^7$)—,
Ab is nitrogen or =C(H)—,
Ac is nitrogen or =C(H)—,
Ad is nitrogen or =C(H)—,
Ae is nitrogen or =C(H)—, where Ab, Ac, Ad and Ae cannot all be nitrogen, optionally resulting in one of the following structural units: A1, A2, A3, A4, A5, A7, A8, A9, A10, A11, A12, A13, A14, A15, A17, A19, A20, A21, A22, A23, A24, A25, A26, A27, A29, A30, A31, A32, A33, A34, A35, A36, A37, A39, A41, A42, A43, or A44, $R^1$ is ($C_1$-$C_4$)-alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl or ($C_1$-$C_4$)alkylsulphonyl-($C_1$-$C_4$)alkyl, $R^2$, $R^3$ are independently hydrogen, cyano, halogen, nitro, hydroxyl, amino, SCN, tri-($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulphinyl, ($C_1$-$C_4$)haloalkylsulphinyl, ($C_1$-$C_4$)alkylsulphonyl, ($C_1$-$C_4$)haloalkylsulphonyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl or NHCO—($C_1$-$C_4$)alkyl (($C_1$-$C_4$)alkylcarbonylamino), $R^7$ is hydrogen, halogen, cyano, $(C_1-C_4)$alkyl or $(C_1-C_4)$haloalkyl, Q is a heteroaromatic 9-membered or 12-membered fused bicyclic or tricyclic ring system selected from the group consisting of Q1 to Q20

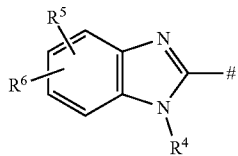
Q1

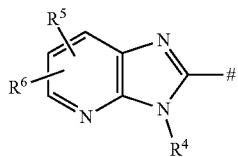
Q2

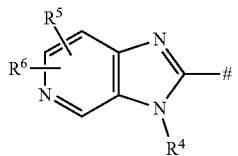
Q3

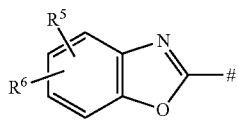
Q4

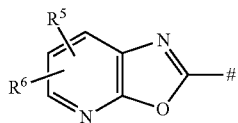
Q5

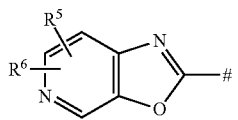
Q6

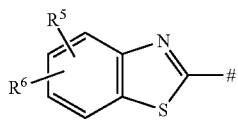
Q7

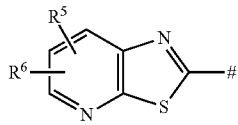
Q8

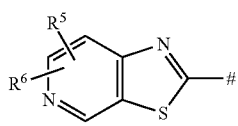
Q9

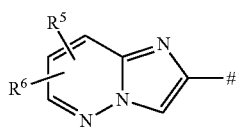
Q10

-continued

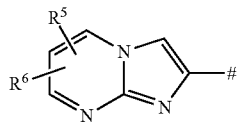
Q11

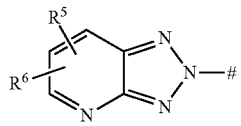
Q12

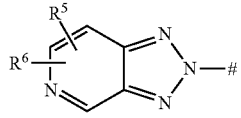
Q13

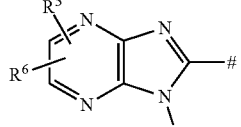
Q14

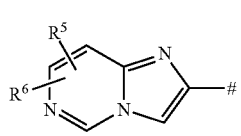
Q15

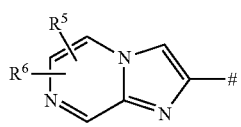
Q16

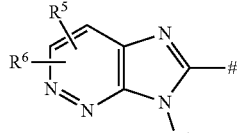
Q17

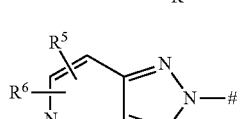
Q18

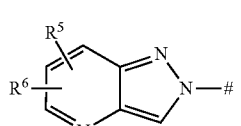
Q19

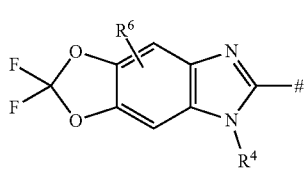
Q20

$R^4$ is hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, (C$_3$-C$_6$)cycloalkyl-(C$_3$-C$_6$)cycloalkyl, (C$_1$-C$_4$)alkyl-(C$_3$-C$_6$)cycloalkyl, halo(C$_3$-C$_6$)cycloalkyl, (C$_1$-C$_4$)alkylthio-(C$_1$-C$_4$)alkyl, (C$_1$-C$_4$)alkylsulphinyl-(C$_1$-C$_4$)alkyl, (C$_1$-C$_4$)alkylsulphonyl-(C$_1$-C$_4$)alkyl or (C$_1$-C$_4$)alkylcarbonyl-(C$_1$-C$_4$)alkyl, R$^5$, R$^6$ are independently hydrogen, cyano, halogen, (C$_1$-C$_4$)alkyl, (C$_1$-C$_4$)haloalkyl, (C$_2$-C$_4$)alkenyl, (C$_2$-C$_4$)haloalkenyl, (C$_2$-C$_4$)alkynyl, (C$_2$-C$_4$)haloalkynyl, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, (C$_1$-C$_4$)alkoxy, (C$_1$-C$_4$)haloalkoxy, (C$_1$-C$_4$)alkoxyimino, (C$_1$-C$_4$)alkylthio, (C$_1$-C$_4$)haloalkylthio, (C$_1$-C$_4$)alkylsulphinyl, (C$_1$-C$_4$)haloalkylsulphinyl, (C$_1$-C$_4$)alkylsulphonyl, (C$_1$-C$_4$)haloalkylsulphonyl, (C$_1$-C$_4$)alkylsulphonyloxy, (C$_1$-C$_4$)alkylcarbonyl, (C$_1$-C$_4$)haloalkylcarbonyl, aminocarbonyl, (C$_1$-C$_4$)alkylaminocarbonyl, di-(C$_1$-C$_4$)alkylaminocarbonyl, (C$_1$-C$_4$)alkylsulphonylamino, (C$_1$-C$_4$)alkylamino, di-(C$_1$-C$_4$)alkylamino, aminosulphonyl, (C$_1$-C$_4$)alkylaminosulphonyl or di-(C$_1$-C$_4$)alkylaminosulphonyl, n is 0, 1 or 2, where, when Aa is =C(H)—, in the case of the compounds of the formula (I), Q is not Q1, Q2, Q3, Q4, Q5, Q6, Q7, Q8, Q9, Q10, Q15, or Q17.

4. The compound of formula (I) or (I') according to claim 1, wherein

Aa is nitrogen or =C(R$^7$)—,
Ab is nitrogen or =C(H)—,
Ac is nitrogen or =C(H)—,
Ad is nitrogen or =C(H)—,
Ae is nitrogen or =C(H)—,
where Ab, Ac, Ad and Ae cannot all be nitrogen,
optionally resulting in one of the following structural units: A1, A2, A4, A5, A7, A9, A11, A12, A13, A19, A20, A21, A22, A23, A24, A26, A27, A29, A31, A33, A34, A35, A41, A42, A43, or A44, R$^1$ is (C$_1$-C$_4$)-alkyl, (C$_1$-C$_4$)-haloalkyl or (C$_3$-C$_6$)-cycloalkyl, R$^2$, R$^3$ are independently hydrogen, cyano, halogen, (C$_1$-C$_4$)-alkyl, (C$_1$-C$_4$)-alkoxy, (C$_1$-C$_4$)-haloalkyl, (C$_1$-C$_4$)-haloalkoxy, (C$_1$-C$_4$)-alkylthio, (C$_1$-C$_4$)-alkylsulphinyl, (C$_1$-C$_4$)-alkylsulphonyl, (C$_1$-C$_4$)-haloalkylthio, (C$_1$-C$_4$)-haloalkylsulphinyl, (C$_1$-C$_4$)-haloalkylsulphonyl or NHCO—(C$_1$-C$_4$)-alkyl ((C$_1$-C$_4$)-alkylcarbonylamino), R$^7$ is hydrogen, halogen, cyano, (C$_1$-C$_4$)alkyl or (C$_1$-C$_4$)haloalkyl, Q is a heteroaromatic 9-membered or 12-membered fused bicyclic or tricyclic ring system selected from the group consisting of Q1, Q2, Q3, Q5, Q6, Q8, Q9, Q10, Q11, Q12, Q13, Q15, Q16, Q17, Q18, Q19 and Q20, R$^4$ is hydrogen, (C$_1$-C$_4$)alkyl or (C$_1$-C$_4$)-alkoxy-(C$_1$-C$_4$)alkyl, R$^5$ is hydrogen, cyano, halogen, (C$_1$-C$_4$)alkyl, (C$_1$-C$_4$)haloalkyl, (C$_3$-C$_6$)cycloalkyl, (C$_3$-C$_6$)cycloalkyl-(C$_3$-C$_6$)cycloalkyl, (C$_1$-C$_4$)alkyl-(C$_3$-C$_6$)cycloalkyl, (C$_1$-C$_4$)alkoxy, (C$_1$-C$_4$)haloalkoxy, (C$_1$-C$_4$)alkoxyimino, (C$_1$-C$_4$)alkylthio, (C$_1$-C$_4$)haloalkylthio, (C$_1$-C$_4$)alkylsulphinyl, (C$_1$-C$_4$)haloalkylsulphinyl, (C$_1$-C$_4$)alkylsulphonyl, (C$_1$-C$_4$)haloalkylsulphonyl, (C$_1$-C$_4$)alkylcarbonyl, (C$_1$-C$_4$)haloalkylcarbonyl, (C$_1$-C$_4$)alkylaminocarbonyl, di-(C$_1$-C$_4$)alkylaminocarbonyl, (C$_1$-C$_4$)alkylsulphonylamino, (C$_1$-C$_4$)alkylaminosulphonyl or di-(C$_1$-C$_4$)alkylaminosulphonyl, R$^6$ is hydrogen, n is 0, 1 or 2, where, when Aa is =C(H)—, in the case of the compounds of the formula (I), Q is not Q1, Q2, Q3, Q5, Q6, Q8, Q9, Q10, Q15, or Q17.

5. The compound of the formula (I) or (I') according to claim 1, wherein Aa is nitrogen or =C(R$^7$)—,
Ab is =C(H)—,
Ac is =C(H)—,
Ad is =C(H)—,
Ae is nitrogen or =C(H)—,
resulting in one of the following structural units: A1, A4, A23, A26, or A33, R$^1$ is methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, R$^2$, R$^3$ are independently hydrogen, fluorine, chlorine, bromine, iodine, cyano, methyl, ethyl, methoxy, trifluoromethyl, trifluoromethoxy or trifluoromethylthio, R$^7$ is hydrogen, fluorine, chlorine, bromine, cyano, methyl, ethyl or trifluoromethyl, Q is a heteroaromatic 9-membered fused bicyclic ring system selected from the group consisting of Q1, Q2, Q3, Q16, Q17 and Q20, R$^4$ is hydrogen, methyl, ethyl, isopropyl, methoxymethyl or methoxyethyl, R$^5$ is fluorine, chlorine, bromine, fluoromethyl, difluoromethyl, trifluoromethyl, fluoroethyl (CH$_2$CFH$_2$, CHFCH$_3$), difluoroethyl (CF$_2$CH$_3$, CH$_2$CHF$_2$, CHFCFH$_2$), trifluoroethyl, (CH$_2$CF$_3$, CHFCHF$_2$, CF$_2$CFH$_2$), tetrafluoroethyl (CHFCF$_3$, CF$_2$CHF$_2$), pentafluoroethyl, trifluoromethoxy, difluorochloromethoxy, dichlorofluoromethoxy, trifluoromethylthio, trifluoromethylsulphinyl or trifluoromethylsulphanyl, R$^6$ is hydrogen, n is 0, 1 or 2, where, when Aa is =C(H)—, in the case of the compounds of the formula (I), Q is not Q1, Q2, Q3, or Q17.

6. The compound of formula (I) or (I') according to claim 1, wherein

Aa is nitrogen or =C(R$^7$)—,
Ab is =C(H)—,
Ac is =C(H)—,
Ad is =C(H)—,
Ae is nitrogen or =C(H)—,
resulting in one of the following structural units: A1, A4, A23, A26, or A33

R$^1$ is methyl or ethyl,
R$^2$ is hydrogen, chlorine, methoxy or trifluoromethyl,
R$^3$ is hydrogen,
R$^7$ is hydrogen, Q is a heteroaromatic 9-membered or 12-membered fused bicyclic ring system selected from the group consisting of Q1, Q2, Q3, Q16, Q17, and Q20, R$^4$ is hydrogen or methyl,
R$^5$ is trifluoromethyl or pentafluoroethyl,
R$^6$ is hydrogen,
n is 0, 1 or 2, where, when Aa is =C(H)—, in the case of the compounds of the formula (I), Q is not Q1, Q2, Q3, or Q17.

7. The compound of the formula (I') according to claim 1.

8. The compound of formula (I) or (I') according to claim 1, selected from the group consisting of I-3, I-4, I-6, I-7, I-8, I-9, I-10, I-13, I-14, I-15, I-16, I-17, I-18, I-19, I-20, I-21, I-23, I-24, I-27, I-28, I-29, I-30, I-31, I-32, I-33, I-34, I-35, I-36, I-37, I-38, I-40, I-41, I'-42, I'-43, I'-44, I'-45, I'-47, I'-48, I'-49, I'-50, I'-51, I'-52, I'-53, I'-54, I-55, I-56, I-57, I'-58, I-59,
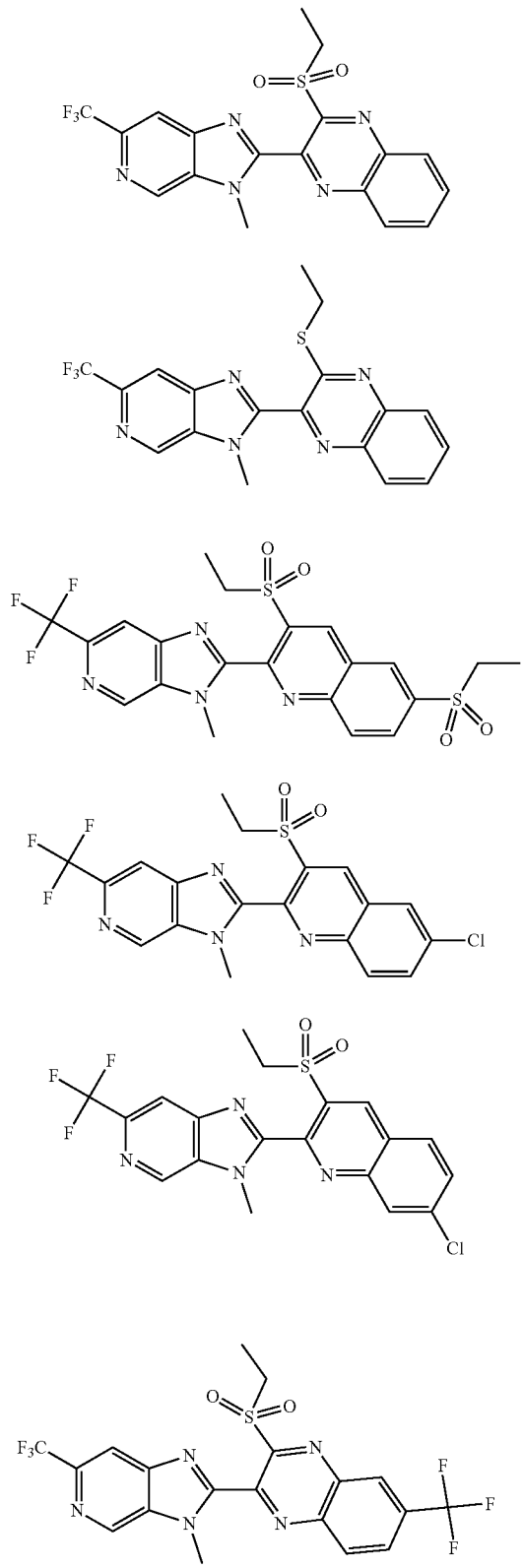
-continued
I-10
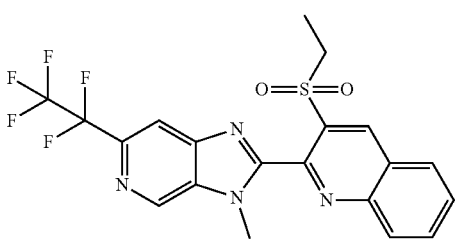
I-13
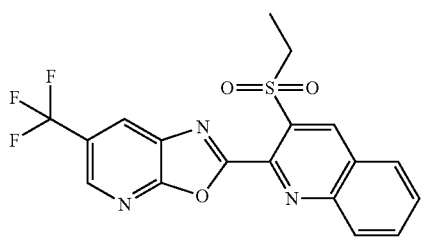
I-14
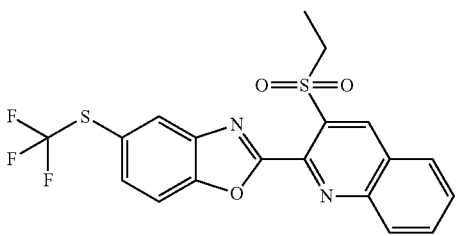
I-15
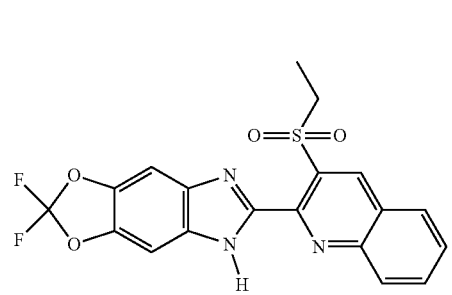
I-16
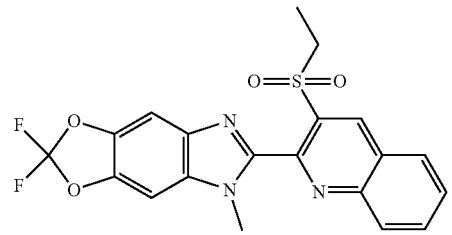
I-17
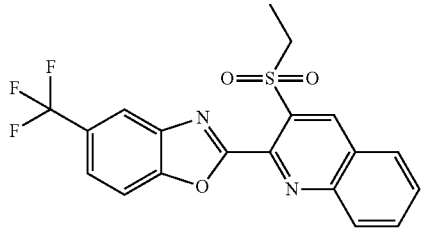

I-18, I-19, I-20, I-21, I-23, I-24, I-27, I-28, I-29, I-30, I-31, I-32

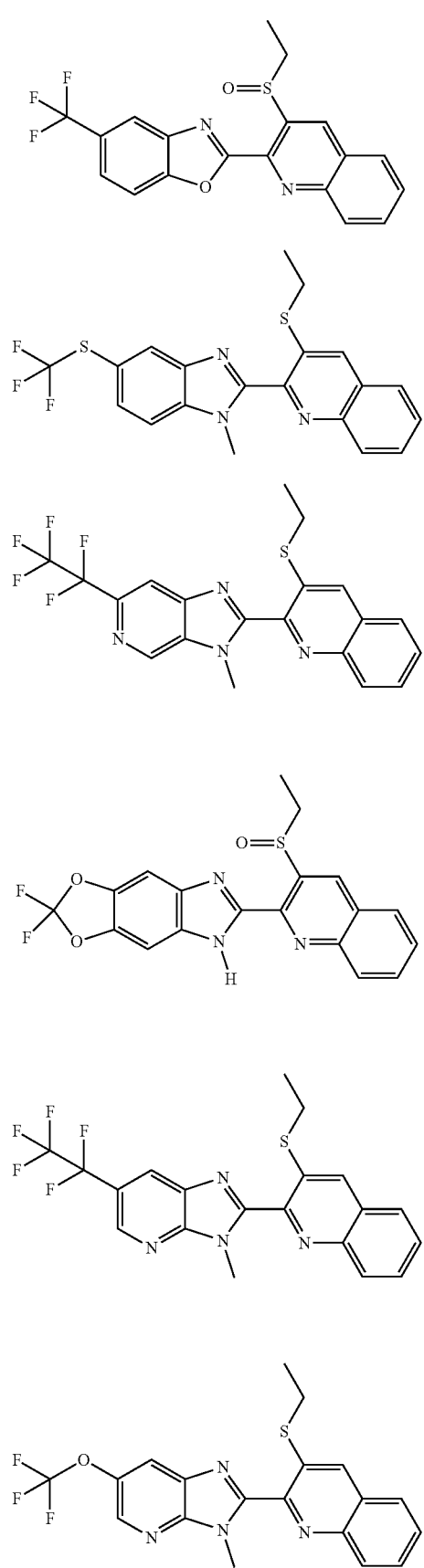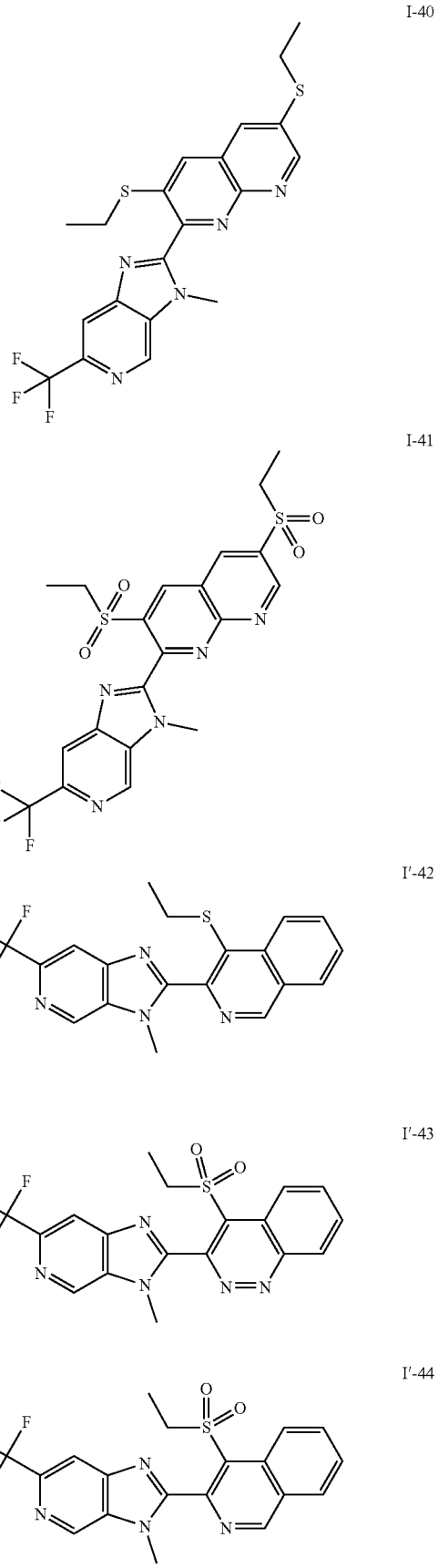

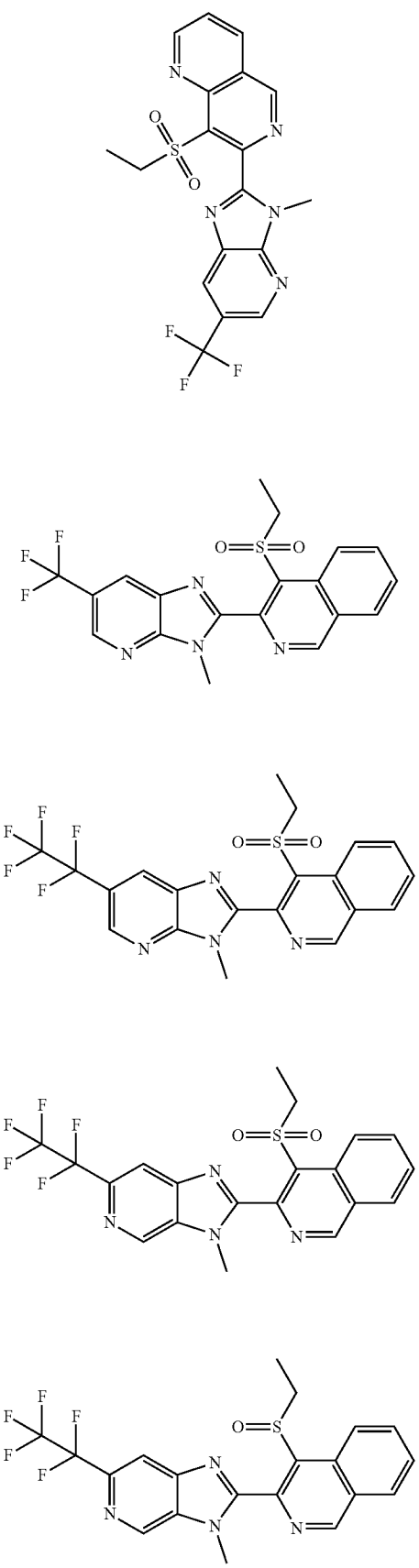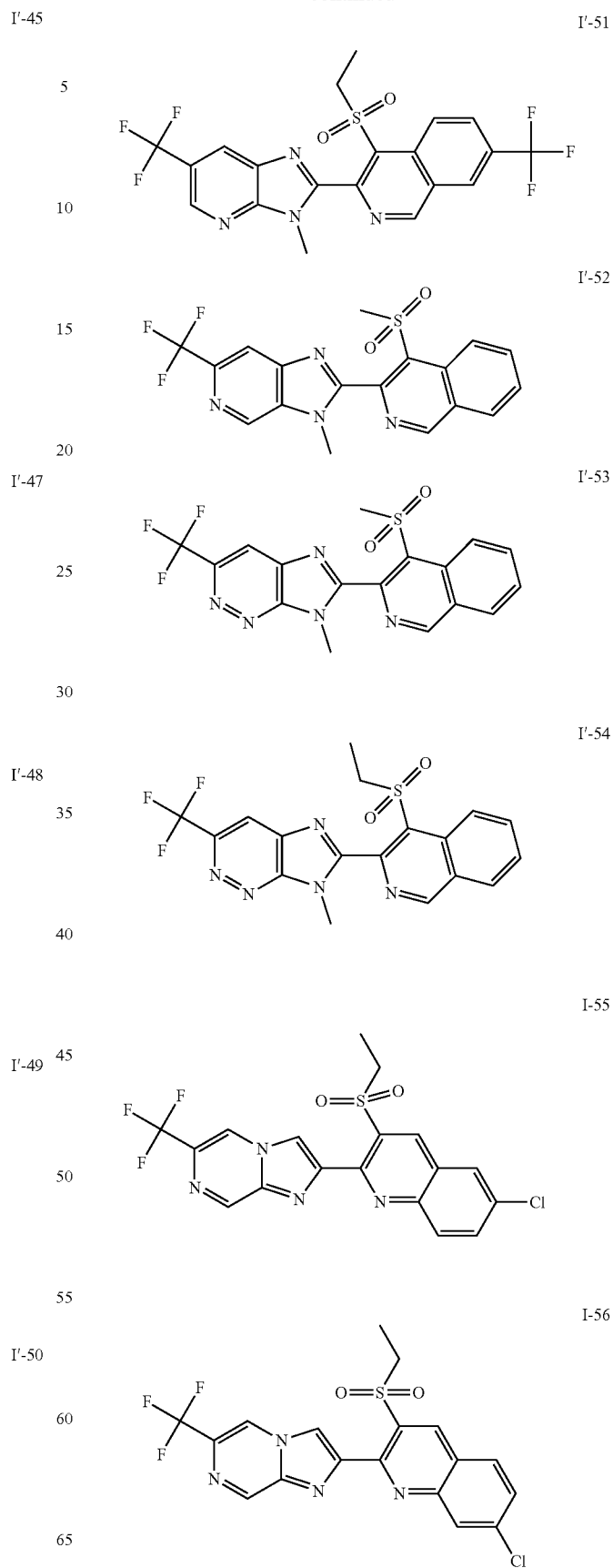

-continued

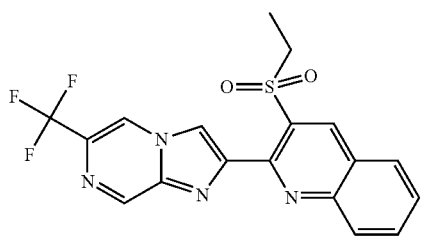
I-57

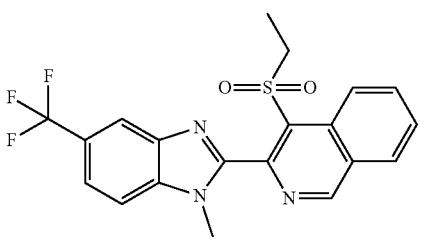
I′-58

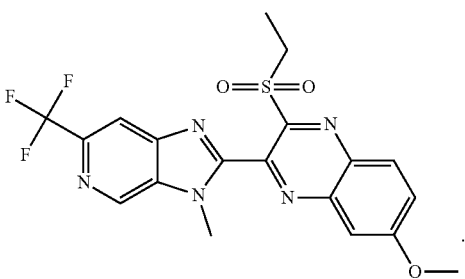
I-59

9. A compound of formula (III-1)

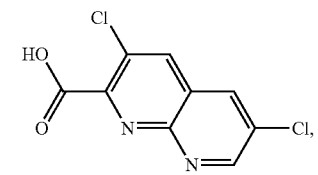
(III-2)

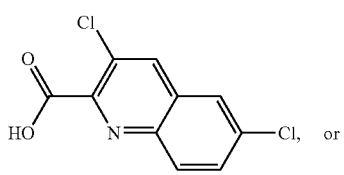 or

-continued

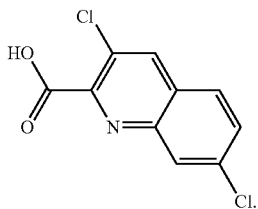
(III-3)

10. The compound of formula (I′) according to claim 7, wherein Q is

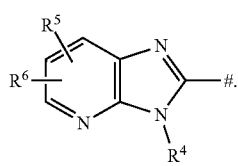
Q2

11. The compound of formula (I′) according to claim 7, wherein n is 2.

12. The compound of formula (I′) according to claim 7, wherein $R^1$ is ethyl.

13. The compound of formula (I′) according to claim 7, wherein $R^4$ is methyl.

14. The compound of formula (I′) according to claim 7, wherein
Aa is =C($R^7$)—, and
$R^7$ is hydrogen.

15. The compound of formula (I′) according to claim 7, wherein Ab, Ac, Ad, and Ae are each =C(H)—.

16. An agrochemical formulation comprising one or more compounds of formula (I) or formula (I′) according to claim 1 and also one or more extenders and/or surfactants.

17. The agrochemical formulation according to claim 16, additionally comprising a further active agrochemical ingredient.

18. A method for controlling one or more animal pests, comprising allowing a compound of formula (I) or formula (I′) according to claim 1 or an agrochemical formulation thereof to act on the animal pests and/or a habitat thereof.

19. A product comprising the compound of formula (I) or formula (I′) according to claim 1 or an agrochemical formulation thereof for controlling one or more animal pests.

\* \* \* \* \*